(12) United States Patent
Cavalli et al.

(10) Patent No.: US 11,766,224 B2
(45) Date of Patent: Sep. 26, 2023

(54) VISUALIZED VIRTUAL AGENT

(71) Applicant: MYMELEON AG, Zug (CH)

(72) Inventors: Fabio Cavalli, Muzzano (CH); Francesco Cavalli, Muzzano (CH); Hans-Lothar Arth, Berlin (DE)

(73) Assignee: MYMELEON AG, Zug (CH)

( * ) Notice: Subject to any disclaimer, the term of this patent is extended or adjusted under 35 U.S.C. 154(b) by 212 days.

(21) Appl. No.: 17/280,201

(22) PCT Filed: Sep. 27, 2019

(86) PCT No.: PCT/EP2019/076332
§ 371 (c)(1),
(2) Date: Mar. 26, 2021

(87) PCT Pub. No.: WO2020/065081
PCT Pub. Date: Apr. 2, 2020

(65) Prior Publication Data
US 2021/0338177 A1 Nov. 4, 2021

(30) Foreign Application Priority Data
Sep. 27, 2018 (EP) ..................................... 18197392

(51) Int. Cl.
*A61B 5/00* (2006.01)
*A61B 5/024* (2006.01)
*A61B 5/16* (2006.01)

(52) U.S. Cl.
CPC .............. *A61B 5/744* (2013.01); *A61B 5/024* (2013.01); *A61B 5/165* (2013.01)

(58) Field of Classification Search
CPC .......... A61B 5/024; A61B 5/165; A61B 5/744
See application file for complete search history.

(56) References Cited

U.S. PATENT DOCUMENTS

2007/0050715 A1* 3/2007 Behar .................... G16H 40/67
600/300
2009/0318773 A1* 12/2009 Jung .................... A61B 5/4803
600/300

(Continued)

OTHER PUBLICATIONS

International Search Report and Written Opinion for International Patent Application No. PCT/EP2019/076332 dated Nov. 7, 2019, 12 pages.

(Continued)

*Primary Examiner* — Christopher A Flory
(74) *Attorney, Agent, or Firm* — AMIN, TUROCY & WATSON, LLP

(57) ABSTRACT

The present invention relates to a visualized virtual agent configured to provide a visual response to a user, wherein the visualized virtual agent is further configured to provide an artificial physiological color change response to a user on the basis of one or more user-specific parameter, wherein the visualized virtual agent is configured to acquire user-specific data for at least one user-specific parameter using at least one sensor, the one or more user-specific parameter comprising activity data of the user and/or physio-psychological data of the user, and wherein the artificial physiological color change response is provided in response to monitored changes of the acquired user-specific data for the at least one user-specific parameter of the activity data of the user and/or the physio-psychological data of the user, the artificial physiological color change response comprising at least in part a color change of the visualized virtual agent.

15 Claims, 13 Drawing Sheets

(56) References Cited

U.S. PATENT DOCUMENTS

| | | | |
|---|---|---|---|
| 2011/0172743 A1 | 7/2011 | Davis et al. | |
| 2012/0071771 A1 | 3/2012 | Behar | |
| 2012/0266088 A1* | 10/2012 | Finn | G06F 3/14 |
| | | | 715/757 |
| 2013/0245389 A1 | 9/2013 | Schultz et al. | |
| 2015/0038806 A1* | 2/2015 | Kaleal, III | A61B 5/4833 |
| | | | 600/301 |
| 2016/0077547 A1* | 3/2016 | Aimone | A61B 5/1114 |
| | | | 345/8 |
| 2016/0086500 A1 | 3/2016 | Kaleal, III | |
| 2017/0011258 A1 | 1/2017 | Pitre et al. | |
| 2017/0206795 A1* | 7/2017 | Kaleal, III | G16H 40/63 |
| 2018/0199156 A1 | 7/2018 | Gandhi et al. | |
| 2018/0261332 A1* | 9/2018 | Baeuerle | G16H 70/60 |
| 2018/0348863 A1* | 12/2018 | Aimone | A61B 5/369 |
| 2019/0015025 A1* | 1/2019 | Desborough | A61M 5/003 |
| 2020/0090813 A1* | 3/2020 | Hann | A61B 5/0205 |
| 2020/0133394 A1* | 4/2020 | Hann | A61B 5/163 |

OTHER PUBLICATIONS

European Intention to Grant a Patent for European Patent Application No. 19773864.4 dated Jul. 19, 2022.

\* cited by examiner

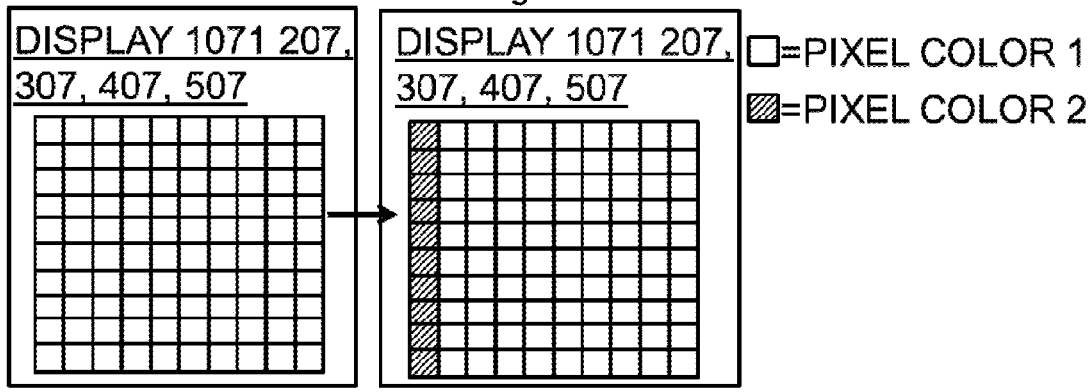
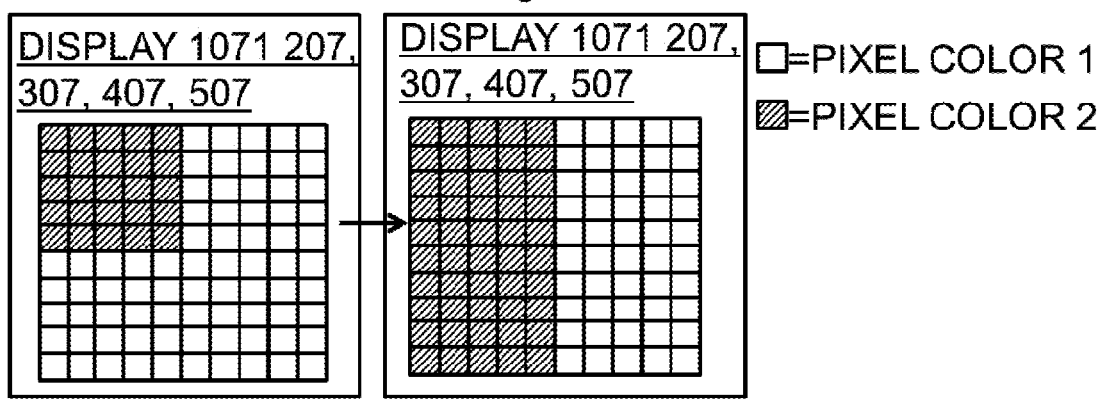

VISUALIZED VIRTUAL AGENT

The present invention relates to a visualized virtual agent configured to provide a visual response to a user, wherein the visualized virtual agent is further configured to provide an artificial physiological color change response to a user on the basis of one or more user-specific parameter, wherein the visualized virtual agent is configured to acquire user-specific data for at least one user-specific parameter using at least one sensor, the one or more user-specific parameter comprising activity data of the user and/or physio-psychological data of the user, and wherein the artificial physiological color change response is provided in response to monitored changes of the acquired user-specific data for the at least one user-specific parameter of the activity data of the user and/or the physio-psychological data of the user, the artificial physiological color change response comprising at least in part a color change of the visualized virtual agent.

BACKGROUND OF THE INVENTION

Virtual agents in connection with electronic devices, like smartphones or smart speakers, are becoming increasingly popular in the modern world and nowadays virtual agents are even indispensable in some cases or applications. Virtual agents may provide an intuitive interface between a user and a system or device in order to enhance and facilitate the interaction therewith. Virtual agents often serve as personal digital assistants in order to organize everyday life, like for example saving appointments in the user's calendar or compiling a shopping list or setting an alarm clock. Moreover providing virtual agents on various wearable electronic devices make them available from all locations and at all times. Therefore one advantage of applying a virtual agent via an electronic device is, for example, that a user may be reminded about an appointment regardless of the location of the user at a predefined point in time. Furthermore, a various number of modern electronic devices are internet-enabled or web-ready, so that virtual agent applications provided on these devices may connect to the World Wide Web and may provide suitable information relating to a user's individual request. A user may therefore decide either to access the World Wide Web through a suitable web browser and to initiate a search request through a search engine or Internet search site by typing in the search request into the appropriate search field or to use a virtual agent application to perform the search. If a search field is provided within the virtual agent application then the user may type in the search request in said search field or optionally if communication through voice recognition is provided the user may just initiate the search request by oral question. In addition, the virtual agent may provide the requested information in oral form to the user. For example a user may communicate through spoken words or a natural language interface with known virtual agents such as Cortana® by Microsoft Corporation or Siri® by Apple Inc. Moreover the virtual agent may be applied hands-free, which is particularly advantageous like, for example, if the user is driving a car and would like to operate a navigation system at the same time.

Virtual agents known in the art are predominantly used to provide specific information, like for example in relation to weather forecast, traffic jams, route guidance and so on or to perform a requested task, like playing a particular audio or video file or setting up a telephone connection. The imitation of natural human speech in connection with oral responses provided by a virtual agent is still a challenging task. As is known human speech is not only characterized by simply speaking out words, moreover human speech is also affected by emotions, mood or the mental state or social surroundings of a speaker and further by body language, like gestures, mimics and so on. Consequently the oral response provided by most of known virtual agents is immediately recognized as artificial voice response and said voice response is characterized in being mainly kind, facial and business-like.

Virtual agents may be provided as embodied agents to provide a visualized virtual agent which is represented graphically with a body. An embodied virtual agent may communicate with a user thereby providing the same verbal and non-verbal cues like a real human being during a conversation. Thus one purpose of applying an embodied agent is to combine gesture, facial expression and speech to enable the imitation of a face-to-face communication with users.

Mood lighting devices are known in the art and are commonly used to create a pleasant environment in the home. Mood lighting creates a pleasant ambience and may enhance or create a certain mood. Mood lighting devices are available for providing desired lighting effects such as color changing. Such mood lighting devices are generally adjusted by a user, for example, a user is able to adjust the mood lighting device to a specific color in order to create a certain mood. Thus, the lighting effects of such mood lighting devices solely depend on user's preferences.

It is an objective of the present invention to provide an improved visualized virtual agent. It is a further objective of the present invention to provide an improved visualized virtual agent providing a visual response to a user. It is a further objective of the present invention to provide an improved visualized virtual agent providing an improved visual response to a user. It is a further objective of the present invention to provide a visualized virtual agent providing an improved visual response to a user. It is a further objective of the present invention to provide a computer-implemented method for generating of an improved visualized virtual agent providing an improved visual response to a user.

Said objective is solved by the technical teaching of the independent claims. Further advantageous embodiments of the invention result from the dependent claims, the description, the figures and the examples.

BRIEF DESCRIPTION OF THE INVENTION

The present invention relates to a visualized virtual agent configured to provide a visual response to a user and configured to monitor over time one or more user-specific parameter, wherein user-specific data for at least one user-specific parameter are acquired by at least one sensor, the user-specific parameter comprising activity data of the user and/or physio-psychological data of the user, wherein the visualized virtual agent is configured to provide an artificial physiological color change response to a user for a current state of the user and/or for at least one visualized virtual agent state, wherein the at least one visualized virtual agent state and/or the current state of the user is determined on the basis of the activity data of the user and/or of the physio-psychological data of the user; wherein the visualized virtual agent is configured to adapt the artificial physiological color change response to monitored changes of the activity data of the user and/or the physio-psychological data of the user, wherein the adaption of the artificial physiological color change response comprises at least in part a color change of the visualized virtual agent for the at least one visualized virtual agent state and/or the current state of the user.

According to an aspect of the invention determining the current state of a user may comprise determining a selection of one or more user-specific parameter as a basis for generating of the artificial physiological color change response to the user.

According to an aspect of the invention the visualized virtual agent may be configured to monitor, to collect and to analyze a plurality of data for a plurality of user-specific parameter for activity data of a user and/or physio-psychological data of a user and may be configured to determine the current state of the user based on the monitored, collected and analyzed plurality of data and may be configured to determine a selection of one or more user-specific parameter selected from the entire user-specific parameter in order to provide a specific selection of one or more user-specific parameter as a basis for generating the artificial physiological color change response to the user.

According to an aspect of the invention the visualized virtual agent may be configured to provide an artificial physiological color change response to a user based on a first selection of one or more user-specific parameter from the activity data of a user and/or the physio-psychological data of a user for a first state of a user and may be further configured to provide an artificial physiological color-change response to a user based on a second selection of one or more user-specific parameter from the activity data of a user and/or physio-psychological data of a user for a second state of a user, wherein the visualized virtual agent may be configured to change between the first state of the user and the second state of the user.

According to an aspect of the invention determining the visualized virtual agent state may comprise determining a selection of one or more user-specific parameter as a basis for generating of the artificial physiological color change response to the user and wherein the visualized virtual agent may be configured to provide an artificial physiological color change response to a user based on a first selection of one or more user-specific parameter from the activity data of a user and/or the physio-psychological data of a user for a first visualized virtual agent state and be further configured to provide an artificial physiological color change response to a user based on a second selection of one or more user-specific parameter from the activity data of a user and/or physio-psychological data of a user for a second visualized virtual agent state, wherein the visualized virtual agent is configured to change between the first visualized virtual agent state and the second visualized virtual agent state.

According to an aspect of the invention the first visualized virtual agent state may comprise an active communication visualized virtual agent state and the second visualized virtual agent state may comprise a passive or monitoring visualized virtual agent state.

According to an aspect of the invention the visualized virtual agent may be configured to provide different artificial physiological color change responses to a user on the basis of different specific selections of one or more user-specific parameter of activity data of a user and/or physio-psychological data of a user for different visualized virtual agent states and different states of a user, wherein the visualized virtual agent is configured to change between each visualized virtual agent state and/or each state of the user in order to provide artificial physiological color change responses for the current situation of a user.

According to an aspect of the invention the visualized virtual agent may be configured to provide long-term recognizing and/or measuring and/or monitoring of activity parameter and/or physio-psychological parameter of the user over time.

According to an aspect of the invention the physio-psychological data of the user may be based on a present behavior and/or a current physiological condition and/or a current mental state and/or medical condition of the user.

According to an aspect of the invention the visualized virtual agent may be displayed two dimensionally or three dimensionally on a display device.

According to an aspect of the invention the visual response may comprise a posture, and/or a motion of the visualized virtual agent and wherein the audio response comprises a sound, a sound volume, an emphasis, and/or an accent of the visualized virtual agent on the basis of the activity data of the user and/or physio-psychological of the user.

According to an aspect of the invention the at least one sensor may comprise audio-visual sensors, activity sensors, physiological sensors, biometric sensors, a heart rate sensor, a blood pressure sensor/monitor, a weight scale, motion sensors, an optical sensor, a video sensor, an audio sensor, a blood glucose monitor, a blood oxygen saturation monitor, a hydration monitor, a skin/body temperature thermometer, a respiration monitor, electroencephalogram (EEG) electrodes, bed sensors, accelerometer, activity sensors/trackers, a video camera, a depth sensor, an electro dermal activity (EDA) sensor, a portable global positioning system (GPS) sensor, and/or a microphone.

According to an aspect of the invention the at least one sensor may be configured to acquire physio-psychologic parameters of the user by speech recognition, face recognition, measurement of pulse, measurement of breathing, measurement of blood pressure, and/or measurement of the electric conductivity of the skin.

According to an aspect of the invention the visualized virtual agent may be configured to provide a color change response comprising at least in part a color change of the visualized virtual agent in the range between a first color value and a second color value, wherein the range between the first color value and the second color value is subdivided into intervals, wherein for each interval and subsequent interval a specific amount of the pixels is adapted to the second color value, wherein the visualized virtual agent is rendered with the first color by 100% of the pixel of the visualized virtual agent and for each of the intervals in the range between the first and the second color value, at least a part of the pixels add up and are rendered with the second color until reaching the second color value, where 100% of the pixels of the visualized virtual agent is rendered with the second color.

The present invention further relates to a system for providing a visualized virtual agent providing an artificial physiological color change response to a user, the system comprising: a memory; at least one sensor configured to collect sensor data for at least one user-specific parameter of the user, at least one display device configured to display the visualized virtual agent; at least one processor configured to execute executable components stored on the memory, the executable components comprising: a user-specific parameter monitoring component configured to monitor one or more user-specific parameter of the user, wherein the user-specific parameter monitoring component is configured to receive user-specific data for one or more user-specific parameter of the user, the user-specific parameter comprising activity data of the user and/or physio-psychological data of the user, wherein user-specific data for at least one user-specific parameter are acquired from the at least one sensor; a user-specific data analysis component configured to analyze the user-specific data monitored by the user-specific parameter monitoring component and to determine monitored changes of the activity data of the user and/or physio-psychological data of the user; a visualized virtual agent rendering component configured to adapt the artificial physiological color change response to the determined monitored changes of the activity data of the user and/or the physio-psychological data of the user, wherein the adaption of the artificial physiological color change response comprises at least in part a color change of the visualized virtual agent; wherein the user-specific data analysis component further comprises: a current state of the user determination component configured to determine a current state of the user based on the user-specific data monitored by the user-specific parameter monitoring component, and/or a visualized virtual agent state determination component configured to determine a visualized virtual agent based on the user-specific data monitored by the user-specific parameter monitoring component.

According to an aspect of the invention the user-specific data analysis component may further comprises: a user-specific parameter selection component configured to determine a selection of one or more user-specific parameter from the one or more user-specific parameter as a basis for generating of the artificial physiological color change response.

The present invention further relates to a computer-implemented method for providing a visualized virtual agent configured to provide an artificial physiological color change response to a user, the method comprising the following steps: monitoring over time, by a user-specific parameter monitoring component, one or more user-specific parameter of a user, the one or more user-specific parameter comprising activity data of the user and/or physio-psychological data of the user, and acquiring, by the user specific parameter monitoring component, user-specific data for at least one user-specific parameter by at least one sensor; determining, by a current state of the user determination component, a current state of the user on the basis of the activity data of the user and/or the physio-psychological data of the user and/or determining, by a visualized virtual agent state determination component, a visualized virtual agent state on the basis of the activity data of the user and/or the physio-psychological data of the user; analyzing, by a user-specific data analysis component, the monitored one or more user-specific parameter of the user for the determined current state of the user and/or determined visualized virtual agent state; determining, by the user-specific data analysis component, monitored changes of the activity data of the user and/or the physio-psychological data of the user; providing, by the user-specific data analysis component, the monitored changes of the activity data of the user and/or the physio-psychological data of the user to a visualized virtual agent rendering component; adapting, by the visualized virtual agent rendering component, the artificial physiological color change response to the monitored changes of the activity data of the user and/or the physio-psychological data of the user, wherein the adaption of the artificial physiological color change response comprises at least in part a color change of the visualized virtual agent; rendering, by the visualized virtual agent rendering component, the visualized virtual agent on a display device.

According to an aspect of the invention the method further comprises the steps: determining, by a user-specific parameter selection component, a selection of one or more user-specific parameter based on the determined current state of the user and/or based on the determined visualized virtual agent state.

DESCRIPTION OF THE INVENTION

Surprisingly it has been found that a visualized virtual agent configured to provide a visual response to a user, wherein the visualized virtual agent is further configured to provide an artificial physiological color change response to a user on the basis of one or more user-specific parameter, wherein the visualized virtual agent is configured to acquire user-specific data for at least one user-specific parameter using at least one sensor, the one or more user-specific parameter comprising activity data of the user and/or physio-psychological data of the user, and wherein the artificial physiological color change response is provided in response to monitored changes of the acquired user-specific data for the at least one user-specific parameter of the activity data of the user and/or the physio-psychological data of the user, the artificial physiological color change response comprising at least in part a color change of the visualized virtual agent resolves the above objective.

The present invention relates to a visualized virtual agent configured to provide a visual response to a user which is further configured to provide an artificial physiological color change response to a user on the basis of user-specific parameter, wherein the visualized virtual agent is configured to acquire user-specific data for at least one user-specific parameter using at least one sensor, the user-specific parameter comprising activity data of the user and/or physio-psychological data of the user, and wherein the artificial physiological color change response is provided in response to monitored changes of the acquired user-specific data for the at least one user-specific parameter from the activity data of the user and/or the physio-psychological data of the user, the artificial physiological color change response comprising at least in part a color change of the visualized virtual agent.

The present invention further relates to a visualized virtual agent configured to provide a visual response to a user which is further configured to provide an artificial physiological color change response to a user for at least one visualized virtual agent state and/or for at least one state of the user, preferably a current state of the user, wherein the at least one visualized virtual agent state and/or the at least one state of the user, preferably the current state of the user is determined on the basis of user-specific parameter, wherein the visualized virtual agent is configured to acquire user-specific data for at least one user-specific parameter using at least one sensor, the user-specific parameter comprising activity data of the user and/or physio-psychological data of the user, and wherein the artificial physiological color change response is provided in response to monitored changes of the acquired user-specific data for the at least one user-specific parameter from the activity data of the user and/or the acquired physio-psychological data of the user, the artificial physiological color change response comprising at least in part a color change of the visualized virtual agent for the at least one determined visualized virtual agent state and/or determined current state of the user.

With other words, the present invention relates to a visualized virtual agent configured to provide a visual response to a user and configured to monitor over time one or more user-specific parameter, wherein user-specific data for at least one user-specific parameter are acquired by at least one sensor, the user-specific parameter comprising activity data of the user and/or physio-psychological data of the user, wherein the visualized virtual agent is configured to provide an artificial physiological color change response to a user for at least one visualized virtual agent state and/or for a current state of the user, wherein the at least one visualized virtual agent state and/or the current state of the user is determined on the basis of the activity data of the user and/or of the physio-psychological data of the user; wherein the visualized virtual agent is configured to adapt the artificial physiological color change response to monitored changes of the activity data of the user and/or the physio-psychological data of the user, wherein the adaption of the artificial physiological color change response comprises at least in part a color change of the visualized virtual agent for the at least one visualized virtual agent state and/or the current state of the user.

With other words, the present invention relates to a visualized virtual agent configured to provide a visual response to a user and configured to monitor over time one or more user-specific parameter, wherein user-specific data for at least one user-specific parameter are acquired by at least one sensor, the user-specific parameter comprising activity data of the user and/or physio-psychological data of the user, wherein the visualized virtual agent is configured to provide an artificial physiological color change response to a user for at least one visualized virtual agent state and/or for a current state of the user, wherein the at least one visualized virtual agent state and/or the current state of the user is determined on the basis of the activity data of the user and/or of the physio-psychological data of the user; wherein the visualized virtual agent is configured to adapt the artificial physiological color change response to monitored changes of the acquired user-specific data for the at least one user-specific parameter, wherein the adaption of the artificial physiological color change response comprises at least in part a color change of the visualized virtual agent for the at least one visualized virtual agent state and/or the current state of the user.

The present invention further relates to a visualized virtual agent configured to provide an artificial physiological color change response to a user for at least one visualized virtual agent state and/or for a current state of the user, wherein the visualized virtual agent is configured to provide a visual response to the user, wherein the at least one visualized virtual agent state and/or the current state of the user is determined on the basis of activity data of the user and/or of physio-psychological data of the user and wherein the visualized virtual agent is configured to adapt the visual response to monitored changes of the activity data of the user and/or the physio-psychological data of the user, wherein the adaption of the visual response comprises at least in part a color change of the visualized virtual agent for the at least one visualized virtual agent state and/or current state of the user.

The present invention further relates to a computer-implemented method for generating a visualized virtual agent configured to provide a visual response to a user which is further configured to provide an artificial physiological color change response to a user on the basis of user-specific parameter, wherein the visualized virtual agent is configured to acquire user-specific data for at least one user-specific parameter using at least one sensor, the user-specific parameter comprising activity data of the user and/or physio-psychological data of the user, and wherein the artificial physiological color change response is provided in response to monitored changes of the acquired user-specific data for the at least one user-specific parameter from the activity data of the user and/or the physio-psychological data of the user, the artificial physiological color change response comprising at least in part a color change of the visualized virtual agent.

The present invention further relates to a computer-implemented method for generating a visualized virtual agent configured to provide a visual response to a user and which is further configured to provide an artificial physiological color change response to a user for at least one visualized virtual agent state and/or for at least one state of the user, preferably a current state of the user, wherein the at least one visualized virtual agent state and/or the at least one state of the user, preferably the current state of the user is determined on the basis of user-specific parameter, wherein the visualized virtual agent is configured to acquire user-specific data for at least one user-specific parameter using at least one sensor, the user-specific parameter comprising activity data of the user and/or physio-psychological data of the user, and wherein the artificial physiological color change response is provided in response to monitored changes of the acquired user-specific data for the at least one user-specific parameter from the activity data of the user and/or the acquired physio-psychological data of the user, the artificial physiological color change response comprising at least in part a color change of the visualized virtual agent for the at least one determined visualized virtual agent state and/or determined current state of the user.

The present invention further relates to a computer-implemented method for generating a visualized virtual agent configured to provide a visual response to a user and configured to monitor over time one or more user-specific parameter, wherein user-specific data for at least one user-specific parameter are acquired by at least one sensor, the user-specific parameter comprising activity data of the user and/or physio-psychological data of the user, wherein the visualized virtual agent is configured to provide an artificial physiological color change response to a user for at least one visualized virtual agent state and/or for a current state of the user, wherein the at least one visualized virtual agent state and/or the current state of the user is determined on the basis of the activity data of the user and/or of the physio-psychological data of the user; wherein the visualized virtual agent is configured to adapt the artificial physiological color change response to monitored changes of the activity data of the user and/or the physio-psychological data of the user, wherein the adaption of the artificial physiological color change response comprises at least in part a color change of the visualized virtual agent for the at least one visualized virtual agent state and/or the current state of the user.

Some species exist in the nature, which may come in a range of colors and are known to have the ability to change color like, for example, chameleons. Some of the chameleon species are able to change the coloration of their skin, whereby their coloration and pattern may vary through combinations of different colors. Chameleon skin has a superficial layer which contains pigments. Under this superficial layer cells with guanine crystals are present. Changing the space between the guanine crystals causes a change of the wavelength of light reflected off the crystals and therefore results in a change of the color of the chameleon's skin. One of the functions of color change ability is camouflage, but most commonly color change of the skin is related to social signaling and related to reactions to temperature and other conditions. Thus, a chameleon is able to reflect his physiological condition through color change signals.

The term "artificial physiological color change" as used herein refers to a very specific kind of color change. Chameleons are the most prominent examples for physiological color changes. It is important that the artificial physiological color change is fluent. That means the color of the visualized virtual agent which is actually in the most preferred embodiment represented by a stylized chameleon, is flowing from one color constellation to another color constellation. The flowing of the color constellation or the color arrangement to a further color constellation or color arrangement of the visualized virtual agent is performed dot-wise, or pixel-wise, i.e. pixel by pixel or in case a pixel is not the preferred color unit, by each smallest color unit which is preferably smaller than 1 mm$^2$, more preferred smaller than 0.5 mm$^2$, more preferred smaller than 0.1 mm$^2$, more preferred smaller than 0.05 mm$^2$, still more preferred smaller than 0.01 mm$^2$. However, the artificial physiological color change is fluent and not spontaneous like a traffic light switching from green spontaneously to yellow and red. Moreover, the artificial physiological color change is not flashing like a warning lamp. Furthermore, the visualized virtual agent does not change its color completely at once within a short time frame, for instance, of less than one minute.

It is very important that the visualized virtual agent shows by its artificial physiological color change a tendency for the user if the user's behavior has a positive or negative impact on the user. This flowing or slowly flowing artificial physiological color change gives a signal to the user's subconscious mind telling the user to stop an unhealthy or unfavorable or harmful activity or to proceed with a healthy or favorable or unharmful activity. The inventors found that such a guidance of the user is much more accepted and followed by the user in comparison to hard indicators or hard warning signals like intensive audio warning or flashing lights or written warning messages. For example, in case the user is playing with his mobile phone for an hour, his activity might not have an adverse effect on the user so that the visualized virtual agent appears widely in green. In case the user continues playing with his mobile phone for several hours, the visualized virtual agent will fluently change its color dot-wise or pixel-wise or color-unit-wise over yellow, orange to red. During the artificial physiological color change process the visualized virtual agent appear in a plurality of color constellations or color arrangements, like a chameleon, which might also be presented in aggressive or dangerous or friendly looking designs depending on the impression which should be provided to the user's subconscious mind. Thus, the user receives the information unconsciously that his behavior or his activity is either beneficial, healthy, unharmful or unhealthy, unfavorable, harmful. Consequently, this artificial physiological color change and the process this artificial physiological color change is performed, is an important aspect of the present invention. Moreover, it is preferred that the color green indicates a healthy or beneficial or favorable or unharmful user state and that the color red indicates an unhealthy or unfavorable or harmful user state while the artificial physiological color change between these two extreme appearances of the visualized virtual agent is performed by a flowing change through the spectral colors from green over yellow and orange to red or the other way round with several or a plurality of shades in between.

Thus, the artificial physiological color change is defined as a flowing and dot-wise or pixel-wise or color-unit-wise change in color distributed over the whole shape of the visualized virtual agent.

Or the artificial physiological color change is defined as a flowing and dot-wise or pixel-wise or color-unit-wise change in color distributed over the whole shape of the visualized virtual agent while the artificial physiological color change is not spontaneous.

Or the artificial physiological color change is defined as a flowing and dot-wise or pixel-wise or color-unit-wise change in color distributed over the whole shape of the visualized virtual agent, wherein the color changes between green and red along the spectral colors. Preferably between the colors green and red at least 4, preferably 6, more preferably 8, more preferably 10 color nuances are present and have to be passed by the artificial physiological color change process, i.e. each dot or pixel or color-unit has to pass through each color in between green and red. Therefore, the visualized virtual agent preferably appears never in one single color, i.e. single-colored, and is always multi-colored or poly-colored and might appear in amicable, friendly, or supportive shape and/or design or in a dangerous, frightening, or noxious shape and/or design.

The term "artificial physiological color change response" as described herein generally relates to a provision of a visual response of a visualized virtual agent, which may be generated in form of an at least in part color change of a visualized virtual agent. The artificial physiological color change response as described herein thus relates to a computer-implemented method for generating of a visualized virtual agent providing an artificial physiological color change response to a user, wherein a visualized virtual agent may be configured to generate at least in part a color change of the visualized virtual agent based on user-specific parameter, which may be captured via technical integral components of a computing system or computing device or via technical external components connected to said computing system or computing device. The technical integral components and the technical external components may include one or more sensors. Preferably user-specific data for at least one user-specific parameter are acquired using at least one sensor. Thus, the artificial physiological color change response relates so to speak to a color change of the "skin" of a visualized virtual agent, for example, in case the visualized virtual agent is represented or rendered in form of an embodied virtual agent comprising a virtual body, like a body of a human or an animal. The artificial physiological color change response generated by the visualized virtual agent may depend on user-specific parameter, for example, on activity data of a user and/or physio-psychological data of user. Thus, the visualized virtual agent may provide an artificial physiological color change response to a user in connection with activity data of a user and/or physio-psychological data of a user. Preferably, the artificial physiological color change response generated by the visualized virtual agent may depend on at least one user-specific parameter, wherein user-specific data for the at least one user-specific parameter may be acquired using a sensor, for example, by acquiring activity data of a user using a sensor and/or acquiring physio-psychological data of user using a sensor. Thus, the visualized virtual agent may provide an artificial physiological color change response to a user in connection with the acquired activity data of a user and/or the acquired physio-psychological data of a user. The visualized virtual agent therefore may be configured to provide an artificial physiological color change response to a user in connection with activity data of a user and/or physio-psychological data of a user which may be monitored over time, in real time or in near real time, wherein the at least in part generated color change of the visualized virtual agent may depend on monitored changes of the activity data of a user and/or monitored changes of physio-psychological data of a user and thus may depend on monitored and determined changes of the acquired activity data of a user and/or the acquired physio-psychological data of a user. Thus, the artificial physiological color change response of the visualized virtual agent may be generated to reflect the monitored and/or the acquired changes of the activity data of a user and/or the physio-psychological data of a user. The visualized virtual agent therefore may provide an artificial physiological color change response in such a way like if the user would have the abilities of changing the color of his skin to reflect a condition through color change signals, like for example a chameleon is able to do so.

Thus, the present invention further relates to a visualized virtual agent configured to monitor over time, preferably in real-time or near real-time activity data of a user and/or physio-psychological data of a user by at least one sensor and configured to provide a visual response to a user, wherein the visualized virtual agent is configured to provide an artificial physiological color change response to a user for at least one visualized virtual agent state and/or for a current state of the user, wherein the at least one visualized virtual agent state and/or the current state of the user is determined on the basis of the activity data of the user and/or of the physio-psychological data of the user; wherein the visualized virtual agent is configured to adapt the artificial physiological color change response to monitored changes of the activity data of the user and/or the physio-psychological data of the user, wherein the adaption of the artificial physiological color change response comprises at least in part a color change of the visualized virtual agent for the at least one visualized virtual agent state and/or the current state of the user.

The visualized virtual agent of the present invention therefore may be configured to provide an artificial physiological color change response to a user on the basis of activity data of a user and/or physio-psychological data of a user in a way similar to a real species having the ability of changing the skin color to provide a physiological color change response to his environment. For example, chameleons have two superimposed layers within their skin that control their color and thermoregulation. The top layer contains a lattice of guanine nanocrystals, and by exciting this lattice the spacing between the nanocrystals can be manipulated, which in turn affects which wavelengths of light are reflected and which are absorbed. Exciting the lattice increases the distance between the nanocrystals and the skin reflects longer wavelengths of light. Thus, in a relaxed state the crystals reflect blue and green, but in an excited state the longer wavelengths such as yellow, orange, green, and red are reflected. The skin of a chameleon also contains some yellow pigments, which combined with the blue reflected by a relaxed crystal lattice results in the characteristic green color, which is common in many chameleons in their relaxed state.

The term "visualized virtual agent" as described herein generally relates to computer readable instructions that may be provided with and executed on an electronic device, comprising a memory and one or more processor, such as a personal computer or such as a wearable electronic device like a mobile phone e.g. a smart phone or like a smart watch. The visualized virtual agent of the present invention may be suitable to be implemented with various electronic devices or may be configured to connect to various electronic devices. The visualized virtual agent may comprise common functionalities of visualized virtual agents known in the art like may be configured to answer questions or to provide requested information. The visualized virtual agent may be configured to communicate with a user. The visualized virtual agent may be configured to obtain interaction context of a user, like characteristics of a user's speech, the identity of a user, the expression and gestures of a user. The visualized virtual agent may be configured to provide gestures, facial expressions and speech of the visualized virtual agent to enable the imitation of a face-to-face communication with users. The visualized virtual agent may be configured to express emotions or mood of the visualized virtual agent. The visualized virtual agent may be configured to provide visual changes and/or verbal instructions of the visualized virtual agent, thus the visualized virtual agent may be configured to provide visual and/or audible behavioral responses to a user. The visualized virtual agent may be configured to observe, analyze and respond to user's requests or to observe, analyze and respond to monitored user-specific parameter. The visualized virtual agent may be a guide, like a health guide, a personal coach, a personal agent, a personal assistant, a personal trainer, an advisor, like a health advisor, and/or a personal companion of a user. The visualized virtual agent may be configured to connect to a network and/or to a server, like a client server or a cloud server. The visualized virtual agent may be configured to access one or more databases. The visualized virtual agent may be configured to provide information or requested data, which may be obtained from one or more databases. The visualized virtual agent may be configured to access a third party service.

The visualized virtual agent may be configured to provide a visual response to a user, wherein the visualized virtual agent may be further configured to provide an artificial physiological color change response to a user on the basis of user-specific parameter, wherein the visualized virtual agent may be configured to acquire user-specific data for at least one user-specific parameter using at least one sensor, the user-specific parameter comprising activity data of the user and/or physio-psychological data of the user, and wherein the artificial physiological color change response may be provided in response to monitored changes of the acquired user-specific data for the at least one user-specific parameter of the activity data of the user and/or the physio-psychological data of the user, the artificial physiological color change response comprising at least in part a color change of the visualized virtual agent.

Referring now to FIG. 1 a visualized virtual agent system 100 for providing and operating a visualized virtual agent according to an embodiment of the present invention will be described. The system 100 includes an electronic device 101 comprising one or more processor(s) 108 and memory 109. The electronic device includes visualized virtual agent platform 102. The electronic device 101 may be any suitable computing device configured for generating the visualized virtual agent of the present invention, including but not limited to a smartphone, smart glasses, a smart watch a laptop, a computer, a tablet, etc. The electronic device 101 preferably relates to an electronic device used by the user. The electronic device 101 may include a display device 107 configured to display the visualized virtual agent. The electronic device 101 may be connected to one or more display devices 107 configured to display the visualized virtual agent. The electronic device 101 may be connected or may include one or more sensors 104. The sensors 104 may collect sensor data and may provide and transmit the sensor data to the user-specific parameter monitoring component 105 of the visualized virtual agent platform 102. The user-specific parameter monitoring component 105 is configured to monitor over time, preferably in real-time or near real-time, one or more user-specific parameter of the user, wherein user-specific data for at least one user-specific parameter are acquired by at least one sensor 104. The user-specific parameter monitoring component 105 is configured to monitor user-specific data for the one or more user-specific parameter. The user-specific parameter monitoring component 103 may be configured to store the acquired and/or monitored user-specific data. The user-specific parameter monitoring component 103 may be configured to transmit the acquired and/or monitored user-specific data to one or more databases or one or more servers. The user-specific parameters comprise activity data of a user and/or physio-psychological data of a user. The visualized virtual agent platform 102 further includes a user-specific data analysis component 103 configured for analyzing the user-specific data collected from the one or more sensor(s) 104 and monitored by the user-specific data monitoring component 105. The user-specific data analysis component 103 is configured to generate instructions for the visualized virtual agent rendering component 106 based on the analyzed user-specific data. Based on the received instructions the visualized virtual agent rendering component 106 may be configured to render and provide the artificial physiological color change response to the user by through the one or more display devices 107. The electronic device may be further connected to a network 110, such as the Internet. One or more databases 111 and/or one or more servers 112 may be connected to the network 110. The electronic device 101 may be configured to transmit data to the databases 111 and/or servers 112 through the network 110. The electronic device 101 may receive data from the databases 111 and/or servers 112 through the network 110. One or more of the components of the visualized virtual agent platform 102 may be implemented in the servers 112. For example, the user-specific data analysis component 103 may be implemented in servers 112 and the electronic device may be configured to transmit the user-specific data monitored by the user-specific parameter monitoring component 105 to the servers 112 through the network 210. The user-specific data analysis component 103 may be configured to analyze the received user-specific data and may be configured to transmit instruction to the visualized virtual agent rendering component 106 through network 110. As shown in FIG. 1 one or more electronic devices 113, 114 may be also connected to the network 110. The one or more electronic device may relate to additional electronic devices of the user. The one or more electronic devices 113, 114 may comprise one or more display devices. The electronic devices 113, 114 may be any suitable computing devices for providing or rendering the visualized virtual agent of the present invention, including but not limited to a smartphone, smart glasses, a smart watch a laptop, a computer, a tablet, etc. Thus, the instructions of the user-specific data analysis component 103 or the visualized virtual agent rendering component 106 may be transmitted to the one or more electronic devices 113, 114 for rendering the visualized virtual agent for providing the artificial physiological color change response to the user.

The visualized virtual agent may be configured to provide a visual response to a user, wherein the visualized virtual agent may be further configured to provide an artificial physiological color change response to a user on the basis of user-specific parameter, wherein the visualized virtual agent may be configured to acquire user-specific data for at least one user-specific parameter using at least one sensor, the user-specific parameter comprising activity data of the user and/or physio-psychological data of the user, and wherein the artificial physiological color change response may be provided in response to monitored changes of the acquired user-specific data for the at least one user-specific parameter of the activity data of the user and/or the physio-psychological data of the user, the artificial physiological color change response comprising at least in part a color change of the visualized virtual agent, wherein the visualized virtual agent may be further configured to provide the artificial physiological color change response to a user for at least one visualized virtual agent state and/or for a current state of the user, wherein the at least one visualized virtual agent state and/or the current state of the user is determined on the basis of the user-specific parameter, wherein for each determined visualized virtual agent state and/or determined current state of the user a selection of one or more user-specific parameter is determined to provide the artificial physiological color change response comprising at least in part a color change of the visualized virtual agent for the selection of one or more user-specific parameter for the determined visualized virtual agent state and/or determined current state of the user.

The visualized virtual agent of the present invention may be configured to monitor user-specific parameter, like activity data of a user and/or physio-psychological data of a user. Thus, the visualized virtual agent of the present invention may be configured to monitor user-specific parameter, like activity data of a user and/or physio-psychological data of a user over time, in real-time or in near real-time. The visualized virtual agent of the present invention may be configured to acquire user-specific data for at least one user-specific parameter of the activity data of a user and/or physio-psychological data or a user using at least one sensor. Thus, the visualized virtual agent of the present invention may be configured to acquire user-specific data for at least one user-specific parameter from the activity data of a user and/or physio-psychological data of a user using a sensor over time, in real-time or in near real-time. On the basis of the monitored and/or the acquired activity data of user and/or the monitored and/or the acquired physio-psychological data of a user the visualized virtual agent may be further configured to generate an artificial physiological color change response to user. Thus, the visualized virtual agent may be configured to analyze, to determine and to generate an artificial physiological color change response to a user in connection with the monitored and/or the acquired activity data of a user and/or the monitored and/or the acquired physio-psychological data of a user. The visualized virtual agent may be configured to provide an artificial physiological color change response to a user based on a selection of one or more user-specific parameter, thus a selection of one or more monitored and/or acquired activity data of a user and/or a selection of monitored and/or acquired specific physio-psychological data of a user. In one embodiment the visualized virtual agent may be configured to provide an artificial physiological color change response to a user based on one user-specific parameter. In another embodiment the visualized virtual agent may be configured to provide an artificial physiological color change response to a user based on at least two different user-specific parameters. In another embodiment the visualized virtual agent may be configured to provide an artificial physiological color change response to a user based on two different user-specific parameters. The visualized virtual agent may be configured to provide different artificial physiological color change responses to a user based on different selections of specific monitored and/or acquired activity data of a user and/or different selections of specific monitored and/or acquired physio-psychological data of a user. In one preferred embodiment the visualized virtual agent may be configured to provide an artificial physiological color change response to a user based on activity data of a user. In one preferred embodiment the visualized virtual agent may be configured to provide an artificial physiological color change response to a user based on acquired activity data of a user using at least one sensor. In one preferred embodiment the visualized virtual agent may be configured to provide an artificial physiological color change response to a user based on physio-psychological data of a user. In one preferred embodiment the visualized virtual agent may be configured to provide an artificial physiological color change response to a user based on acquired physio-psychological data of a user using at least one sensor. In another preferred embodiment the visualized virtual agent may be configured to provide an artificial physiological color change response to a user based on activity data of a user and on physio-psychological data of a user. In another preferred embodiment the visualized virtual agent may be configured to provide an artificial physiological color change response to a user based on acquired activity data of a user and on acquired physio-psychological data of a user using at least one sensor. The visualized virtual agent may be further configured to provide an artificial physiological color change response to a user based on activity data of a user and be further configured to provide an artificial physiological color change response to a user based on physio-psychological data of a user, wherein the visualized virtual agent may be configured to change between providing an artificial physiological color change response to a user based on activity data of a user and providing an artificial physiological color change response to a user based on physio-psychological data of a user. With other words the visualized virtual agent may provide different artificial physiological color change responses to a user at different points in time, wherein at the different points in time the artificial physiological color change responses may be based on activity data of user or physio-psychological data of a user or on activity data and physio-psychological data of a user.

Thus, the present invention further relates to a visualized virtual agent configured to provide a visual response to a user and configured to monitor over time one or more user-specific parameter of the user, wherein user-specific data for at least one user-specific parameter are acquired by at least one sensor, the user-specific parameter comprising activity data of the user and/or physio-psychological data of the user, wherein the visualized virtual agent is configured to provide an artificial physiological color change response to a user for at least one visualized virtual agent state and/or for a current state of the user, wherein the at least one visualized virtual agent state and/or the current state of the user is determined on the basis of the activity data of the user and/or of the physio-psychological data of the user; wherein the visualized virtual agent is configured to adapt the artificial physiological color change response to monitored changes of the activity data of the user and/or the physio-psychological data of the user, wherein the adaption of the artificial physiological color change response comprises at least in part a color change of the visualized virtual agent for the at least one visualized virtual agent state and/or the current state of the user.

With other words the present invention also relates to a visualized virtual agent configured to provide a visual response to a user and configured to monitor over time one or more user-specific parameter of the user, wherein user-specific data for at least one user-specific parameter are acquired by at least one sensor, the user-specific parameter comprising activity data of the user and/or physio-psychological data of the user, wherein the visualized virtual agent is configured to provide an artificial physiological color change response to a user for at least one visualized virtual agent state and/or for a current state of the user, wherein the at least one visualized virtual agent state and/or the current state of the user is determined on the basis of the one or more user-specific parameter of the user; wherein the visualized virtual agent is configured to adapt the artificial physiological color change response to monitored changes of the one or more user-specific parameter of the user, wherein the adaption of the artificial physiological color change response comprises at least in part a color change of the visualized virtual agent for the at least one visualized virtual agent state and/or the current state of the user.

In a preferred embodiment the visualized virtual agent is configured to provide the artificial physiological color change response based on a selection of one or more user-specific parameter. Preferably the selection of one or more user-specific parameter comprises at least two different user-specific parameters. Preferably user-specific data of at least one of the selected one or more user-specific parameter are acquired by the at least one sensor.

Thus, the present invention further relates to a visualized virtual agent configured to provide a visual response to a user and configured to monitor over time one or more user-specific parameter of the user, wherein user-specific data for at least one user-specific parameter are acquired by at least one sensor, the user-specific parameter comprising activity data of the user and/or physio-psychological data of the user, wherein the visualized virtual agent is configured to provide an artificial physiological color change response to a user for at least one visualized virtual agent state and/or for a current state of the user, wherein the at least one visualized virtual agent state and/or the current state of the user is determined on the basis of the activity data of the user and/or of the physio-psychological data of the user; wherein the visualized virtual agent is configured to adapt the artificial physiological color change response to monitored changes of the activity data of the user and/or the physio-psychological data of the user, wherein the adaption of the artificial physiological color change response comprises at least in part a color change of the visualized virtual agent for the at least one visualized virtual agent state and/or the current state of the user, wherein determining the current state of the user comprises determining a selection of one or more user-specific parameter as a basis for generating of the artificial physiological color change response to the user.

Referring now to FIG. 2 a visualized virtual agent system 200 for providing and operating a visualized virtual agent according to an embodiment of the present invention will be described. The system 200 includes an electronic device 201 comprising one or more processor(s) 208 and memory 209. The electronic device includes visualized virtual agent platform 202. The electronic device 201 may be any suitable computing device for generating the visualized virtual agent of the present invention, including but not limited to a smartphone, smart glasses, a smart watch a laptop, a computer, a tablet, etc. The electronic device preferably relates to an electronic device used by the user. The electronic device 201 may include a display device 207 configured for displaying the visualized virtual agent. The electronic device 201 may be connected to one or more display devices 207 configured for displaying the visualized virtual agent. The electronic device 201 may be connected or may include one or more sensors 204. The sensors 204 may collect sensor data and may provide and transmit the sensor data to the user-specific parameter monitoring component 205 of the visualized virtual agent platform 202. The user-specific parameter monitoring component 205 is configured to monitor over time, preferably in real-time or near real-time, one or more user-specific parameter of the user wherein user-specific data for at least one user-specific parameter are acquired by at least one sensor 204. The user-specific parameter monitoring component 205 is configured to monitor user-specific data for the one or more user-specific parameter. The user-specific parameters comprise activity data of a user and/or physio-psychological data of a user. The visualized virtual agent platform 202 further includes a user-specific data analysis component 203 configured for analyzing the user-specific data collected by the one or more sensors 207 and monitored by the user-specific parameter monitoring component 205. The user-specific data analysis component 203 further includes a user-specific parameter selection component 215. The user-specific parameter selection component 215 is configured to determine a selection of one or more user-specific parameter for generation of the artificial physiological color change response to the user based on the monitored and/or acquired user-specific data from user-specific parameter monitoring component 205. Based on the selection of one or more user-specific parameter determined by the user-specific parameter selection component 215 the user-specific parameter analysis component 203 is configured to analyze the user-specific data of the one or more user-specific parameter of the selection of one or more user-specific parameter. The user-specific data analysis component 203 is configured to generate instructions to the visualized virtual agent rendering component 206 based on the analyzed user-specific data of the selection of the one or more user-specific parameter. Based on the received instructions the visualized virtual agent rendering component 206 may be configured to render and to provide the artificial physiological color change response to the user through the one or more display devices 207. The electronic device may be further connected to a network 210, such as the Internet. One or more databases 211 and/or one or more servers 212 may be connected to the network 210. The electronic device 201 may be configured to transmit data to the databases 211 and/or servers 212 through the network 210. The electronic device 201 may receive data from the databases 211 and/or servers 212 through the network 210. One or more electronic device 213, 214 may be connected to the network 210. The one or more electronic device may relate to additional electronic devices of the user. The one or more electronic devices 213, 214 may comprise one or more display devices. The electronic devices 213, 214 may be any suitable computing devices for providing or rendering the visualized virtual agent of the present invention, including but not limited to a smartphone, smart glasses, a smart watch a laptop, a computer, a tablet, etc. Thus, the instructions of the user-specific data analysis component 203 or the visualized virtual agent rendering component 106 may be transmitted to the one or more electronic devices 213, 214 for rendering the visualized virtual agent for providing the artificial physiological color change response to the user.

Furthermore, it also may not be suitable to provide a visualized virtual agent configured to provide an artificial physiological color change response to a user by using the entire monitored user-specific parameter, like activity data of a user and/or physio-psychological data of a user for generating to the artificial physiological color change response. Thus, it may not be suitable that the entire monitored user-specific parameter, like the activity data a user and/or the physio-psychological data of a user are taken as the basis for determining and generating of an artificial physiological color change response to the user. For example, the visualized virtual agent may be configured to monitor location-data of a user, movement behavior of a user, sleeping behavior of a user, emotional state of a user and mood of a user. The location-data of a user, movement behavior of a user, sleeping behavior of a user, the emotional state of a user and the mood of the user may be monitored by acquiring said data by using at least one sensor. On the basis of said data and/or said acquired data the visualized virtual agent may be configured to analyze the monitored and/or the acquired user-specific data and to determine if the user is sleeping or if he is awake and is moving. In this example, the visualized virtual agent may be further configured to provide an artificial physiological color change response to a user based on the monitored location-data of a user, the monitored movement behavior of a user, the monitored sleeping behavior of a user, the monitored emotional state of a user and the monitored mood of a user. The visualized virtual agent may be further configured to provide an artificial physiological color change response to a user based on a selection of the monitored activity data of a user and/or the monitored physio-psychological data of a user. Thus, the provided at least in part artificial physiological color change response of the visualized virtual agent may be based on one or more specific parameter which means to a specific selection of the one or more monitored and/or acquired user-specific parameter. For example, it may not be suitable to provide an artificial physiological color change response to a user based on the monitored location-data of a user, the monitored movement behavior of the user, the monitored sleeping behavior of a user, the monitored emotional state of a user and the monitored mood of a user for times the user is sleeping. Thus, the visualized virtual agent may be configured to provide an artificial physiological color change response to a user based on, for example, solely the monitored sleeping behavior of a user for times the user is sleeping, wherein the sleeping behavior of the user may be preferably monitored by acquiring user-specific data in connection with the sleeping behavior by using at least one sensor, for example a sensor for monitoring sleep behavior of a user. Thus, the at least in part color change of the visualized virtual agent may be generated based on the monitored and/or the acquired sleeping behavior of a user for times the user is sleeping. At the times the user is awake and moving the visualized virtual agent may be further configured to provide, for example, an artificial physiological color change response to a user based on monitored location-data of a user, monitored movement behavior of a user, monitored emotional state of a user and monitored mood of a user. The location-data of a user, movement behavior of the user, emotional state of the user and mood of the user may be monitored by acquiring said user-specific data by using at least one sensor, for example a global positioning sensor (GPS), one or more cameras and/or one or more microphones. Nevertheless it may not be suitable that at the times the user is awake and moving the visualized virtual agent may provide an artificial physiological color change response based on all of said monitored and/or acquired data, which means the location-data of a user, movement behavior data of a user, emotional state data of a user and mood data of a user at the same time. For example, in the case the emotional state of a user and the mood of a user are monitored by acquiring emotional state data of a user and mood data of a user by using a camera and the user is moving around without being in the field of vision of said camera, the visualized virtual agent may be configured to provide an artificial physiological color change response solely based on the monitored location-data of a user, monitored movement behavior data of a user and not the monitored emotional state data of a user and monitored mood data of a user. In this example, it may be therefore be suitable if the visualized virtual agent would be configured to provide an artificial physiological color change response to a user on the basis of the emotional state of a user and the mood of a user at times the user is staying in active communication with the visualized virtual agent and thus in times the user is staying in the field of vision of said camera.

Thus, it may be advantageous if the visualized virtual agent may be further configured to initially determine a visualized virtual agent state and/or a current state of the user in order to determine an initial selection of suitable user-specific parameter, which may be particularly suitable to serve as a basis for generating of the artificial physiological color change response to a user. Thus, it may be advantageous if the visualized virtual agent may be further configured to initially determine a visualized virtual agent state and/or a current state of the user in order to determine an initial selection of one or more sensors which may be used to acquire user-specific data for one or more user-specific parameter, which may be particularly suitable to serve as a basis for generating of the artificial physiological color change response to a user.

The visualized virtual agent state and/or the current state of the user may be determined based on user-specific parameter, like activity data of a user and/or physio-psychological data of a user. With other words the visualized virtual agent may be configured to monitor, to collect and to analyze a large amount of data of a large amount of user-specific parameter, preferably by acquiring said data by using at least one sensor, for activity data of a user and/or physio-psychological data of a user and be further configured to determine an initial selection of one or more suitable user-specific parameter selected from the entire user-specific parameter in order to determine and provide a specific selection of one or more user-specific parameter, which may serve the basis for generating of an artificial physiological color change response to a user.

With other words, the visualized virtual agent may be configured to monitor, to collect and to analyze a plurality of data for a plurality of user-specific parameter for activity data of a user and/or physio-psychological data of a user and is configured to determine a current state of the user and/or a visualized virtual agent state based on the monitored, collected and analyzed plurality of data and is configured to determine a selection of one or more user-specific parameter selected from the entire user-specific parameter in order to provide a specific selection of one or more user-specific parameter as a basis for generating the artificial physiological color change response to the user.

Thus, the present invention further relates to a visualized virtual agent configured to provide a visual response to a user and configured to monitor over time one or more user-specific parameter of the user, wherein user-specific data for at least one user-specific parameter are acquired by at least one sensor, the user-specific parameter comprising activity data of the user and/or physio-psychological data of the user, wherein the visualized virtual agent is configured to provide an artificial physiological color change response to a user for at least one visualized virtual agent state and/or for a current state of the user, wherein the at least one visualized virtual agent state and/or the current state of the user is determined on the basis of the activity data of the user and/or of the physio-psychological data of the user; wherein the visualized virtual agent is configured to adapt the artificial physiological color change response to monitored changes of the activity data of the user and/or the physio-psychological data of the user, wherein the adaption of the artificial physiological color change response comprises at least in part a color change of the visualized virtual agent for the at least one visualized virtual agent state and/or the current state of the user, wherein the visualized virtual agent is configured to monitor, to collect and to analyze a plurality of data for a plurality of user-specific parameter for activity data of a user and/or physio-psychological data of a user and is configured to determine the current state of the user based on the monitored, collected and analyzed plurality of data and is configured to determine a selection of one or more user-specific parameter selected from the entire user-specific parameter in order to provide a specific selection of one or more user-specific parameter as a basis for generating the artificial physiological color change response to the user.

Thus, the visualized virtual agent of the present invention may be configured to provide an artificial physiological color change response to a user on the basis of a visualized virtual agent state. Thus, the visualized virtual agent may be further configured to determine a visualized virtual agent state. The visualized virtual agent state may be determined on the basis of user-specific parameter, like activity data of a user and/or physio-psychological data of a user. The user-specific data for at least one user-specific parameter, like activity data of a user and/or physio-psychological data of a user may be acquired by using at least one sensor. Therefore the visualized virtual agent may be configured to determine a visualized virtual agent state on the basis of activity data of a user and/or physio-psychological data of a user. The "visualized virtual agent state" as described herein generally relates to determining of a specific activity of a user and/or a specific physio-psychological behavior of a user in order to determine a selection of user-specific parameter which may serve a basis for generating of an artificial physiological color change response to a user. In one preferred embodiment the visualized virtual agent state may be determined on the basis of one or more activity data of a user. In another preferred embodiment the visualized virtual agent state may be determined on the basis of one or more physio-psychological data of a user. In another preferred embodiment the visualized virtual agent state may be determined on the basis of one or more activity data of a user and of one or more physio-psychological data of a user.

An example of a visualized virtual agent state may relate to times the user is staying in active communication with the visualized virtual agent. Active communication with a visualized virtual agent relates to times the user is requesting specific information or the like, or to times the user is actively speaking with the visualized virtual agent, preferably to times the user may have eye contact with the visualized virtual agent. Thus, the visualized virtual agent state may refer to a period of time wherein the visualized virtual agent actively provides requested information in response to a question of a user. Another visualized virtual agent state may refer to times wherein the visualized virtual agent is in a passive or monitoring mode. A passive and monitoring mode may refer to times the user is not staying in active communication with the visualized virtual agent. A passive or monitoring visualized virtual agent state may further relate to a stand-by mode or idle mode of an electronic device. Thus, the visualized virtual agent may be configured to determine a visualized virtual agent state which may relate to an active communication visualized virtual agent state or a passive or monitoring visualized virtual agent state. In this example, the visualized virtual agent state may be determined by acquiring data by using at least one camera. For example by using an integral camera of the electronic device where the visualized virtual agent may be stored in a memory and may be executed by one or more processors. The visualized virtual agent may be further configured to provide different artificial physiological color change responses to a user for different determined visualized virtual agent states. For example, the visualized virtual agent may be configured to provide a different artificial physiological color change response to a user in an active communication visualized virtual agent state then in a passive or monitoring visualized virtual agent state. Thus, the visualized virtual agent may be configured to monitor and to analyze activity data of a user and/or the physio-psychological data of a user over time, in real-time or in near-real time and be further configured to determine a visualized virtual agent state based on the monitored activity data of a user and/or physio-psychological data of a user. After a visualized virtual agent state has been determined by the visualized virtual agent, the visualized virtual agent may be further configured to continue to monitor and to analyze activity data of a user and/or physio-psychological data of a user over time, in real time or in near-real time and be further configured to recognize a change of the visualized virtual agent state based on said monitored and analyzed activity data of a user and/or physio-psychological data of a user. Thus, after determining a first visualized virtual agent state the visualized virtual agent may be further configured to determine a second visualized virtual agent state based on a monitored change of activity data of a user and/or physio-psychological data of a user and thus based on a monitored change of the acquired activity data of a and/or physio-psychological data of a user, for example acquired by using one or more cameras. The visualized virtual agent may be configured to provide an artificial physiological color change response to a user based on a first selection of one or more user-specific parameter from the activity data of a user and/or the physio-psychological data of a user for a first visualized virtual agent state and be further configured to provide an artificial physiological color change response to a user based on a second selection of one or more user-specific parameter from the activity data of a user and/or physio-psychological data of a user for a second visualized virtual agent state. The visualized virtual agent may be further configured to change between the first visualized virtual agent state and the second visualized virtual agent state. Preferably the visualized virtual agent may be configured to determine at least one visualized virtual agent state.

The visualized virtual agent may be configured to provide same or different artificial physiological color change responses to a user for different determined visualized virtual agent states. Thus the visualized virtual agent may be configured to provide artificial physiological color change responses for different visualized virtual agent states either based on the same selection of the same one or more user-specific parameter from the activity data of a user and/or physiological data of a user or may be based on different selections of one or more user-specific parameter from the activity data of a user and/or from the physio-psychological data of a user. For example, the visualized virtual agent may be configured to provide an artificial physiological color change response to a user based on a lower number of user-specific parameter for a passive or monitoring visualized virtual agent state then for an active communication visualized virtual agent state.

Thus, in one embodiment of the present invention the visualized virtual agent may be configured to provide an artificial physiological color change response to a user for at least one visualized virtual agent state, wherein the visualized virtual agent may be configured to provide a visual response to the user, wherein the at least one visualized virtual agent state may be determined on the basis of activity data of the user and/or physio-psychological data of a user and wherein the visualized virtual agent may be further configured to adapt the visual response to monitored changes of activity data of the user and/or physio-psychological data of the user, wherein the adaption of the visual response comprises at least in part a color change of the visualized virtual agent for the at least one visualized virtual agent state.

Thus, in one embodiment of the present invention the visualized virtual agent configured to provide a visual response to the user may be further configured to provide an artificial physiological color change response to a user for at least one visualized virtual agent state, wherein the at least one visualized virtual agent state is determined on the basis of user-specific parameter, wherein the user-specific parameter comprise activity data of the user and/or physio-psychological data of a user, wherein user-specific data of at least one user-specific parameter are acquired by using at least one sensor, and wherein the artificial physiological color change response is provided in response to monitored changes of the acquired user-specific data for the at least one user-specific parameter, the artificial physiological color change response comprising at least in part a color change of the visualized virtual agent for the at least one visualized virtual agent state.

Thus, the present invention further relates to a visualized virtual agent configured to provide a visual response to a user and configured to monitor over time one or more user-specific parameter of the user, wherein user-specific data for at least one user-specific parameter are acquired by at least one sensor, the user-specific parameter comprising activity data of the user and/or physio-psychological data of the user, wherein the visualized virtual agent is configured to provide an artificial physiological color change response to a user for at least one visualized virtual agent state and/or for a current state of the user, wherein the at least one visualized virtual agent state and/or the current state of the user is determined on the basis of the activity data of the user and/or of the physio-psychological data of the user; wherein the visualized virtual agent is configured to adapt the artificial physiological color change response to monitored changes of the activity data of the user and/or the physio-psychological data of the user, wherein the adaption of the artificial physiological color change response comprises at least in part a color change of the visualized virtual agent for the at least one visualized virtual agent state and/or the current state of the user, wherein determining the visualized virtual agent state comprises determining a selection of one or more user-specific parameter as a basis for generating of the artificial physiological color change response to the user and wherein the visualized virtual agent is configured to provide an artificial physiological color change response to a user based on a first selection of one or more user-specific parameter from the activity data of a user and/or the physio-psychological data of a user for a first visualized virtual agent state and be further configured to provide an artificial physiological color change response to a user based on a second selection of one or more user-specific parameter from the activity data of a user and/or physio-psychological data of a user for a second visualized virtual agent state, wherein the visualized virtual agent is configured to change between the first visualized virtual agent state and the second visualized virtual agent state.

Preferably the first visualized virtual agent state comprises an active communication visualized virtual agent state and the second visualized virtual agent state comprises a passive or monitoring visualized virtual agent state.

Besides determining a visualized virtual agent state the visualized virtual agent may be further configured to determine a current state of a user or a state of a user based on activity data of a user and/or physio-psychological data of a user. The visualized virtual agent may be configured to provide an artificial physiological color change response to a user on the basis of a current state of a user. Thus, the visualized virtual agent may be configured to determine a current state of the user in order to determine a selection of one or more user-specific parameter, which may serve the basis for generating of the artificial physiological color change response. The current state of a user may be determined by acquiring user-specific data for at least on user-specific parameter, the user-specific parameter may comprise activity data of a user and/or physio-psychological data of a user, by using at least one sensor. The visualized virtual agent may be further configured to determine a state of a user. The current state of the user may be determined on the basis of user-specific parameter, like activity data of a user and/or physio-psychological data of a user. Therefore the visualized virtual agent may be configured to determine a current state of the user on the basis of activity data of a user and/or physio-psychological data of a user. The "current state of the user" as described herein relates to activity data of a user or physio-psychological data of a user like to the mood or emotions of a user or like to specific activities of the user like physical training or eating or relaxing and the like. Thus, the visualized virtual agent may be configured to provide an artificial physiological color change response to a user on the basis of a current behavior and/or the current physiological state and/or the current mental state and/or a current medical state of the user. In one embodiment the visualized virtual agent may be configured to provide an artificial physiological color change response on the basis of a current state of a user which may be determined on the basis of activity data of a user. In another embodiment the visualized virtual agent may be configured to provide an artificial physiological color change response to the user on the basis of a current state of a user which may be determined on the basis of physio-psychological data of a user. In another embodiment the current state of a user may be determined on the basis of activity data of a user and physio-psychological data of a user. Activity data of a user may include current activities of a user like for example what the user is doing, like sleeping, eating, doing physical exercises etc. For example, when a user is running, the current state of a user may refer to a running state of the user. The visualized virtual agent may be configured to provide a visual response comprising at least in part a color change of the visualized virtual agent depending on monitored changes of the monitored activity data of a user and/or monitored physio-psychological data of a user for a determined current state of a user. For example, when the visualized virtual agent has determined a running state of a user, for times the activity data of the user indicate that the user is running, wherein the activity data may be acquired by using a sensor like a GPS tracker step counting sensor, the visualized virtual agent may be further configured to acquire the user-specific data from for example, the GPS tracker or step counting sensor and may be therefore configured to monitor and to automatically determine if the user stops running. The visualized virtual agent may be further configured to acquire physio-psychological data from the user from one or more sensors during the activity of the user. For example, in connection with the speed, the duration, the heart rate etc. The virtual visualized agent may be configured to automatically recognize, thus to determine if one of these physio-psychological data changes, like for example if the user slows down, or if the heart rate increases or decreases. In this example, it may be suitable that for the running state of the user, the visualized virtual agent may be configured to provide an artificial physiological color change response to a user based on the monitored speed data of a user and monitored heart rate data of a user, which may be acquired by using for example a GPS tracker and a pulse rate sensor.

As an example a current state of a user may relate to times the user is running. Thus, a running state of a user may refer to a period of time when the user is running. Another example of a current state of a user may refer to times when the user is relaxing on his couch. Thus, a relaxing state of a user may refer to a period of time when the user is relaxing on his coach. Thus, the visualized virtual agent may be configured to determine a current state of a user which may relate to a running state of a user or a relaxing state of a user. The visualized virtual agent may be further configured to provide different artificial physiological color change responses to a user for different states of a user, thus for different current states of a user. For example, the visualized virtual agent may be configured to provide a different artificial physiological color change response to a user for a running state of a user then for a relaxing state of user. Thus, the visualized virtual agent may be configured to monitor and to analyze activity data of a user and/or the physio-psychological data of a user over time, in real-time or in near-real time and be further configured to determine a state of a user, preferably a current state of a user based on the monitored activity data of a user and/or physio-psychological data of a user. After the current state of the user has been determined by the visualized virtual agent, the visualized virtual agent may be further configured to continue to monitor and to analyze activity data of a user and/or physio-psychological data of a user over time, in real time or in near-real time and be further configured to automatically recognize and thus to determine a change of the current state of the user based on the monitored and/or acquired and analyzed activity data of a user and/or physio-psychological data of a user. Thus, after determining a first state of a user the visualized virtual agent may be further configured to determine a second state of a user based on a monitored change of activity data of a user and/or physio-psychological data of a user. The visualized virtual agent may be configured to provide an artificial physiological color change response to a user based on a first selection of one or more user-specific parameter of activity data of a user and/or physio-psychological data of a user for a first state of a user and be further configured to provide an artificial physiological color change response to a user based on a second selection of one or more user-specific parameter of activity data of a user and/or physio-psychological data of a user for a second state of a user. The visualized virtual agent may be further configured to change between the first state of the user and the second state of a user. Preferably the visualized virtual agent may be configured to determine at least one state of the user. Preferably the visualized virtual agent may be configured to determine a current state of a user over time, in real time or near real time.

The visualized virtual agent may be configured to provide same or different artificial physiological color change responses to a user for different determined states of a user. Thus the visualized virtual agent may be configured to provide artificial physiological color change responses for different states of a user either based on the same selection of one or more user-specific parameter of the activity data of a user and/or physiological data of a user or may be based on different selections of one or more user-specific parameter of the activity data of a user and/or physio-psychological data of a user. For example, the visualized virtual agent may be configured to provide an artificial physiological color change response to a user based on a lower number of user-specific parameter for a relaxing state of a user then for a running state of a user.

Thus, in one embodiment of the present invention the visualized virtual agent may be configured to provide an artificial physiological color change response to a user for at least one state of a user, preferably a current state of a user, wherein the visualized virtual agent may be configured to provide a visual response to the user, wherein the at least one state of the user, preferably the current state of the user may be determined on the basis of activity data of the user and/or physio-psychological data of a user and wherein the visualized virtual agent may be further configured to adapt the visual response to monitored changes of activity data of the user and/or physio-psychological data of the user, wherein the adaption of the visual response comprises at least in part a color change of the visualized virtual agent for the at least one state of the user, preferably current state of the user.

Thus, in one embodiment of the present invention the visualized virtual agent configured to provide a visual response to the user may be further configured to provide an artificial physiological color change response to a user for at least one state of a user, preferably a current state of a user, wherein the at least one state of the user, preferably the current state of the user is determined on the basis of user-specific parameter, wherein the user-specific parameter comprise activity data of the user and/or physio-psychological data of a user, wherein user-specific data of at least user-specific parameter are acquired by using at least one sensor, and wherein the artificial physiological color change response is provided in response to monitored changes of the acquired user-specific data for the at least one user-specific parameter, the artificial physiological color change response comprising at least in part a color change of the visualized virtual agent for the at least one visualized virtual agent state.

Thus, in one embodiment of the present invention the visualized virtual agent may be configured to provide an artificial physiological color change response to a user for at least one state of a user, preferably a current state of a user, wherein the visualized virtual agent may be configured to provide a visual response to the user, wherein the at least one state of the user, preferably the current state of the user may be determined on the basis of a current behavior and/or a current physiological state and/or a current mental state and/or a current medical state of the user and wherein the visualized virtual agent may be further configured to adapt the visual response to monitored changes of the current behavior and/or the current physiological state and/or the current mental state and/or the current medical state of the user, wherein the adaption of the visual response comprises at least in part a color change of the visualized virtual agent for the at least one state of the user, preferably current state of the user.

Thus, the present invention further relates to a visualized virtual agent configured to provide a visual response to a user and configured to monitor over time one or more user-specific parameter of the user, wherein user-specific data for at least one user-specific parameter are acquired by at least one sensor, the user-specific parameter comprising activity data of the user and/or physio-psychological data of the user, wherein the visualized virtual agent is configured to provide an artificial physiological color change response to a user for a current state of the user, wherein the current state of the user is determined on the basis of the activity data of the user and/or of the physio-psychological data of the user; wherein the visualized virtual agent is configured to adapt the artificial physiological color change response to monitored changes of the activity data of the user and/or the physio-psychological data of the user, wherein the adaption of the artificial physiological color change response comprises at least in part a color change of the visualized virtual agent for the current state of the user.

Thus, the present invention further relates to a visualized virtual agent configured to provide a visual response to a user and configured to monitor over time one or more user-specific parameter of the user, wherein user-specific data for at least one user-specific parameter are acquired by at least one sensor, the user-specific parameter comprising activity data of the user and/or physio-psychological data of the user, wherein the visualized virtual agent is configured to provide an artificial physiological color change response to a user for at least one visualized virtual agent state and/or for a current state of the user, wherein the at least one visualized virtual agent state and/or the current state of the user is determined on the basis of the activity data of the user and/or of the physio-psychological data of the user; wherein the visualized virtual agent is configured to adapt the artificial physiological color change response to monitored changes of the activity data of the user and/or the physio-psychological data of the user, wherein the adaption of the artificial physiological color change response comprises at least in part a color change of the visualized virtual agent for the at least one visualized virtual agent state and/or the current state of the user, wherein the visualized virtual agent is configured to provide an artificial physiological color change response to a user based on a first selection of one or more user-specific parameter from the activity data of a user and/or the physio-psychological data of a user for a first state of a user and be further configured to provide an artificial physiological color change response to a user based on a second selection of one or more user-specific parameter from the activity data of a user and/or physio-psychological data of a user for a second state of a user, wherein the visualized virtual agent is configured to change between the first state of the user and the second state of the user.

Referring now to FIG. 3 a visualized virtual agent system 300 for providing and operating a visualized virtual agent according to an embodiment of the present invention will be described. The system 300 includes an electronic device 301 comprising one or more processor(s) 308 and memory 309. The electronic device includes visualized virtual agent platform 302. The electronic device 301 may be any suitable computing device for generating the visualized virtual agent of the present invention, including but not limited to a smartphone, smart glasses, a smart watch a laptop, a computer, a tablet, etc. The electronic device preferably relates to an electronic device used by the user. The electronic device 301 may include a display device 307 configured for displaying the visualized virtual agent. The electronic device 301 may be connected to one or more display devices 307 configured for displaying the visualized virtual agent. The electronic device 301 may be connected or may include one or more sensors 304. The sensors 304 may collect sensor data and may provide and transmit the sensor data to the user-specific parameter monitoring component 305 of the visualized virtual agent platform 302. The user-specific parameter monitoring component 305 is configured to monitor over time one or more user-specific parameter, wherein user-specific data for at least one user-specific parameter are acquired by at least one sensor 304. The user-specific parameter monitoring component 305 is configured to monitor user-specific data for the one or more user-specific parameter of the user. The user-specific parameters comprise activity data of a user and/or physio-psychological data of a user. The visualized virtual agent platform 302 further includes a user-specific data analysis component 303 configured for analyzing the user-specific data collected by the sensors 304 and monitored by the user-specific parameter monitoring component 305. The user-specific data analysis component 303 further includes a user-specific parameter selection component 315. The user-specific parameter selection component 315 is configured to determine a selection of one or more user-specific parameter for generation of the artificial physiological color change response to the user based on the monitored and/or acquired user-specific data for the one or more user-specific parameter of the user from the user-specific parameter monitoring component 305. The user-specific data analysis component 303 further includes a current state of the user determination component 316 configured to determine a current state of the user based on activity data of a user and/or physio-psychological data of the user monitored and/or acquired by the user-specific parameter monitoring component 305. After determining the current state of the user by the current state of the user determination component 316 the current state of the user is provided to the user-specific parameter selection component 315. The user-specific parameter selection component 315 then determines a selection of one or more user-specific parameter for generation of the artificial physiological color change response to the user based on the determined current state of the user. Based on the determined selection of one or more user-specific parameter by the user-specific parameter selection component 315 the user-specific parameter analysis component 303 is configured to analyze the user-specific data for the one or more user-specific parameter of the selection of one or more user-specific parameter monitored by the user-specific parameter monitoring component. The user-specific data analysis component 303 is configured to generate instructions for the visualized virtual agent rendering component 306 based on the analyzed user-specific data of the selection of the one or more user-specific parameter. Based on the received instructions the visualized virtual agent rendering component 306 may be configured to render and provide the artificial physiological color change response to the user through the one or more display devices 307. The electronic device may be further connected to a network 310, such as the Internet. One or more databases 311 and/or one or more servers 312 may be connected to the network 310. The electronic device 301 may be configured to transmit data to the databases 311 and/or servers 312 through the network 310. The electronic device 301 may receive data from the databases 311 and/or servers 312 through the network 310. One or more electronic device 313, 314 may be connected to the network 310. The one or more electronic device may relate to additional electronic devices of the user. The one or more electronic devices 313, 314 may comprise one or more display devices. The electronic devices 313, 314 may be any suitable computing devices for providing or rendering the visualized virtual agent of the present invention, including but not limited to a smartphone, smart glasses, a smart watch a laptop, a computer, a tablet, etc. Thus, the instructions of the user-specific data analysis component 303 or the visualized virtual agent rendering component 306 may be transmitted to the one or more electronic devices 313, 314 for rendering the visualized virtual agent for providing the artificial physiological color change response to the user.

The visualized virtual agent may be further configured to determine a visualized virtual agent state and a current state of the user. The visualized virtual agent may be configured to provide visual responses comprising at least in part a color change of the visualized virtual agent to a user on the basis of a visualized virtual agent state and a current state of a user. The visualized virtual agent may be configured to provide an artificial physiological color change response to a user on the basis of a visualized virtual agent state and a current state of a user in order to determine a selection of one or more user-specific parameter, which may serve a basis for generating an artificial physiological color change response to a user. For example, the visualized virtual agent may be configured to change between two visualized virtual agent states, for example, between a passive or monitoring visualized virtual agent state and an active communication visualized virtual agent state. The passive or monitoring visualized virtual agent state and/or the active communication visualized virtual agent state may be determined on the basis of user-specific data acquired via speech recognition by using at least one sensor, for example at least one microphone, for example if the user is speaking with the visualized virtual agent or if the user is staying in eye contact with the visualized virtual agent, which may be determined on the basis of acquired user-specific data using at least one camera. The current state of the user may, for example, refer to a running state of the user or a relaxing state of a user. The running behavior or the relaxing behavior of a user may be determined and analyzed through monitored activity data of a user and/or physio-psychological data of a user, which may be monitored with at least one sensor, and wherein the visualized virtual agent may acquire the user-specific data of the at least one sensor. The visualized virtual agent may be configured to provide different artificial physiological color change responses to a user on the basis of different specific selections of one or more user-specific parameter of activity data of a user and/or physio-psychological data of a user for different visualized virtual agent states and/or for different states of a user. Thus, the visualized virtual agent may be configured to provide different artificial physiological color change responses to a user on the basis of a first selection of one or more user-specific parameter of activity data of user and/or physio-psychological data of a user for a first visualized virtual agent state, for example active communication visualized virtual agent state, and on the basis of a second selection of one or more user-specific parameter of activity data of a user and/or physio-psychological data of a user for a second visualized virtual agent state, for example passive or monitoring visualized virtual agent state. The visualized virtual agent may be configured to provide different artificial physiological color change responses to a user on the basis of a first selection of one or more user-specific parameter of activity data of user and/or physio-psychological data of a user for a first state of a user, for example running state of a user, and on the basis of a second selection of one or more user-specific parameter of activity data of a user and/or physio-psychological data of a user for a second state of a user, for example relaxing state of a user. In the case the visualized may be configured to provide an artificial physiological color change response to a user on the basis of at least one visualized virtual agent state and at least one state of the user, the visualized virtual agent state may be for example configured to provide different artificial physiological color change responses to a user on the basis of a first selection of one or more user-specific parameter for a first state of a user, like running state of a user in combination with a first visualized virtual agent state, like active communication visualized virtual agent state and on the basis of a second selection of one or more user-specific parameter for a first state of a user, like running state of a user in combination with a second visualized virtual agent state, like passive or monitoring visualized virtual agent state. The visualized virtual agent state may be for example further configured to provide different artificial physiological color change responses to a user on the basis of a first selection of one or more user-specific parameter for a second state of a user, like relaxing state of a user in combination with a first visualized virtual agent state, like active communication visualized virtual agent state and on the basis of a second selection of one or more user-specific parameter for a second state of a user, like relaxing state of a user in combination with a second visualized virtual agent state, like passive or monitoring visualized virtual agent state. With other words the visualized virtual agent may be configured to provide different artificial physiological color change responses to a user for each state of a user and for each visualized agent state and combinations thereof. The visualized virtual agent preferably may be configured to change between each state of a user and each visualized virtual agent state in order to provide artificial physiological color change responses in the most suitable manner for each situation of a user. Thus, the visualized virtual agent configured to provide a visual response to a user, which is further configured to provide an artificial physiological color change response to a user may be configured to provide automatically the most suitable artificial physiological color change response to a user for every situation of a user over time, in real time or near real time.

In another exemplary embodiment the visualized virtual agent may be in a passive or monitoring visualized virtual agent state and may monitor and analyze changes of the mood and/or emotional state of a user based on a specific selection of one or more monitored activity data and/or monitored physio-psychological data, which may be preferably monitored by acquiring user-specific data for the mood and/or emotional state by using at least one sensor. The visualized virtual agent may be configured to provide an artificial physiological color change response to a user based on said specific selection of the one or more monitored activity data and/or one or more monitored physio-psychological data of the user. Thus, for a specific visualized virtual agent state the visualized virtual agent may be configured to generate visual signals representing the visualized virtual agent to provide an artificial physiological color change response to a user and be configured to generate the visualized virtual agent by monitoring and analyzing a specific selection of monitored activity data of the user and/or monitored physio-psychological data of the user. By changing into another visualized virtual agent state, for example, the user asks the visualized virtual agent a question and thus the visualized virtual agent will then change into an active communication visualized virtual agent state, the visualized virtual agent may be configured to provide an artificial physiological color change response to a user based on another specific selection of one or more monitored activity data of the user and/or one or more monitored physio-psychological data of the user. The activity data of the user and/or the physio-psychological data of the user which may be monitored and analyzed in order to generate artificial physiological color change responses to a user may therefore be different for different visualized virtual agent states and be different for different states of a user. The visualized virtual agent may further be configured to provide visual responses combined with audio responses to the user. Visual responses and/or the audio responses may be further different for different visualized virtual agent states and/or different states of a user.

Thus, the present invention further relates to a visualized virtual agent configured to provide a visual response to a user and configured to monitor over time one or more user-specific parameter, wherein user-specific data for at least one user-specific parameter are acquired by at least one sensor, the user-specific parameter comprising activity data of the user and/or physio-psychological data of the user, wherein the visualized virtual agent is configured to provide an artificial physiological color change response to a user for at least one visualized virtual agent state and for a current state of the user, wherein the at least one visualized virtual agent state and/or the current state of the user is determined on the basis of the activity data of the user and/or of the physio-psychological data of the user; wherein the visualized virtual agent is configured to adapt the artificial physiological color change response to monitored changes of the activity data of the user and/or the physio-psychological data of the user, wherein the adaption of the artificial physiological color change response comprises at least in part a color change of the visualized virtual agent for the at least one visualized virtual agent state and the current state of the user.

Thus, the present invention further relates to a visualized virtual agent configured to provide a visual response to a user and configured to monitor over time one or more user-specific parameter of the user, wherein user-specific data for at least one user-specific parameter are acquired by at least one sensor, the user-specific parameter comprising activity data of the user and/or physio-psychological data of the user, wherein the visualized virtual agent is configured to provide an artificial physiological color change response to a user for at least one visualized virtual agent state and/or for a current state of the user, wherein the at least one visualized virtual agent state and/or the current state of the user is determined on the basis of the activity data of the user and/or of the physio-psychological data of the user; wherein the visualized virtual agent is configured to adapt the artificial physiological color change response to monitored changes of the activity data of the user and/or the physio-psychological data of the user, wherein the adaption of the artificial physiological color change response comprises at least in part a color change of the visualized virtual agent for the at least one visualized virtual agent state and/or the current state of the user, wherein the visualized virtual agent is configured to provide different artificial physiological color change responses to a user on the basis of different specific selections of one or more user-specific parameter of activity data of a user and/or physio-psychological data of a user for different visualized virtual agent states and different states of a user, wherein the visualized virtual agent is configured to change between each visualized virtual agent state and/or each state of the user in order to provide artificial physiological color change responses for the current situation of a user.

Referring now to FIG. 4 a visualized virtual agent system 400 for providing and operating a visualized virtual agent according to an embodiment of the present invention will be described. The system 400 includes an electronic device 401 comprising one or more processor(s) 408 and memory 409. The electronic device includes visualized virtual agent platform 402. The electronic device 401 may be any suitable computing device for generating the visualized virtual agent of the present invention, including but not limited to a smartphone, smart glasses, a smart watch a laptop, a computer, a tablet, etc. The electronic device preferably relates to an electronic device used by the user. The electronic device 401 may include a display device 407 configured for displaying the visualized virtual agent. The electronic device 401 may be connected to one or more display devices 407 configured for displaying the visualized virtual agent. The electronic device 401 may be connected or may include one or more sensors 404. The sensors 404 may collect sensor data and may provide and transmit the sensor data to the user-specific parameter monitoring component 405 of the visualized virtual agent platform 402. The user-specific parameter monitoring component 405 is configured to monitor over time, preferably in real-time or in near real-time, one or more user-specific parameter of the user, wherein user-specific data for at least one user-specific parameter are acquired by at least one sensor 404. The user-specific parameter monitoring component 405 is configured to monitor user-specific data for the one or more user-specific parameter. The user-specific parameters comprise activity data of a user and/or physio-psychological data of a user. The visualized virtual agent platform 402 further includes a user-specific data analysis component 403 configured for analyzing the user-specific data collected and monitored by the user-specific parameter monitoring component 405. The user-specific data analysis component 403 further includes a user-specific parameter selection component 415. The user-specific parameter selection component 415 is configured to determine a selection of one or more user-specific parameter for generation of the artificial physiological color change response to the user. The user-specific data analysis component 403 further includes a current state of the user determination component 416 configured to determine a current state of the user based on activity data of a user and/or physio-psychological data of the user from the user-specific parameter monitoring component 405. After determining the current state of the user by the current state of the user determination component 416 the determined current state of the user is provided to the user-specific parameter selection component 415. As shown, the user-specific data analysis component 403 further includes a visualized virtual state determination component 417 configured to determine a visualized virtual agent based on activity data of a user and/or physio-psychological data of a user from the user-specific parameter monitoring component 405. After determining the visualized virtual agent state by the visualized virtual agent state determination component 417 the determined visualized virtual agent state is provided to the user-specific parameter selection component 415. The user-specific parameter selection component 415 then determines a selection of one or more user-specific parameter for generation of the artificial physiological color change response to the user based on the determined current state of the user and based on the determined visualized virtual agent state. Based on the determined selection of one or more user-specific parameter by the user-specific parameter selection component 415 the user-specific parameter analysis component 403 is configured to analyze the user-specific data for the one or more user-specific parameter of the selection of one or more user-specific parameter monitored by the user-specific parameter monitoring component. The user-specific data analysis component 403 is configured to generate instructions for the visualized virtual agent rendering component 406 based on the analyzed user-specific data of the selection of the one or more user-specific parameter. Based on the received instructions the visualized virtual agent rendering component 406 may be configured to render and provide the artificial physiological color change response to the user by the one or more display devices 407. The electronic device may be further connected to a network 410, such as the Internet. One or more databases 411 and/or one or more servers 412 may be connected to the network 410. The electronic device 401 may be configured to transmit data to the databases 411 and/or servers 412 through the network 410. The electronic device 401 may receive data from the databases 311 and/or servers 412 through the network 410. One or more electronic device 413, 414 may be connected to the network 410. The one or more electronic device may relate to additional electronic devices of the user. The one or more electronic devices 413, 414 may comprise one or more display devices. The electronic devices 413, 414 may be any suitable computing devices for providing or rendering the visualized virtual agent of the present invention, including but not limited to a smartphone, smart glasses, a smart watch a laptop, a computer, a tablet, etc. Thus, the instructions of the user-specific data analysis component 403 or the visualized virtual agent rendering component 406 may be transmitted to the one or more electronic devices 413, 414 for rendering the visualized virtual agent for providing the artificial physiological color change response to the user.

Thus, in one embodiment of the present invention the visualized virtual agent may be configured to provide an artificial physiological color change response to a user for at least one visualized virtual agent state and/or for at least one state of the user, wherein the visualized virtual agent is configured to provide a visual response to the user, wherein the at least one visualized virtual agent state and/or the state of the user is determined on the basis of activity data of the user and/or of physio-psychological data of the user and wherein the visualized virtual agent is configured to adapt the visual response to monitored changes of the activity data of the user and/or the physio-psychological data of the user, wherein the adaption of the visual response comprises at least in part a color change of the visualized virtual agent for the at least one visualized virtual agent state and/or state of the user.

In one embodiment of the present invention the visualized virtual agent may be configured to provide an artificial physiological color change response to a user for at least one visualized virtual agent state and/or for a current state of the user, wherein the visualized virtual agent is configured to provide a visual response to the user, wherein the at least one visualized virtual agent state and/or the current state of the user is determined on the basis of activity data of the user and/or of physio-psychological data of the user and wherein the visualized virtual agent is configured to adapt the visual response to monitored changes of the activity data of the user and/or the physio-psychological data of the user, wherein the adaption of the visual response comprises at least in part a color change of the visualized virtual agent for the at least one visualized virtual agent state and/or current state of the user.

Referring now to FIG. 5 an exemplary user-specific parameter monitoring component 105, 205, 305, 405 of the visualized virtual agent platforms 102, 202, 302, 402 which may be implemented on an electronic device 101, 201, 302, 402 of a visualized virtual agent system 100, 200, 300, 400 for providing and operating a visualized virtual agent according to an embodiment of the present invention will be described. The user-specific parameter monitoring component 105, 205, 305, 405 is configured to monitor over time, preferably in real-time or near-real time, one or more user-specific parameter of the user illustrated as user-specific parameter 1, user-specific parameter 2, user-specific parameter 3, user-specific parameter 4, user-specific parameter 5, user-specific parameter 6, user-specific parameter 7 to user-specific parameter n. As illustrated in FIG. 5 each of the user-specific parameter is connected or assigned to a specific user parameter selected from activity parameter, physiological parameter and psychological parameter. As shown in FIG. 5 the user-specific parameter 1 is connected to activity parameter 1, the user-specific parameter 2 is connected to activity parameter 2 and so on. Although three activity parameters are shown in FIG. 5 the number of activity parameter is not limited to said number, any number of activity parameter may be monitored by the user-specific parameter monitoring component 105, 205, 305, 405. The total number of activity parameter corresponds to the monitored activity data of a user. Although two physiological parameters are shown in FIG. 5 the number of physiological parameter is not limited to said number, any number of physiological parameter may be monitored by the user-specific parameter monitoring component 105, 205, 305, 405. Although two psychological parameters are shown in FIG. 5 the number of psychological parameter is not limited to said number, any number of psychological parameter may be monitored by the user-specific parameter monitoring component 105, 205, 305, 405. The total number of physiological parameter together with the total number of psychological parameter corresponds to the physio-psychological data of a user. Each of the parameter of the user-specific data, thus, each of the activity parameter, each of the physiological parameter and each of the psychological parameter correspond to a user-specific parameter which is monitored by the user-specific parameter monitoring component 105, 205, 305, 405. Preferably user-specific data for at least one user-specific parameter are acquired by at least one sensor. Thus, it is preferred that at least one of the user-specific parameter of the user-specific parameter 1, user-specific parameter 2, user-specific parameter 3, user-specific parameter 4 to user-specific parameter n is monitored by at least one sensor. Thus, one or more of the user-specific parameter and thus one or more of the activity parameter, the physiological parameter and the psychological parameter may be monitored by one or more sensors.

Referring now to FIG. 6 an exemplary current state of the user determination component 316, 416 of the visualized virtual agent platform 302, 402 which may be implemented on an electronic device 301, 401 of a visualized virtual agent system 300, 400 for providing and operating a visualized virtual agent according to an embodiment of the present invention will be described. The current state of the user determination component 316 is configured to receive the user-specific data of the monitored one or more user-specific parameter illustrated as user-specific parameter 1, user-specific parameter 2, user-specific parameter 3, user-specific parameter 4, user-specific parameter 5, user-specific parameter 6, user-specific parameter 7 to user-specific parameter n from the user-specific parameter monitoring component 305. For example, the user-specific parameter 1, 2, 3, 4, 5, 6 to n correspond to the user-specific parameter 1, 2, 3, 4, 5, 6 to n as already illustrated in FIG. 5. in connection with the user-specific parameter monitoring component 105, 205, 305, 405. Thus, each of the user-specific parameter shown in FIG. 7 is connected or assigned to a specific user parameter selected from activity parameter, physiological parameter or psychological parameter, for example, as illustrated in FIG. 5. The current state of the user determination component 316, 416 is configured to determine a current state of a user. As shown in FIG. 6 the current state of the user determination component 316, 416 included one or more states of a user, illustrated as state of a user 1, state of a user 2, state of user 3, state of a user 4, state of a user 5, state of a user 6, state of a user 7 to state of a user n. The states of the user may relate to stored information for one or more states of a user. The states of the user therefore may relate to state of the user models including information concerning a specific state of a user. The state of the user models may be stored on a memory of electronic device 301, 401 or may be obtained from one or more databases 311, 411 or one or more servers 312, 412. A state of a user may for example correspond to specific activities of a user or conditions to a user. As an example a specific activity may relate to running state of the user. The running state of the user may be determined by monitoring one or more user-specific parameter for example by a step counting sensor, heart rate monitoring sensor etc. In this example user-specific parameter 1 may be assigned to heart rate of a user, user-specific parameter 2 may relate to the location of a user, user-specific parameter 3 may related to the movement speed of the user etc. The collected and monitored user-specific data from the user-specific parameter monitoring component 305, 405 may be provided and transmitted to the current state of the user determination component 316, 416 and the monitored user-specific data may be assigned to the one or more states of the user from the current state of the user determination component 316, 416. One or more of the user-specific parameter 1 to n may be therefore connected and assigned to one or more states of a user. The connections are illustrated by the arrows in FIG. 6. The connections are not limited to the connections and combinations of user-specific parameter and state of the users as illustrated in FIG. 6. The current state of the user determination component 316, 416 receives the monitored user-specific data for the one or more user-specific parameter and based on the monitored user-specific data the current state of the user determination component 316, 416 is further configured to determine a state of the user from one or more states of a user stored in the current state of the user determination component 316, 416. The determined state of a user, for example, as shown in FIG. 6, the state of a user 1, may correspond to the current state of the user. The artificial physiological color change response of the user may be then provided on the basis of the current state of the user, which in this example, is assigned to the state of a user 1.

Referring now to FIG. 7, an exemplary user-specific parameter selection component 315 of the visualized virtual agent platform 302 which may be implemented on an electronic device 301 of a visualized virtual agent system 300 for providing and operating a visualized virtual agent according to an embodiment of the present invention will be described. The user-specific parameter selection component 315 is configured to determine a selection of one or more user-specific parameter as a basis for generating the artificial physiological color change response to the user. At first, the user specific parameter selection component 315 receives the determined current state of the user from current state of the user determination component 316. In this example, the current state of the user determination component 316 has determined the state of the user 1 as current state of the user (as illustrated in FIG. 6). As illustrated in FIG. 7 the user-specific parameter selection component 315 includes one or more predefined models comprising a connection and assignment between one or more states of a user and one or more user-specific parameter that are suitable as basis for generating the artificial physiological color change response to the user. For example for a determined state of a user 1 it is predefined that user-specific parameter 1 and user-specific parameter 2 are suitable as basis for generating the artificial physiological color change response to the user. Thus, the user-specific parameter selection component 315 receives the determined current state of the user from the current state of the user determination component 316, which has been determined as state of a user 1 in this example. Then, based on the stored information concerning the state of a user and one or more user-specific parameter useful for the artificial physiological color change response the user-specific parameter selection component 315 is configured to determine user-specific parameter 1 and user-specific parameter 2 as the user-specific parameter be used for generating the artificial physiological color change response to the user. The user-specific parameter selection component 315 then transmits or provides the selection of the determined user-specific parameter to user-specific data analysis component 303. The user specific data analysis component 303 then provides instructions to the visualized virtual agent rendering component 306 for providing an artificial physiological color change response to the user based on the determined user-specific parameter, in this example, based on user-specific parameter 1 and user-specific parameter 2. Furthermore, the user-specific data analysis component receives user-specific data for the user-specific parameter 1 and user-specific parameter 2 from the user-specific parameter monitoring component 305 and based on a monitored change of user-specific parameter 1 and/or user specific parameter 2 the user-specific data analysis component provides instructions to the visualized virtual agent rendering component 306 for adapting the artificial physiological color change response to the user. As shown in FIG. 7 for each state of a user, such as the state of a user 1, state of a user 2, state of user 3, state of a user 4, state of a user 5, state of a user 6, state of a user 7 to state of a user n, one or more user-specific parameter are connected or assigned to the respective state of the user. Although for the illustrated states of the user 1 to n two or three user-specific parameter are assigned to the respective states of the user the number of assigned user-specific parameter are not limited to two or three, any number of user-specific parameter may be assigned to a state of the user. Moreover, it is preferred that at least one or the user-specific parameter assigned to each of the states of the user corresponds to a user-specific parameter for which the user-specific data are acquired by at least one sensor. Thus, in this example, it is preferred that for example user-specific parameter 1 is monitored by at least one sensor. Furthermore, user specific parameter 2 may be also monitored by at least one sensor. Thus, user-specific parameter 1 and user-specific parameter 2 are preferably monitored by at least one sensor or one or more sensors 304. In the example shown in FIG. 7 each of the illustrated states of the user 1 to n include either user-specific parameter 1 or user-specific parameter 2 or both. Thus, in this example, for each determined state of the user, thus for each current state of a user, at least one user-specific parameter is monitored through at least one sensor, thus the artificial physiological color change response provided by the visualized virtual agent is based on user-specific data for at least one user-specific parameter acquired by at least one sensor.

Referring now to FIG. 8, an exemplary user-specific parameter selection component 415 of the visualized virtual agent platform 402 which may be implemented on an electronic device 401 of a visualized virtual agent system 400 for providing and operating a visualized virtual agent according to an embodiment of the present invention will be described. The user-specific parameter selection component 415 is configured to determine a selection of one or more user-specific parameter as a basis for generating the artificial physiological color change response to the user. At first, the user specific parameter selection component 415 receives the determined current state of the user from current state of the user determination component 416. In this example, the current state of the user determination component 416 has determined the state of the user 1 as current state of the user. Furthermore, the user-specific parameter selection component 415 receives the determined visualized virtual agent state from the visualized virtual agent state determination component 417. In this example, the visualized virtual agent state determination component 417 has determined the visualized virtual agent state 1 as visualized virtual agent state. As illustrated in FIG. 8 the user specific parameter selection component 415 includes one or more predefined models comprising a connection or assignment between one or more states of a user, one or more visualized virtual agent states and one or more user-specific parameter that are suitable as basis for generating the artificial physiological color change response to the user. For example for a determined state of a user 1 and a determined visualized virtual agent state 1 it is defined that user-specific parameter 1 and user-specific parameter 2 are suitable as basis for generating the artificial physiological color change response to the user. Thus, the user-specific parameter selection component 415 receives the determined current state of the user from the current state of the user determination component 416 and receives the determined visualized virtual agent from the visualized virtual agent state determination component 417. Then, based on the stored information concerning the state of a user, the visualized virtual agent state and one or more user-specific parameter useful for generating the artificial physiological color change response to the user, the user-specific parameter selection component 415 is configured to determine user-specific parameter 1 and user-specific parameter 2 as the user-specific parameter to be used for generating the artificial physiological color change response to the user. The user-specific parameter selection component 415 then transmits or provides the selection of the determined user-specific parameter to user-specific data analysis component 403. The user specific data analysis component 403 then provides instructions to the visualized virtual agent rendering component 406 for providing an artificial physiological color change response to the user based on the determined user-specific parameter, in this example, based on user-specific parameter 1 and user-specific parameter 2. Furthermore, the user-specific data analysis component 406 receives user-specific data for the user-specific parameter 1 and user-specific parameter 2 from the user-specific parameter monitoring component 405 and based on a monitored change of user-specific parameter 1 and/or user specific parameter 2 the user-specific data analysis component provides instructions to the visualized virtual agent rendering component 406 for adapting the artificial physiological color change response to the user. As shown in FIG. 8 for each state of a user, such as the state of a user 1, state of a user 2 to state of a user n, and each visualized virtual agent state, such as visualized virtual agent state 1 or 2, one or more user-specific parameter are connected or assigned to the respective combination models of states of the user and visualized virtual agent states. Although for the illustrated states of the user/visualized virtual agent state models include two or three user-specific parameter that are assigned to the respective states of the user/visualized virtual agent states the number of assigned user-specific parameter are not limited to two or three, any number of user-specific parameter may be assigned to a state of the user/visualized virtual agent model. Moreover, it is preferred that at least one or the user-specific parameter assigned to each of the states of the user/visualized virtual agent state models corresponds to a user-specific parameter for which the user-specific data are acquired by at least one sensor. Thus, in this example, it is preferred that for example user-specific parameter 1 is monitored by at least one sensor. Furthermore, user specific parameter 4 may be also monitored by at least one sensor. Thus, user-specific parameter 1 and user-specific parameter 4 are preferably monitored by at least one sensor or one or more sensors 304 in this example. In the example shown in FIG. 7 each of the illustrated states of the user/visualized virtual agent combinations include either user-specific parameter 1 or user-specific parameter 4 or both. Thus, in this example, for each determined state of the user, thus for each current state of a user, in combination with each determined visualized virtual agent state at least one user-specific parameter is monitored by at least one sensor, thus the artificial physiological color change response provided by the visualized virtual agent is based on user-specific data for at least one user-specific parameter acquired by at least one sensor.

Referring now to FIG. 9 a visualized virtual agent system 500 for providing and operating a visualized virtual agent according to an embodiment of the present invention will be described. The system 500 includes an electronic device 501 comprising one or more processor(s) 508 and memory 509. The electronic device includes visualized virtual agent platform 502. The electronic device 501 may be any suitable computing device for generating the visualized virtual agent of the present invention, including but not limited to a smartphone, smart glasses, a smart watch a laptop, a computer, a tablet, etc. The electronic device preferably relates to an electronic device used by the user. The electronic device 501 may include a display device 507 configured for displaying the visualized virtual agent. The electronic device 501 may be connected to one or more display devices 507 configured for displaying the visualized virtual agent. The electronic device 501 may be connected or may include one or more sensors 504. The sensors 504 may collect sensor data and may provide and transmit the sensor data to the user-specific parameter monitoring component 505 of the visualized virtual agent platform 502. The user-specific parameter monitoring component 505 is configured to monitor over time, preferably in real-time or in near real-time, one or more user-specific parameter of the user, wherein user-specific data for at least one user-specific parameter are acquired by at least one sensor 504. The user-specific parameter monitoring component 505 is configured to monitor user-specific data for the one or more user-specific parameter. The user-specific parameters comprise activity data of a user and/or physio-psychological data of a user. The visualized virtual agent platform 502 further includes a user-specific data analysis component 503 configured for analyzing the user-specific data collected and monitored by the user-specific parameter monitoring component 505. The user-specific data analysis component 503 further includes a current state of the user determination component 516 configured to determine a current state of the user based on activity data of a user and/or physio-psychological data of the user from the user-specific parameter monitoring component 505. After determining the current state of the user by the current state of the user determination component 516 the determined current state of the user is provided to the user-specific data analysis component 505. Based on the determined current state of the user the user-specific parameter analysis component 503 is configured to generate instructions for the visualized virtual agent rendering component 506. Based on the received instructions the visualized virtual agent rendering component 506 may be configured to render and provide the artificial physiological color change response to the user by the one or more display devices 507. The electronic device may be further connected to a network 510, such as the Internet. One or more databases 511 and/or one or more servers 512 may be connected to the network 510. The electronic device 501 may be configured to transmit data to the databases 511 and/or servers 512 through the network 510. The electronic device 501 may receive data from the databases 511 and/or servers 512 through the network 510. One or more electronic device 513, 514 may be connected to the network 510. The one or more electronic device may relate to additional electronic devices of the user. The one or more electronic devices 513, 514 may comprise one or more display devices. The electronic devices 513, 514 may be any suitable computing devices for providing or rendering the visualized virtual agent of the present invention, including but not limited to a smartphone, smart glasses, a smart watch a laptop, a computer, a tablet, etc. Thus, the instructions of the user-specific data analysis component 503 or the visualized virtual agent rendering component 406 may be transmitted to the one or more electronic devices 513, 514 for rendering the visualized virtual agent for providing the artificial physiological color change response to the user.

Referring now to FIG. 10 an exemplary implementation of the visualized virtual agent system 500 for providing and operating a visualized virtual agent according to an embodiment of the present invention will be described. The system 500 includes an electronic device 501 comprising one or more processor(s) 508 and memory 509. A visualized virtual agent platform 502 in accordance with the present invention is shown. The visualized virtual agent platform may be implemented on the electronic device 501 or parts of the visualized virtual agent platform 502 may be implemented on one or more databases 511 and/or one or more servers 512. The electronic device 501 may be any suitable computing device for generating the visualized virtual agent of the present invention, including but not limited to a smartphone, smart glasses, a smart watch a laptop, a computer, a tablet, etc. The electronic device 501 relates to an electronic device used by the user. The electronic device 501 may include a display device 507 configured for displaying the visualized virtual agent. The electronic device 501 may be connected to one or more display devices 507 configured for displaying the visualized virtual agent. The electronic device 501 may be connected or may include one or more sensors 504. The sensors 504 may collect sensor data and may provide and transmit the sensor data to the user-specific parameter monitoring component 505 of the visualized virtual agent platform 502. As illustrated in FIG. 10 one or more sensors 504 are connected to the user and are configured to collect sensor data for at least one user-specific parameter of the user. The user-specific parameter monitoring component 505 is configured to monitor over time, preferably in real-time or in near real-time, one or more user-specific parameter of the user, wherein user-specific data for at least one user-specific parameter are acquired by at least one sensor 504. The user-specific parameter monitoring component 405 is configured to monitor user-specific data for the one or more user-specific parameter. The user-specific parameters comprise activity data of a user and/or physio-psychological data of a user. The user-specific parameter monitoring component 505 may include one or more databases 511 and/or one or more servers 512. The user-specific parameter monitoring component 505 may request and receive user-specific data for one or more user-specific parameter from one or more databases 511 and/or one or more servers 512. The user-specific parameter monitoring component 505 may transmit and provide user-specific data for one or more user-specific parameter to one or more databases 511 and/or one or more servers. The one or more databases and/or one or more servers 512 may comprise third party services. The sensors 504 may also transmit the collected sensor data for one or more user-specific parameter to the one or more databases 511 and/or one or more server 512 and the user-specific parameter monitoring component 505 may request and obtain the collected sensor data from the one or more databases 511 and/or one or more server 512. The visualized virtual agent platform 502 further includes a user-specific data analysis component 503 configured for analyzing the user-specific data collected and monitored by the user-specific parameter monitoring component 505. The user-specific data analysis component 503 further includes a current state of the user determination component 516 configured to determine a current state of the user based on activity data of a user and/or physio-psychological data of the user from the user-specific parameter monitoring component 505. The current state of the user determination component 516 may be configured to determine a user state, preferably the current state of a user, by applying a user state activation function. After determining the state of the user, preferably the current state of the user by the current state of the user determination component 516 the determined current state of the user is provided to the user-specific data analysis component 505. Based on the determined current state of the user the user-specific parameter analysis component 503 is configured to generate instructions for the visualized virtual agent rendering component 506. Based on the received instructions the visualized virtual agent rendering component 506 may be configured to render and provide the artificial physiological color change response to the user by the one or more display devices 507. The visualized virtual agent rendering component 506 may determine the artificial physiological color change response by applying a color creation function. Based on the determined color value the visualized virtual agent may be rendered and displayed on display device 507 with the determined color. The electronic device may be further connected to a network 510, such as the Internet. One or more databases 511 and/or one or more servers 512 may be connected to the network 510. The electronic device 501 may be configured to transmit data to the databases 511 and/or servers 512 through the network 510. The electronic device 501 may receive data from the databases 511 and/or servers 512 through the network 510. One or more electronic device 513, 514 may be connected to the network 510. The one or more electronic device may relate to additional electronic devices of the user. The one or more electronic devices 513, 514 may comprise one or more display devices. The electronic devices 513, 514 may be any suitable computing devices for providing or rendering the visualized virtual agent of the present invention, including but not limited to a smartphone, smart glasses, a smart watch a laptop, a computer, a tablet, etc. Thus, the instructions of the user-specific data analysis component 503 or the visualized virtual agent rendering component 506 may be transmitted to the one or more electronic devices 513, 514 for rendering the visualized virtual agent for providing the artificial physiological color change response to the user.

Referring now to FIG. 11 an exemplary current state of the user determination component 516 of the visualized virtual agent platform 500 which may be implemented on an electronic device 501 of a visualized virtual agent system 500 for providing and operating a visualized virtual agent according to an embodiment of the present invention will be described. The current state of the user determination component 516 is configured to receive the user-specific data of the monitored one or more user-specific parameter illustrated as user-specific parameter 1, user-specific parameter 2, user-specific parameter 3, user-specific parameter 4, user-specific parameter 5, user-specific parameter 6, user-specific parameter 7 to user-specific parameter n from the user-specific parameter monitoring component 505. For example, the user-specific parameter 1, 2, 3, 4, 5, 6 to n correspond to the user-specific parameter 1, 2, 3, 4, 5, 6 to n as already illustrated in FIG. 5. in connection with the user-specific parameter monitoring component 105, 205, 305, 405. Thus, each of the user-specific parameter shown in FIG. 11 is connected or assigned to a specific user parameter selected from activity parameter, physiological parameter or psychological parameter, for example, as illustrated in FIG. 5. The current state of the user determination component 516 is configured to determine a current state of a user. As shown in FIG. 6 the current state of the user determination component 516 includes one or more states of a user, illustrated as state of a user 1, state of a user 2, state of user 3, state of a user 4, state of a user 5, state of a user 6, state of a user 7 to state of a user n. The states of the user may relate to stored information for one or more states of a user. The states of the user therefore may relate to state of the user models including information concerning a specific state of a user. The state of the user models may be stored on a memory of electronic device 501, 501 or may be obtained from one or more databases 511, 511 or one or more servers 512, 512. A state of a user may for example correspond to specific activities of a user or conditions to a user. As an example a specific activity may relate to running state of the user. The running state of the user may be determined by monitoring one or more user-specific parameter for example by a step counting sensor, heart rate monitoring sensor etc. In this example user-specific parameter 1 may be assigned to heart rate of a user, user-specific parameter 2 may relate to the location of a user, user-specific parameter 3 may relate to the movement speed of the user etc. The collected and monitored user-specific data from the user-specific parameter monitoring component 505 may be provided and transmitted to the current state of the user determination component 516 and the monitored user-specific data may be assigned to the one or more states of the user from the current state of the user determination component 516. One or more of the user-specific parameter 1 to n may be therefore connected and assigned to one or more states of a user. The connections are illustrated by the arrows in FIG. 11. The connections are not limited to the connections and combinations of user-specific parameter and state of the users. The current state of the user determination component 516 receives the monitored user-specific data for the one or more user-specific parameter and based on the monitored user-specific data the current state of the user determination component 516 is further configured to determine a current state of the user from the one or more states of a user stored in the current state of the user determination component 516. The current state of the user determination component 516 may be configured for processing the user-specific data by application a user state activation function. The user state activation function has the role to transform the value of the user-specific data of the one or more user-specific parameter in a user state value. The user state value may be for example equal to +1, −1 or 0. The user state value may represent a weighted factor, for example, the user state value +1 may relate to a positive factor, the user state value of 0 may relate to a neutral factor and the user state value of −1 may relate to a negative factor. For example, the positive factor may relate to a positive health factor, the neutral factor may relate to a neutral health factor and the negative factor may relate to a negative health factor or unhealthy factor. The user state activation function may give an output (+1, 0, −1) even when the user-specific data for one or more user-specific parameter are missing. Missing data may be interpreted as negative factor. The user state functions may be created by identifying the user-specific data, defining a domain of the function (unit and range of values) and defining for each possible output (+1, 0, −1) the associated range of input values. The current state of the user determination component 516 may be configured to combine the generated output values for the states of the user, thus for each state of a user, to provide a current state of the user.

Referring now to FIG. 12 an exemplary current state of the user determination component 516 of the visualized virtual agent platform 500 which may be implemented on an electronic device 501 of a visualized virtual agent system 500 for providing and operating a visualized virtual agent according to an embodiment of the present invention will be described. The current state of the user determination component 516 is configured to receive the user-specific data of the monitored one or more user-specific parameter illustrated as user-specific parameter 1, user-specific parameter 2, user-specific parameter 3, user-specific parameter 4, user-specific parameter 5, user-specific parameter 6, user-specific parameter 7 to user-specific parameter n from the user-specific parameter monitoring component 505. For example, the user-specific parameter 1, 2, 3, 4, 5, 6 to n correspond to the user-specific parameter 1, 2, 3, 4, 5, 6 to n as already illustrated in FIG. 5. in connection with the user-specific parameter monitoring component 105, 205, 305, 405. Thus, each of the user-specific parameter shown in FIG. 11 is connected or assigned to a specific user parameter selected from activity parameter, physiological parameter or psychological parameter, for example, as illustrated in FIG. 5. The current state of the user determination component 516 is configured to determine a current state of a user. As shown in FIG. 6 the current state of the user determination component 516 includes one or more states of a user, illustrated as state of a user 1, state of a user 2, state of user 3, state of a user 4, state of a user 5, state of a user 6, state of a user 7 to state of a user n. The states of the user may relate to stored information for one or more states of a user. The states of the user therefore may relate to state of the user models including information concerning a specific state of a user. The state of the user models may be stored on a memory of electronic device 501, 501 or may be obtained from one or more databases 511, 511 or one or more servers 512, 512. A state of a user may for example correspond to specific activities of a user or conditions to a user. As an example a specific activity may relate to running state of the user. The running state of the user may be determined by monitoring one or more user-specific parameter for example by a step counting sensor, heart rate monitoring sensor etc. In this example user-specific parameter 1 may be assigned to heart rate of a user, user-specific parameter 2 may relate to the location of a user, user-specific parameter 3 may relate to the movement speed of the user etc. The collected and monitored user-specific data from the user-specific parameter monitoring component 505 may be provided and transmitted to the current state of the user determination component 516 and the monitored user-specific data may be assigned to the one or more states of the user from the current state of the user determination component 516. One or more of the user-specific parameter 1 to n may be therefore connected and assigned to one or more states of a user. The connections are illustrated by the arrows in FIG. 11. The connections are not limited to the connections and combinations of user-specific parameter and state of the users. The current state of the user determination component 516 receives the monitored user-specific data for the one or more user-specific parameter and based on the monitored user-specific data the current state of the user determination component 516 is further configured to determine a current state of the user from the one or more states of a user stored in the current state of the user determination component 516. The current state of the user determination component 516 may be configured for processing the user-specific data by application a user state activation function. The user state activation function has the role to transform the value of the user-specific data of the one or more user-specific parameter in a user state value. The user state value may be for example equal to +1, −1 or 0. The user state value may represent a weighted factor, for example, the user state value +1 may relate to a positive factor, the user state value of 0 may relate to a neutral factor and the user state value of −1 may relate to a negative factor. For example, the positive factor may relate to a positive health factor, the neutral factor may relate to a neutral health factor and the negative factor may relate to a negative health factor or unhealthy factor. The user state activation function may give an output (+1, 0, −1) even when the user-specific data for one or more user-specific parameter are missing. Missing data may be interpreted as negative factor. The user state functions may be created by identifying the user-specific data, defining a domain of the function (unit and range of values) and defining for each possible output (+1, 0, −1) the associated range of input values. As shown in FIG. 12 one or more states of the user may be combined to one or more state of the user groups. For example, as shown in FIG. 12 state of the user 1 to 4 may be combined to state of the user group 1 and state of the user 5 to 7 may be combined to a state of the user group 2 and so on. The groups may correspond for example to movement, nutrition, cognition, ambient and personal data groups. The movement group may include user-specific movement data of a user, the nutrition group may include user-specific nutrition data of a user and so on. The current state of the user determination component 516 may be configured to provide the current state of the user as the one or more state of the user groups or may provide the current state of the user separately for the one or more state of the user groups.

For example, a user state activation function for Body Mass Index (BMI) may be determined according to the following formula:

$$D_{f_{max}}:[12, \ldots, 42] \to [1, 0, -1]$$

$$f_{BMI}(x) \begin{cases} 0 & \text{if } x \text{ is missing} \\ 1 & \text{if } x \in ]18; 26[ \\ -1 & \text{if } x \in [12; 18] \cup [26; 42] \end{cases}$$

For example, a user state activation function for Fitness may be determined according to the following formula:

$$D_{f_{FitnessKalories}}: \mathbb{R} \to [1, 0, -1]$$

$$f_{FitnessKalories}(x) \begin{cases} 0 & \text{if } x \leq 99 \\ -1 & \text{if } x \text{ is missing} \\ 1 & \text{if } x \geq 100 \end{cases}$$

For example, a user state activation function for Fitness may be determined according to the following formula:

$$D_{f_{Steps}}: \mathbb{R} \to [1, 0, -1]$$

$$f_{Steps}(x) \begin{cases} 0 & \text{if } x \in \phi \\ -1 & \text{if } x \text{ is missing or } x \leq 1000 \\ 1 & \text{if } x \geq 1001 \end{cases}$$

Referring now to FIG. 13 the exemplary current state of the user determination component 516 of the visualized virtual agent platform 500 which may be implemented on an electronic device 501 of a visualized virtual agent system 500 for providing and operating a visualized virtual agent according to an embodiment of the present invention of FIG. 12 will be further described. As shown in FIG. 13 the current state of the user is provided separately for one or more state of the user groups, for example, state of the user group 1, state of the user group 2 and so on. For each state of the user group the current state of the user determination component 516 may determine a user state values average which may be provided as group values, for example, group 1, group 2 and so on. The group values may be provided, by the user-specific data analysis component 503 to the visualized virtual agent rendering component 506. As shown in FIG. 13 the visualized virtual agent rendering component 506 comprises a value to color (RGB) converter 518. It should be understood, that the value to color (RGB) converter 518 may be also provided for the visualized virtual agent rendering component 106, 206, 306 and 406 of the herein described systems 100, 200, 300 and 400. As shown in FIG. 13 the value to color (RGB) converter 518 receives the group values representing a current state of the user from the current state of the user determination component 516. The value to color (RGB) converter 518 is configured to convert the one or more group values to color values. The visualized virtual agent rendering component 506 is further configured to apply the converted color values for rendering the visualized virtual agent and for displaying the visualized virtual agent on one or more a display devices 507. As the user-specific parameter monitoring component 505 monitors user-specific data over time, the user-specific parameter monitoring provides the monitored user-specific data over time to the current state of the user determination component 516. Thus, the current state of the user determination component is configured to adapt the one or more group values provided to the visualized virtual agent rendering component 506.

Referring now to FIG. 14 an embodiment for the visualized virtual agent rendering component 506 of FIG. 13 will be further described. The visualized virtual agent rendering component 506 may be configured to determine a group array of group color order by descending group values of the one or more groups determined for the current state of the user by the current state of the user determination component 516. The group array may comprise the form group value I, group value i+1 and so on. On the right side of FIG. 14 a colored shape is illustrated. The colored shape includes a shape width. The shape width is subdivided into segments. As segment may correspond to the total shape width divided by the number of groups n. For each segment a gradient of the group is provided, for example, as shown in FIG. 14 Gradient of group I for the first segment, and gradient of group i+1 for the second segment. The color gradient is provided by the start color of group color i to end color of group color i+1 for the first segment and the color gradient for the second segment is provided by the start color of group color i+1 to the end color of group color i+2.

The value to color (RGB) converter 518 may be further configured to apply a function that takes as input the RGB code associated to a positive state value that is +1, the RGB code associated to a negative state value that is -1 and the group average value. The value to color (RGB) converter 518 may be configured to output the RGB code associated to the state of the user groups given as input. The value to color (RGB) converter 518 is configured to apply the function for each state of the user group to calculate the respective RGB code, in order to complete the state of the user group array of state of the user group colors (RGB codes) ordered by descending state of the user group state average.

The value to color (RGB) converter 518 may be further configured to apply a function that takes as input:

H: the RGB code associated to a positive state value that is +1. An array of size 3:

$$H = \begin{bmatrix} r2 \\ g2 \\ b2 \end{bmatrix}$$

U: the RGB code associated to negative state value that is -1. An array of size 3:

$$U = \begin{bmatrix} r1 \\ g1 \\ b1 \end{bmatrix}$$

WG: The state of the user group state average. An integer number between -1 and 1:

WG

A R3 space is defined and the dimensions represent the colors that compose the RGB code: x axis=red value, y axis=green value, z axis=blue value.

A line inside this space with the following parametric function c(H, U, WG) may be drawn:

$$\begin{bmatrix} r \\ g \\ b \end{bmatrix} = \begin{bmatrix} x0 \\ y0 \\ z0 \end{bmatrix} + WG \cdot \begin{bmatrix} a \\ b \\ c \end{bmatrix} \cdot s$$

-continued where $$\begin{bmatrix} x0 \\ y0 \\ z0 \end{bmatrix} = \frac{1}{2} \cdot \begin{bmatrix} r2 \\ g2 \\ b2 \end{bmatrix} - \begin{bmatrix} r1 \\ g1 \\ b1 \end{bmatrix}$$

$$s = \frac{(r1 - x0)}{a}$$

$$\begin{bmatrix} a \\ b \\ c \end{bmatrix} = (H - U) \cdot s$$

The function c(H, U, WG) outputs a RGB code.

The visualized virtual agent state may also depend on the currently used electronic device of a user. With other word the currently used electronic device of a user where the visualized virtual agent providing an artificial physiological color change response to a user may be stored and executed by one or more processors. With other words the currently used electronic device of a user where the computer readable instructions for generating of a visualized virtual agent providing an artificial physiological color change response to a user may be executed by at least one processor. Different electronic devices may comprise different computing systems, and not every system may be particular suitable for rendering or generating of a visualized virtual agent providing an artificial physiological color change response to a user by applying the entire data input relating to user-specific parameter like activity data of a user and/or physio-psychological data of a user. For example, the visualized virtual agent may be implemented and executed on a watch, like a smart watch, comprising a display to enable presentation of the visualized virtual agent. The visualized virtual agent may be rendered and presented on the display over time and the visualized virtual agent may be configured to generate an artificial physiological color change response over time, in real time or in real time to a user. The smart watch may include a specific graphic processing unit, which may not be suitable for rendering of the visualized virtual agent on the basis of the whole data input relating to the entire user-specific parameter of activity data of the user and/or physio-psychological data of the user. Moreover, it may not be suitable to provide an artificial physiological color change response for all monitored and/or acquired activity data of the user and/or for all monitored and/or acquired physio-psychological data of the user. Thus, in the passive or monitoring visualized virtual agent state the visualized virtual agent may provide an artificial physiologic color changes response to a user based on a selection of one or more user-specific parameter of activity data of a user and/or physio-psychological data of a user, for example, physio-psychological data of the user relating to emotions or mood of the user, which may be monitored by acquiring user-specific data from at least one sensor, for example at least one camera and/or at least one microphone. Furthermore, a specific electronic device may include integral input devices and/or sensors. The visualized virtual agent may be configured to provide an artificial physiological color change response on the basis of activity data of the user and/or physio-psychological data of the user acquired by using at least one sensor of the electronic device. In this example, the visualized virtual agent may be configured to generate the visualized virtual agent and to generate the artificial physiological color change responses without requesting other activity data of the user and/or physio-psychological data of the user. In this example it may therefore not be required that the visualized virtual agent may access, for example, one or more databases on one or more server and/or client server and/or secured server. Moreover, the activity data of a user and/or physio-psychological data of a user in order to determine a visualized virtual agent state of a user may be monitored and analyzed with a specific electronic device. In case the visualized virtual agent determines a change of the visualized virtual agent state, the electronic device may then transmit the determined change of the visualized virtual agent state to another electronic device used by the user. The other electronic device may then adapt the artificial physiological color change response to the determined change of the visualized virtual agent state and may then be configured to generate the artificial physiological color change response to the user on the basis of other activity data and/or physio-psychological data of the user. Thus, it is not required that the other electronic device independently monitors in real time or near-real time all activity data of the user and/or all physio-psychological data of the user over time, in real time or near-real time to determine a visualized virtual agent state and/or at least one state of the user, preferable a current state of the user. As shown in FIG. 1, FIG. 2, FIG. 3, FIG. 4 and FIG. 9 the visualized virtual agent platform may be implemented on an electronic device 101, 201, 301, 401, 501. The electronic device 101, 201, 301, 401, 501 may be connected to a network 110, 210, 310, 410, 510 and additional electronic devices 113, 114, 213, 214, 313, 314, 413, 414, 513, 514 may be connected to the network 110, 210, 310, 410, 510. The electronic device 101, 201, 301, 401, 501 may be configured to transmit instructions for generating an artificial physiological color change response through the network 110, 210, 310, 410, 510 to the electronic devices 113, 114, 213, 214, 313, 314, 413, 414, 513, 514. The electronic devices 113, 114, 213, 214, 313, 314, 413, 414, 513, 514 may comprise one or more display devices for rendering the visualized virtual agent of the present invention and may be configured to provide the artificial physiological color change response to the user.

The visualized virtual agent of the present invention may be configured to provide an artificial physiological color change response to a user on the basis of a visualized virtual agent state and/or current state of a user. The visualized virtual agent state and/or the current state of the user may be determined on the basis of activity data of a user and/or physio-psychological data of a user. The visualized virtual agent state and/or the current state of the user may be determined on a present behavior of the user and/or the current physiological condition of the user and/or the current mental state or psychological state of the user and/or the current medical state of the user. Furthermore the visualized virtual agent may be configured to provide a visual response combined with an audio response to the user on the basis of activity data of a user and/or physio-psychological data of a user. The visualized virtual agent may be configured to provide a visual response combined with an audio response to the user to provide information to a user. The visualized virtual agent of the present invention may be configured to provide a visual response combined with an audio response to the user on the basis of a present behavior and/or a current physical condition and/or a current mental state of the user.

Thus the visualized virtual agent may be configured to provide an artificial physiological color change response to a user for at least one visualized virtual agent state and/or for at least one state of the user, preferably a current state of the user wherein the visualized virtual agent may be configured to provide a visual response combined with an audio response to a user, wherein the at least one visualized virtual agent state and/or the current state of the user is determined on the basis of activity data of the user and/or physio-psychological data of the user and wherein the visualized virtual agent is configured to adapt the visual response to changes of the activity data of the user and/or the physio-psychological data of the user, wherein the adaption of the visual response comprises at least a color change of the visualized virtual agent for the at least one visualized virtual agent state and/or current state of the user.

The activity data of a user and/or the physio-psychological data of user may be monitored by using at least one input device and/or at least one sensor. Thus, the visualized virtual agent may be connected to at least one input device and/or at least one sensor. The visualized virtual agent may be configured to receive output signals from at least one input device. The visualized virtual agent may be configured to receive output signals from at least one sensor. The visualized virtual agent may be configured to receive output signals from one or more sensors. The visualized virtual agent may be configured to receive the output signal from one or more input devices. The at least one input device and/or at least one sensor may be an integral part of an electronic device where the visualized virtual agent may be executed or the at least one input device and/or at least one sensor may be located externally to such an electronic device. The at least one input device and/or at least one sensor may be configured to receive input signals related to a user for recognizing and/or measuring and/or monitoring an activity parameter of a user and/or physio-psychologic parameter of a user and be further configured to generate output data from the input signals related to the user. The visualized virtual agent may be connected to at least one input device and/or at least one sensor to monitor activity data of a user and/or physio-psychological data of a user. The visualized virtual agent may be configured to analyze the activity data of a user and/or physio-psychological data of a user. Thus, the visualized virtual agent may be configured to determine a visualized virtual agent state and/or current state of a user on the basis of the monitored activity data of a user and/or physio-psychological data of a user, which may be monitored by using at least one input device and/or at least one sensor. The at least one input device and/or at least one sensor may be configured to transmit the generated output data to the visualized virtual agent, for example, output data related to verbal and non-verbal behavior of the user. The at least one sensor may include suitable audio-visual sensors, activity sensors, physiological sensors, biometric sensors and/or other sensors. The at least one sensor may be configured to transmit (wired or wirelessly) the output data directly to a processor. The at least one input device and/or at least one sensor may be directly attached to the user. Alternatively the at least one input device and/or at least one sensor may be disposed within an electronic device and/or another device utilized by the user. Thus, although not shown in FIGS. 1, 2, 3, 4 and 9 the electronic devices 101, 201, 301, 401 and 501 may be further connected to one or more input devices.

The visualized virtual agent may be configured to receive output signals from one or more input devices and/or one or more sensors to obtain activity data of a user and/or physio-psychological data of a user as input data related to the user. Thus, the visualized virtual agent may be configured to receive input data relating to activity data of a user and/or physio-psychological data of a user from one or more input devices and/or one or more sensors. Preferably the visualized virtual agent may be configured to acquire input data relating to activity data of a user and/or physio-psychological data of a user by using at least one sensor. The input data may include one or more of behavior data of the user, physiological data of the user, psychological data of the user, medical data of the user and/or other information or data related to the user. The visualized virtual agent may receive the output signals generated by at least one input device and/or at least one sensor within or outside the computing system. The visualized virtual agent may be configured to receive user-specific input data from sensors, and/or other resources by electronically querying and/or requesting said data from such devices and receiving the activity data of the user and/or physio-psychological data of the user in response.

The visualized virtual agent and/or one or more processors may be configured to receive activity data of a user and/or physio-psychological data of a user and further be configured to acquire activity data of a user and/or physio-psychological data of the user from at least one sensor, and/or may be configured to receive activity data of a user and/or physio-psychological data of a user in any way that allows the visualized virtual agent or the computing system for generating the visualized virtual agent to function as described herein.

For example, physiological data of a user, which may relate to a current physical and/or physiological condition of a user may include heart rate, blood pressure, weight, pulse rate, blood chemistry, blood oxygen saturation, blood glucose level, hydration information, respiration rate, breathing information, skin/body temperature, brain activity, physical movements and/or lack of movement, user specific activity data and/or physiological data may further include data related to performance and/or non-performance of daily activities, activity duration information, physical pain information, and/or other physiological data. Examples of behavior data of a user may include the users' demeanor, voice, look, gestures, manners, attitude, and/or other behavior data. Examples of user-specific psychological data may include user's personality, mood, emotions, perceptions, cognitions, and/or other psychological data related to the user. The visualized virtual agent may be configured to extract user-specific data from acquired input signals transmitted by at least one sensor related for example via automatic speech recognition and/or audio-visual behavior recognition. The visualized virtual agent may be configured to extract user-specific input data from audio-visual input (e.g. user voice and/or video received from a microphone, and/or camera). Automatic speech recognition may include identifying words and phrases in the user's speech and converting them into machine readable format. Audio-visual behavior recognition may include facial recognition, body language recognition, recognition of acoustic non-content properties of speech (rhythm, emphasis, intonation, pitch, intensity, rate, etc.) and/or other behavior.

The visualized virtual agent may be further configured to receive and/or to acquire input data related to other users or one or more users. For example users in the same age group, same gender, users with similarities in their physiological, behavior, psychological, and/or medical information, and/or other users with other similarities to the user.

Non-verbal communication is characterized by visual cues such as body language, distance of communicators and physical environments and appearance and also of voice and of touch. Non-verbal communication can also include the use of time and eye contact and the actions of looking while talking and listening, frequency of glances, patterns of fixation, pupil dilation, and blink rate and the like. Human speech contains also non-verbal elements, including voice quality, rate, pitch, volume and speaking style, as well as prosodic features such as rhythm, intonation, and stress. Non-verbal communication also depends on environmental conditions where communication takes place, on physical characteristics of communicators, and on behaviors of communicators during interaction. Non-verbal communication is characterized by encoding and decoding processes of non-verbal cues. Encoding is related to the provision of information in form of facial expression, gestures, and postures, whereby decoding is related to the interpretation or understanding of said provided information. Some non-verbal cues relate to the inherent human behavior, for example, like smiling, crying, or laughing. Non-verbal communication may involve non-verbal cues in form of gestures. Gestures may be performed with hands, arms or body, and also include movements of the head, face and eyes. Gestures can also be categorized as either speech-independent or speech-related. Speech-independent gestures are dependent upon culturally accepted interpretation and have a direct verbal translation. Speech-related gestures are used in parallel with verbal speech. This form of non-verbal communication is used to emphasize the message that is being communicated. Speech-related gestures are intended to provide supplemental information to a verbal message such as pointing to an object of discussion. Facial expressions serve as a practical means of communication. With all the various muscles that precisely control mouth, lips, eyes, nose, forehead, and jaw, human faces are estimated to be capable of more than ten thousand different expressions. In addition many emotions, including happiness, sadness, anger, fear, surprise, disgust, shame, anguish and interest are universally recognized. Display of emotions can generally be categorized into two groups: negative and positive. Negative emotions usually manifest as increased tension in various muscle groups: Tightening of jaw muscles, furrowing of forehead, squinting eyes, or lip occlusion. In contrast, positive emotions are revealed by the loosening of the furrowed lines on the forehead, relaxation of the muscles around the mouth, and widening of the eye area. Some hand movements are not considered to be gestures like scratching, fidgeting, rubbing or tapping. These hand movements may serve as the basis for dispositional inferences of the user's emotion (nervous, uncomfortable, bored). Eye contact is the primary non-verbal way of indicating engagement, interest, attention and involvement. Disinterest is highly noticeable when little or no eye contact is made in a social setting. When an individual is interested, however, the pupils will dilate. In addition non-verbal cues can consist of physiological aspects including pulse rate as well as levels of perspiration. Eye contact and facial expressions provide important social and emotional information.

The present invention further relates to a visualized virtual agent configured to provide an artificial physiological color change response to a user for at least one visualized virtual agent state and/or for at least one state of the user, wherein the visualized virtual agent is configured to provide a visual response to a user, wherein the at least one visualized virtual agent state and/or the state of the user is determined on the basis of activity data of the user and/or of physio-psychological data of the user and wherein the visualized virtual agent is configured to adapt the visual response to changes of the activity data of the user and/or the physio-psychological data of the user, wherein the adaption of the visual response comprises at least in part a color change of the visualized virtual agent for the at least one visualized virtual agent state and/or the at least one state of the user, wherein the physio-psychological data of the user are based on a present behavior (non-verbal behavior) and/or a current physiological condition and/or a current mental state (psychological state) and/or medical condition of the user.

The present invention further relates to a visualized virtual agent configured to provide an artificial physiological color change response to a user for at least one visualized virtual agent state and/or for at least one state of the user, wherein the visualized virtual agent is configured to provide a visual response to a user, wherein the at least one visualized virtual agent state and/or the state of the user is determined on the basis of activity data of the user and/or of physio-psychological data of the user and wherein the visualized virtual agent is configured to adapt the visual response to changes of the activity data of the user and/or the physio-psychological data of the user, wherein the adaption of the visual response comprises at least in part a color change of the visualized virtual agent for the at least one visualized virtual agent state and/or the at least one state of the user, wherein the physio-psychological data of the user are based on a present behavior (non-verbal behavior) and/or a current physiological condition and/or a current mental state (psychological state) and/or medical condition of the user, wherein the visual response comprises a posture, and/or a motion of the visualized virtual agent and wherein the audio response comprises a sound, a sound volume, an emphasis, and/or an accent of the visualized virtual agent on the basis of the activity data of the user and/or physio-psychological of the user.

The visualized virtual agent may be configured to receive user-specific data for one or more user-specific parameter for activity data of a user and/or physio-psychologic data of a user from one or more input devices or one or more sensors. The visualized virtual agent may be configured to acquire user-specific data for one or more user-specific parameter for activity data of a user and/or physio-psychologic data of a user using at least one sensor. The one or more input devices or one or more sensors may be wired or wirelessly connected to the visualized virtual agent. Therefore the visualized virtual agent may be connected to at least one input device and/or at least one sensor for recognizing and/or measuring physio-psychologic parameters of the user by speech recognition, face recognition, measurement of pulse, measurement of breathing, measurement of blood pressure and/or measurement of the electric conductivity of the skin. The one or more sensors may be configured to transmit user-specific data for one or more user-specific parameter for activity data of user and/or physio-psychological data of a user to the visualized virtual agent. The virtual agent may be further configured to store said transmitted user-specific data relating to activity data of a user and/or physio-psychological data of a user in a user-specific database and/or a memory and/or a storage device. The visualized virtual agent may be configured to receive user-specific data as input data relating to activity data of a user and/or physio-psychological data from one or more input devices or one or more sensors and may be further configured to store the transmitted input data relating to activity data of a user and/or physio-psychological data of a user in a memory and/or a storage device and/or a server. The visualized virtual agent may be further configured to generate a user-specific database wherein the transmitted input data relating to activity data of the user and/or physio-psychological data of the user may be stored. On the basis of the transmitted input data relating to activity data of a user and/or physio-psychological data of a user from one or more input devices or one or more sensors, the visualized virtual agent may be configured to provide a visual response comprising at least in part a color change of the visualized virtual agent to the user based on these transmitted user-specific data in form of input data relating to activity data of a user and/or physio-psychological data of a user and/or stored input data relating to activity data of a user and/or physio-psychological data of a user. For example in case the visualized virtual agent acquires user-specific data for at least one user-specific parameter which may relate to activity data of a user and/or physio-psychological data of a user from a sensor which may be configured to monitor the pulse rate of a user, the visualized virtual agent may be configured to generate a visual response comprising at least in part a color change of the visualized virtual agent based on the pulse rate of the user. After generating the visual response comprising at least in part on a color change of the visualized virtual agent on the basis of the transmitted user-specific data relating to activity data of a user and/or physio-psychological data of a user from one or more sensors, the visualized virtual agent may be further configured to cause and render presentation of the generated visual response comprising at least in part a color change of the visualized virtual agent on a display device. The visualized virtual agent may be further configured to cause and render presentation of the generated visual response comprising at least in part a color change of the visualized virtual agent on several display devices. Therefore the visualized virtual agent may be configured to generate a visual response comprising at least in part a color change of the visualized virtual agent to one or more display devices.

Examples of sensors may include a heart rate sensor, a blood pressure sensor/monitor, a weight scale, motion sensors, an optical sensor, a video sensor, an audio sensor, a blood glucose monitor, a blood oxygen saturation monitor, a hydration monitor, a skin/body temperature thermometer, a respiration monitor, electroencephalogram (EEG) electrodes, bed sensors, accelerometer, activity sensors/trackers, and/or other sensors, a video camera e.g. web cam, a depth sensor, electro dermal activity (EDA) sensor, portable global positioning system (GPS) sensor that tracks the location of the user over time, in real time or in near real time. The sensors may be configured to generate any output signals related to input data relating to activity data of a user and/or physio-psychological data of a user that allows the visualized virtual agent or computing system for generating a visualized virtual agent providing an artificial physiological color change response to a user to function as described herein. The one or more sensors may be disposed in a plurality of locations within or outside of the computing system. For example the one or more sensors may be attached to the user, coupled with the user interface, located in a medical device used by the user, positioned to point at the user like a video camera, and/or in other locations within or outside of the system. The one or more sensors may be configured to capture facial expressions of the user, location of the user, posture of the user, voice of the user, electrodermal activity of the user etc. The visualized virtual agent may be configured to determine values indicative of valence, arousal, and engagement of the user, based upon the input data relating to activity data of a user and/or physio-psychological data of a user acquired from the one or one or more sensors, which may be monitored over time or in real time or near real time. Input data relating to activity data of a user and/or physio-psychological data of a user from the one or more sensors may be transmitted directly or indirectly to a central server or a local server. Input data relating to activity data of a user and/or physio-psychological data of a user from the one or more sensors may be transmitted directly or indirectly in addition to or instead to an electronic device.

The visualized virtual agent may be configured to provide long-term recognizing and/or measuring and/or monitoring of activity parameter and/or physio-psychologic parameter of the user and be configured to provide visual responses comprising at least in part a color change of the visualized virtual agent over time on the basis of input data relating to activity data of the user and/or physio-psychological data of a user which may represent the present behavior and/or the current physical condition and/or the current mental state of the user. For example the visualized virtual agent may provide visual responses comprising at least in part a color change of the visualized virtual agent to the user by monitoring behavior changes.

The visualized virtual agent may be connected to one or more sensors, wherein the one or more sensors are configured to transmit input data relating to activity data of a user and/or physio-psychological data of a user to the visualized virtual agent. The visualized virtual agent may be configured to provide a visual response comprising at least in part a color change of the visualized virtual agent on the basis of said transmitted input data relating to activity data of a user and/or physio-psychological data of a user. For example the visualized virtual agent may be connected to one or more video capturing sensors like one or more cameras. The one or more cameras may be integral parts of several different electronic devices of the user (e.g. smartphone, tablet, PDAs, TV) or be located in other devices of the user (e.g. refrigerator, weighing machine, and the like) or be positioned at specific positions in a room (e.g. living room, bedroom and/or kitchen) in a user's home. The visualized virtual agent may be further connected to one or more audio sensors like one or more microphones. The one or more microphones may be an integral part of several different electronic devices of the user (e.g. smartphone, tablet, PDAs, TV) or be located in other devices of the user (e.g. refrigerator, weighing machine, and the like) or be positioned at specific positions in a room (e.g. living room, bedroom and/or kitchen) in a user's home. The visualized virtual agent may be further connected to a portable global positioning system (GPS) sensor, which may transmit tracking data of the user's position to the visualized virtual agent. The visualized virtual agent may be further connected to other suitable input devices and/or sensors. The virtual agent may be configured to provide a visual response comprising at least in part a color change of the visualized virtual agent in connection with the transmitted input data relating to activity data of a user and/or physio-psychological data of a user. For example, the visualized virtual agent may be configured to receive data related to the facial expression of a user, which may be transmitted by the one or more sensors, e.g. the one or more cameras to the visualized virtual agent. The visualized virtual agent may then provide a visual response comprising at least in part a color change of the visualized virtual agent on the basis of the monitored facial expressions of the user. The visualized virtual agent may be further configured to receive input data related to the facial expressions of a user from one or more sensors over time, e.g. from the one or more cameras. The visualized virtual agent of the present invention is therefore further configured to generate output signals to provide a visual response comprising at least in part a color change of the visualized virtual agent and be further configured to transmit said output signals to one or more output devices, e.g. one or more display devices and/or one or more microphones.

The present invention further relates to a visualized virtual agent configured to provide an artificial physiological color change response to a user for at least one visualized virtual agent state and/or for at least one state of the user, wherein the visualized virtual agent is configured to provide a visual response to a user, wherein the at least one visualized virtual agent state and/or the state of the user is determined on the basis of activity data of the user and/or of physio-psychological data of the user and wherein the visualized virtual agent is configured to adapt the visual response to changes of the activity data of the user and/or the physio-psychological data of the user, wherein the adaption of the visual response comprises at least in part a color change of the visualized virtual agent for the at least one visualized virtual agent state and/or the at least one state of the user, wherein the physio-psychological data of the user are based on a present behavior (non-verbal behavior) and/or a current physiological condition and/or a current mental state (psychological state) and/or medical condition of the user, wherein the visualized virtual agent is displayed two dimensionally or three dimensionally on a display device, wherein the visual response comprises a posture, and/or a motion of the visualized virtual agent and wherein the audio response comprises a sound, a sound volume, an emphasis, and/or an accent of the visualized virtual agent on the basis of the activity data of the user and/or physio-psychological of the user, wherein the at least one sensor is configured to acquire physio-psychologic parameters of the user by speech recognition, face recognition, measurement of pulse, measurement of breathing, measurement of blood pressure, and/or measurement of the electric conductivity of the skin, wherein the at least one sensor comprises audio-visual sensors, activity sensors, physiological sensors, biometric sensors, a heart rate sensor, a blood pressure sensor/monitor, a weight scale, motion sensors, an optical sensor, a video sensor, an audio sensor, a blood glucose monitor, a blood oxygen saturation monitor, a hydration monitor, a skin/body temperature thermometer, a respiration monitor, electroencephalogram (EEG) electrodes, bed sensors, accelerometer, activity sensors/trackers, a video camera, a depth sensor, an electro dermal activity (EDA) sensor, a portable global positioning system (GPS) sensor, a microphone.

The visualized virtual agent of the present invention may be rendered and presented on a display device. The visualized virtual agent may provide visual responses combined with audio responses not solely in written form or spoken words, furthermore by specific virtual visual appearances of said visualized virtual agent. Thus the visualized virtual agent may be represented graphically with a visual virtual body and can be configured to interact with a user in verbal and non-verbal manners. In this connection interactions with a user in verbal manners may relate to audio responses in form of oral responses provided by the visualized virtual agent and interactions with a user in non-verbal manners may relate to visual responses in form of body language responses provided by the visualized virtual agent. A visualized virtual agent comprising, for example, means of speech recognition and non-verbal behavior recognition can be configured to respond to verbal and non-verbal communications from the user. For example, a visualized virtual agent may be configured to respond in non-verbal manners characterized by showing expressions or gestures on the basis of the present behavior and/or the current physical condition and/or the current mental state of the user. The visualized virtual agent may further comprise additional means for recognizing specific conditions of a user, like for example means for recognizing an emotional state of a user in order to provide emotional oral responses and emotional body language responses to a user. Therefore the visualized virtual agent may be configured to provide expressions or gestures adapted to the user's emotional state, emotions or mood. Therefore the visualized virtual agent may be configured to provide simulated emotions.

In order to provide a visual virtual appearance of the visualized virtual agent to the user a suitable display device may be connected to the visualized virtual agent, which may be configured to cause presentation of the visualized virtual agent on said display device. The display device may be configured to provide a two dimensionally or a three dimensionally visual representation of the visualized virtual agent. Therefore the visualized virtual agent may be displayed two dimensionally or three dimensionally by the display device. The display device may comprise for example a graphical user interface, a display, a touchscreen, and/or other devices. The display device may include monitors, mobile communication devices, user information systems, and/or other graphic or electronic displays. The display device may be configured to receive generated visual signals and to render and cause visualization of the visualized virtual agent on the display device. The display may additionally be configured to render and present the visualized virtual agent together with other information. The display may be included in a user interface or the user interface may be the display. The display device may be configured to receive generated visual and/or audio signals directly from the processor. The display device may be configured to receive generated visual and/or audio signals based on an emotional state of a user and/or a present behavior and/or a current physical condition and/or the current mental state of the user and to render and cause visualization of the visualized virtual agent in order to provide an emotional body language response combined with an emotional oral response to a user.

The ability to mimic another person's actions allows a person to establish a sense of empathy and thus begin to understand another person's emotions. Mirroring can establish rapport with the individual who is being mirrored, as the similarities in nonverbal gestures allow the individual to feel more connected with the person exhibiting the mirrored behavior. As the two individuals in the situation display similar nonverbal gestures, they may believe that they share similar attitudes and ideas as well. Mirror neurons react to and cause these movements, allowing the individuals to feel a greater sense of engagement and belonging within the situation. Mirroring is common in conversation, as the listeners will typically smile or frown along with the speaker, as well as imitate body posture or attitude about the topic. Individuals may be more willing to empathize with and accept people whom they believe hold similar interests and beliefs, and thus mirroring the person with whom one is speaking may establish connections between the individuals involved. Individuals with autism or other social difficulties may be less likely to exhibit mirroring, as they may be less subconsciously and consciously ware of the action of others. This factor may cause additional difficulties for the individuals, as without mirroring, establishing connections with other people may be more difficult. Additionally, other individuals may be less likely to build rapport with the person, as without mirroring the person may seem more dissimilar and less friendly. Individuals who are not subconsciously aware of gesture may have difficulties in social situations, as they may be less able to understand another person's perspective without it being explicitly stated, and thus may not understand covert cues that are often used in the social world. Thus, in one embodiment of the present invention a visualized virtual agent configured to provide a visual response to a first user may be further configured to provide an artificial physiological color change response to a first user for at least one visualized virtual agent state and/or for at least one state of a second user, preferably a current state of the second user, wherein the at least one visualized virtual agent state and/or the at least one state of the second user, preferably the current state of the second user is determined on the basis of user-specific parameter of the second user, wherein the visualized virtual agent is configured to acquire user-specific data of the second user for at least one user-specific parameter of the second user using at least one sensor, the user-specific parameter comprising activity data of the second user and/or physio-psychological data of the second user, and wherein the artificial physiological color change response is provided in response to monitored changes of the acquired user-specific data of the second user for the at least one user-specific parameter of the second user from the activity data of the second user and/or the acquired physio-psychological data of the second user, the artificial physiological color change response comprising at least in part a color change of the visualized virtual agent for the at least one determined visualized virtual agent state and/or determined current state of the second user. The visualized virtual agent may be further configured to provide a visual response to a user through a color change, a color, a posture, and/or a motion of the virtual agent combined with an audio response through a sound, a sound volume, an emphasis, and/or an accent of the visualized virtual agent based on a present behavior and/or a current physical condition and/or a current mental state of the user to mirror the user's behavior.

The present invention further relates to a visualized virtual agent configured to provide a visual response to a user through a color change, a color, a posture, and/or a motion of the virtual agent combined with an audio response through a sound, a sound volume, an emphasis, and/or an accent of the visualized virtual agent based on a present behavior and/or a current physical condition and/or a current mental state of the user.

The present invention relates to a visualized virtual agent configured to provide a visual response to a user which may be configured to provide an artificial physiological color change response to a user. A specific display device may comprise a specific value of pixels, depending of for example, a native resolution of a display. A color change response and thus an artificial physiological color change response may be generated by a specific change of the pixel color depending on a monitored change of user-specific data for at least one user-specific parameter, like activity data of a user and/or physio-psychological data of a user. Most modern computers have bitmapped displays, where each on-screen pixel directly corresponds to a small number of bits in memory. The screen is refreshed simply by scanning through pixels and coloring them according to each set of bits. The refresh procedure, being speed critical, is often implemented by dedicated circuitry, often as a part of a graphics processing unit. Thus a pixel may serve as an artificial chromatophore to provide an artificial physiological color change response to a user. Thus, the color value for each pixel may be dependent of one or more user-specific parameter relating to activity data of a user and/or physio-psychological data of a user. The color value may change depending on a monitored change of one or more user-specific parameter of activity data of a user and/or physio-psychological data of a user. For example user-specific data of one or more user-specific parameter may be acquired by using at least one sensor. In one embodiment user-specific parameter of only one user-specific parameter may be acquired by at least one sensor. Thus the visualized virtual agent may be configured to provide an artificial physiological color change response to a user based on said user-specific data of the one user-specific parameter. The visualized virtual agent may be configured to determine specific color values relating to one or more user-specific parameter. Thus the visualized virtual agent may be configured to analyze the acquired user-specific data of one or more user-specific parameter and then to determine specific color values for the one or more user-specific parameter based on the acquired user-specific data, which may be acquired by using at least one sensor. Each specific determined color value may relate to a specific output of color and thus the visualized virtual agent may be configured to generate a visual response comprising at least in part a color change of the visualized virtual agent, wherein the color change may relate to an adaption and/or a change of the color of the visualized virtual agent by applying the determined color value and thus to a determined color for the visualized virtual agent, which may be determined based on user-specific data of one or more user-specific parameter, wherein the one or more user-specific parameter may comprise activity data of a user and/or physio-psychological data of a user. The visualized virtual agent may be configured to analyze user-specific data for one or more user-specific parameter and to determine color values over time, in real time or near real time and thus to provide the artificial physiological color change response by automatically applying the determined color values over time, in real time or near real time to the visualized virtual agent. The visualized virtual agent may be configured to analyze acquired user-specific data of one or more user-specific parameter by using at least one sensor and to determine specific color values for the acquired user-specific data of one or more user-specific parameter over time, in real time or in near real time and to adapt the visualized virtual agent automatically over time, in real time or in near real time by applying the determined color value to the visualized virtual agent. The visualized virtual agent may be configured to provide an artificial physiological color change response and thus a visual response comprising at least in part a color change of the visualized virtual agent on an a frame by frame basis.

The intervals between two different color values which may be determined for one or more user-specific parameter which may serve the basis for generating of an artificial physiological color change response of a visualized virtual agent may be different for different user-specific parameter. For example, the user-specific parameter may relate to the body temperature of a user, the interval between two different color values may be set to an interval of $0.1°$ C. In another example the user-specific parameter may relate to the running speed of a user and the interval between two different color values may be set to 0.1 km/h. Thus, the visualized virtual agent may for example acquire user-specific data for the body temperature of a user from a sensor, like a skin temperature sensor which stays in contact with the skin of a user. In this example the visualized virtual agent may determine upon analyzing of the acquired body temperature data of a user that the body temperature of the user has increased by $0.1°$ C. The visualized virtual agent then may determine a specific color value and may generate a visual response comprising at least in part a color change of the visualized virtual agent. Thus after recognizing, analyzing and determining a change of the body temperature of a user based on the acquired body temperature data of a user the visualized virtual agent may generate an artificial physiological color change response to the user, wherein the visualized virtual agent may be presented and outputted on a display device, wherein the presented and rendered visualized virtual agent may be rendered and/or generated on the basis of the determined color value. By defining a color space, colors may be identified numerically by coordinates. The RGB (red-green-blue) color space is a color space corresponding to human trichromacy and to the three cone cell types that responds to three bands of light: long wavelengths, peaking near 564-580 nm (red), medium-wavelength, peaking near 534-545 nm (green) and short wavelength, peaking near 420-440 nm (blue). There may also be more than three color dimension in other color spaces, such as in the CMYK color model, wherein one of the dimensions relates to a color's colorfulness. The CMYK color model is a subtractive color model, particularly used in color printing. A RGB color space is any additive color space based on the RGB color model. A particular RGB color space is defined by the three chromaticities of the red, green, and blue additive primaries. The complete specification of an RGB color space also requires a white point chromaticity and a gamma correction curve. A RGB color can be understood by thinking of it as all possible colors that can be made from three colored lights for red, green, and blue. Each setting of the three colors will produce a different result, either in color or in brightness or both. The set of all possible results is the gamut defined as a certain complete subset of colors in color reproduction, including computer graphics and photography. The most common usage refers to the subset of colors which can be accurately represented in a given circumstance, such as within a given color space or by a certain output device. For example a computer LCD display can be thought of as a grid of millions of little red, green, and blue lamps, each with their own dimmers. The gamut of the display will depend on the three colors used for the red, green, and blue lights. A wide-gamut display will have very saturated, "pure" light colors, and thus be able to display very saturated, deep colors. RGB is a convenient color model for computer graphics because the human visual system works in a way that is similar—though not quite identical—to an RGB color space. The most commonly used RGB color spaces are sRGB and Adobe RGB (which has a significantly larger gamut). As of 2007, sRGB is by far the most commonly used RGB color space, particularly in consumer grade digital cameras, HD video cameras, and computer monitors. HDTVs use a similar space, commonly called Rec. 709, sharing the sRGB primaries. The sRGB space is considered adequate for most consumer applications. Having all devices use the same color space is convenient in that an image does not need to be converted from one color space to another before being displayed. A color may be specified according to the intensity of its red, green and blue components, each represented by eight bits. Thus, there may be 24 bits used to specify a color within a sRGB gamut, and 16,777,216 colors that may be so specified. 24 bits almost always uses 8 bits of each of R, G, B. 24-bit color depth is used by virtually every computer and phone display and the vast majority of image storage formats. Almost all cases where there are 32 bits per pixel mean that 24 are used for the color, and the remaining 8 are the alpha channel or unused. If pixels contain more than 12 bits, an indexed palette takes more memory than the pixels (for typical screen sizes and palette depths), so such systems tend to directly specify the color directly in the pixel.

As an example, the color values for one user-specific parameter may be set to small intervals relating to an one dimensional color gradient scale, for example a vector in a RGB color space. For example a low value of a body temperature may be set to a first color, and a high value of a body temperature of a user may be set to a second color value. By increasing the body temperature from the low value to the a high value the first to second color may be connected through a vector in a RGB color space which may provide an artificial physiological color change response comprising a smooth color change depending on, for example, the acquired body temperature. The sensor acquires the user-specific data for one or more user-specific parameter, for example measures the body temperature of a user over time, in real time or in near real time and for each current acquired temperature value a color value may be determined. The visualized virtual agent then may be configured to adapt the visualized virtual agent at least in part to the determined color value thereby providing an artificial physiological color change response to a user, for example for the current body temperature of a user over time. With other words the acquired user-specific data of one or more user-specific parameter data are used to determine a color valued for generating a determined pixel color on a display device. Thus, the determined color value may be applied for the setting a color of a pixel based on user-specific data of one or more user-specific parameter. The visualized virtual agent may be configured to acquire user-specific data of one or more user-specific parameter, for example of two user-specific parameter or three user-specific parameter and so on by using one or more sensors. Thus, the color value determination may be based on analyzing the two user-specific parameter or the three user-specific parameter. For example the values for these two user-specific parameter or three user-specific parameters and so on may be determined by using a RGB color model to determine color values. The visualized virtual agent may then adapt the visualized virtual agent at least in part to said determined color value. Devices are known in the art which can provide a color change effect to users. For example, thermochromism is the property of substances to change color due to a change in temperature. One popular thermochromism device is a so called "mood ring". A mood ring is a ring that contains a thermochromic element, such as liquid crystal, that changes colors based upon the temperature of the finger of the wearer. Changes in temperature cause the crystal of a mood ring to reflect different wavelengths of light which changes the color of the stone. Thus, the determination of color values for providing an artificial physiological color change response may be based on such a thermochromism material. For example, the visualized virtual agent is configured to provide an artificial physiological color change response to a user based on user-specific data of one or more user-specific parameter, wherein the user-specific parameter is a body temperature of a user, the determined color values for the acquired body temperature data using for example a skin temperature sensor, may be based on a specific color of a thermochromism material, which the thermochromism material provide for a specific temperature.

The visualized virtual agent may be configured to provide an artificial physiological color change response, whereby the visual response comprises at least in part a color change of the visualized virtual agent. In one embodiment the artificial physiological color change response comprises a color change of the visualized virtual agent. In another embodiment the artificial physiological color change response may comprise a color change of 10% of the visualized virtual agent, for example of 10% of the pixels representing the visualized virtual agent. In one embodiment the visualized virtual agent may be rendered with a first color for a first color value and may be rendered with a second color for a second color value. The visualized virtual agent may be configured to provide a color change response comprising at least in part a color change of the visualized virtual agent in the range between the first color value and the second color value, wherein the range between the first color value and the second color value may be subdivided into 10 small intervals, wherein for each interval and subsequent interval a specific amount of the pixel may be adapted to the second color value. For example, the visualized virtual agent may be rendered with the first color by 100% of the pixel of the visualized virtual agent. For each of the 10 small intervals in the range between the first and the second color value, 10% of the pixels add up and are rendered with the second color until reaching the second color value, where 100% of the pixels of the visualized virtual agent may be rendered with the second color. In a further embodiment the range between two color values for one or more user-specific parameter may be subdivided to predefined intervals relating to a one dimensional color gradient scale from a color value 1 to a color value 2. For example, the range between two color values may be subdivided into 10 intervals. The color for the first interval may be a color value 1a, the color of the second interval may be a color value 1b, and so on as color value 1c, 1d, 1e, 1f, 1g, 1h, 1i, 1j. In this example the color value 1j corresponds to the color value 2. Thus, the artificial physiological color change response may comprise a color change of 10% of the visualized virtual agent, for example of 10% of the pixels representing the visualized virtual agent. For a color change of 10% of the visualized virtual agent, 10% of the visualized virtual agent is rendered with color value 1c, whereas the remaining 90% of the visualized virtual agent, for example the remaining 90% of the pixels are rendered with the color value 1. The color change may proceed in that 10% of the pixels add up for each interval. Thus, a further color change of 10% of the visualized virtual agent may correspond to rendering 20% of the visualized virtual agent with the color value 1b, whereas the remaining 80% are rendered with the color value 1. However, a further color change of 10% of the visualized virtual agent may correspond in that the 10% of the visualized virtual agent which are rendered with the color value 1a are again rendered with the color value 1.

Referring now to FIG. 15 examples of color gradients will be described. In FIG. 15 a color value 1 is provided and a color value 2 is provided. The color change to color value 1 to color value 2 may be provided as color gradient from color value 1 to color value 2, for example, defined by the RGB color model. Color value 1 may be assigned to a first color vector in the RGB color model and color value 2 may be assigned to a second color vector in the RGB color model. The gradient may be provided by a connection, such as a by a straight or other function. In FIG. 15b the range between the color values 1 and color value is subdivided into seven segments as an example. By determining a color change the color of the visualized virtual agent may change from color value 1 to color value 1a. After a certain period of time the color of the visualized virtual agent may change from the color value 1a into color value 1b etc. until the color of the visualized virtual agent changes to the color value 2. In FIG. 15c the change of color from color value 2 to color value 1 is shown. Thus, the color change of the visualized agent may include a color change from a color value 1 to a color value 2, but may further include a color change back from color value 2 to color value 1.

In FIG. 16 a schematic example of an artificial physiological color change response is illustrated. On the left side of FIG. 16 display 107, 207, 307, 407, 507 is shown. The display comprises 10×10 pixels in this example. On the display 107, 207, 307, 407, 507 on the left side 100% of the pixels are rendered with pixel color 1. On the right side of FIG. 16 a color change response is illustrated. As illustrated 10 of the pixels, thus 10% of the pixels are rendered with pixel color 2, whereas the remaining 90 of the pixel are rendered with pixel color 1.

In FIG. 17 a further schematic example of an artificial physiological color change response of the visualized virtual agent is illustrated. On the display 107, 207, 307, 407, 507 on the left side already 25% of the pixels are rendered with pixel color 2, whereas the remaining 75% of the pixels are rendered with pixel color 1. On the display 107, 207, 307, 407, 507 on the right side 50% of the pixel are rendered with pixel color 2, whereas the remaining 50% are rendered with pixel color 1. Thus in FIG. 17 a color change response is demonstrated, wherein the color change include a color change of 25% of the pixels from color value 1 to color value 2.

In FIG. 18 a further schematic example of an artificial physiological color change response of the visualized virtual agent is illustrated. At time t0 100% of the pixels of display 107, 207, 307, 407, 507 are rendered with pixel color 1. At the time t1 10% of the pixels are rendered with pixel color 2. At time t2 in total 20% of the pixels are rendered with pixel color 2. At time t3 in total 30% of the pixels are rendered with pixel color 2. At the time t10 100% of the pixels are rendered with pixel color 2. This, schematic examples demonstrates the provision of an artificial physiological color change response over a period of time. The period of time is defined by a start time t0 and an end time tn. The period of time is subdivided into two or more segments. The segments may include years, months, days, hours, minutes, seconds and so on, for example 1, 2, 3 or 4 days, 1, 2, 3 or more months, 1, 2, 4, 5 hours, 1, 2, 3, 4,5 minutes, 1, 2, 3, 4, 5 seconds.

Referring now to FIG. 19 a further schematic illustration of a visualized virtual agent rendering component 106, 206, 306, 406 of systems 100, 200, 300, 400 is demonstrated. The visualized virtual agent rendering component 106, 206, 306, 406 may comprise a value to color (RGB) converter. The user-specific data analysis component may provide the user-specific data for one or more user-specific parameter to the visualized virtual agent rendering component 106, 206, 306, 406. The one or more user-specific parameter may relate to a selection of one or more user-specific parameter determined by the user-specific parameter selection component 215, 315, 415. The values of the user-specific parameter provided to the visualized virtual agent rendering component 106, 206, 306, 406 may be converted into color values for providing an artificial physiological color change response and thus at least in part a color change of the visualized virtual agent. The determined color values from the value to color (RGB) converter are used for rendering and providing the visualized virtual agent on the display device 107, 207, 307, 407. As shown in FIG. 19 10% of the pixels of display 107, 207, 307, 407 are rendered with a pixel color 2, whereas 90% of the pixels are rendered with pixel color 1.

In a preferred embodiment of the present invention the visualized virtual agent may provide an alarm message, for example, an audio signal may generated as output or a text message or visual message may be provided to the user after the 100% of the pixels are rendered in the second color value or after 100% of the visualized virtual agent is rendered with the second color value.

As mentioned above the visualized virtual agent may be configured to provide long-term recognizing and/or measuring and/or monitoring of activity parameter and/or physio-psychologic parameter of the user and be configured to provide visual responses comprising at least in part a color change of the visualized virtual agent over time on the basis of input data relating to activity data of the user and/or physio-psychological data of a user which may represent the present behavior and/or the current physical condition and/or the current mental state of the user. For example the visualized virtual agent may provide visual responses comprising at least in part a color change of the visualized virtual agent to the user by monitoring behavior changes.

In preferred embodiments the color change may be provided over a predefined period of time. For example, a visualized virtual agent may be rendered and displayed with a first color, after monitored changes of activity data and/or physio-psychological data of a user the visualized virtual agent may provide a color change response to the user by rendering 100% of the visualized virtual agent with a second color, for example, directly or immediately after determining a monitored change of activity data and/or physio-psychological data of a user. It is preferred that the color change response provided by the visualized virtual agent comprises a color change of a part of the visualized virtual agent. It is further preferred that color change of the visualized virtual agent proceeds in that after a predefined period of time the visualized virtual agent may be fully rendered with a second value.

For example, as illustrated in FIG. 20, the visualized virtual agent may provide an artificial physiological color change response to a user while the user is driving a car. In this example, the visualized virtual agent preferably determines a current state of the user, which may relate to a driving state of the user. In preferred embodiments a user-specific parameter selection component may determine one or more user-specific parameters which are suitable for providing an artificial physiological color change response to the user for the driving state of the user. The user-specific parameter for a driving state of a user may be for example, the duration of driving the car and a blink rate of a user. The blink rate of a user may be captured by one or more cameras. The blink rate of the user may indicate the tiredness of the user. The duration of driving the car may be captured by a GPS sensor which may detect that the user is still driving the car or if the user stops driving the car. The GPS sensor and the one or more cameras may collect user-specific data and based on the acquired sensor data the user-specific data analysis component may determine if the user stops in order to take a break, for example, by getting of the car. Initially, the visualized virtual agent determines a change of monitored user-specific data and/or physio-psychological data at the moment the user start driving the car and determines the driving state of the user as the current state of the user. This may result in rendering the visualized virtual agent with a first color value. As shown in FIG. 20 the display 107, 207, 307, 407, 507 comprises 10×10 pixels which are rendered with the first color value. When the user begins driving the car a color change may be provided by the visualized virtual agent. For example, 10% of the pixels may be rendered with a second color value. As shown in FIG. 20 based on the duration of driving the car and the blink rate of the user already 20% of the pixels are rendered with the second pixel color. After a period of time, at the point in time t10, 100% of the pixel may be rendered with the second pixel color value. In this way, a color change response may be provided to the user based on the user tiredness.

The present invention further relates to a computing device for generating a visualized virtual agent configured to provide a visual response to a user which is further configured to provide an artificial physiological color change response to a user on the basis of user-specific parameter, wherein the visualized virtual agent is configured to acquire user-specific data for at least one user-specific parameter using at least one sensor, the user-specific parameter comprising activity data of the user and/or physio-psychological data of the user, and wherein the artificial physiological color change response is provided in response to monitored changes of the acquired user-specific data for the at least one user-specific parameter from the activity data of the user and/or the physio-psychological data of the user, the artificial physiological color change response comprising at least in part a color change of the visualized virtual agent, the computing device comprising:

- at least one memory for storing computer readable instructions for generating of the visualized virtual agent
- at least one processor for generating the visual response and audio response of the visualized virtual agent, and
- at least one sensor for acquiring user-specific data for one or more user specific-parameter for activity data of the user and/or physio-psychologic data of the user by speech recognition, face recognition, measurement of pulse, measurement of breathing, measurement of blood pressure, and/or measurement of the electric conductivity of the skin, and
- at least one output device for presenting the generated visual response.

The present invention further relates to a computing device for generating a visualized virtual agent configured to provide an artificial physiological color change response to a user for at least one visualized virtual agent state and/or for at least one state of the user, wherein the visualized virtual agent is configured to provide a visual response to a user, wherein the at least one visualized virtual agent state and/or the state of the user is determined on the basis of activity data of the user and/or of physio-psychological data of the user and wherein the visualized virtual agent is configured to adapt the visual response to changes of the activity data of the user and/or the physio-psychological data of the user, wherein the adaption of the visual response comprises at least in part a color change of the visualized virtual agent for the at least one visualized virtual agent state and/or the at least one state of the user, the computing device comprising:

- at least one memory for storing computer readable instructions for generating of the visualized virtual agent
- at least one processor for generating the visual response and audio response of the visualized virtual agent, and
- at least one sensor for acquiring user-specific data for one or more user specific-parameter for activity data of the user and/or physio-psychologic data of the user by speech recognition, face recognition, measurement of pulse, measurement of breathing, measurement of blood pressure, and/or measurement of the electric conductivity of the skin, and
- at least one output device for presenting the generated visual response.

The present invention further relates to a computing device for generating a visualized virtual agent configured to provide an artificial physiological color change response to a user for at least one visualized virtual agent state and/or for at least one state of the user, wherein the visualized virtual agent is configured to provide a visual response to a user, wherein the at least one visualized virtual agent state and/or the state of the user is determined on the basis of activity data of the user and/or of physio-psychological data of the user and wherein the visualized virtual agent is configured to adapt the visual response to changes of the activity data of the user and/or the physio-psychological data of the user, wherein the adaption of the visual response comprises at least in part a color change of the visualized virtual agent for the at least one visualized virtual agent state and/or the at least one state of the user, the computing device comprising:
- at least one memory for storing computer readable instructions for generating of the visualized virtual agent
- at least one processor for generating the visual response and audio response of the visualized virtual agent, and
- at least one storage device for storing user-specific input data, and
- at least one sensor for acquiring user-specific data for one or more user specific-parameter for activity data of the user and/or physio-psychologic data of the user by speech recognition, face recognition, measurement of pulse, measurement of breathing, measurement of blood pressure, and/or measurement of the electric conductivity of the skin, and
- at least one output device for presenting the visual response.

The present invention further relates to a computing device for generating to a visualized virtual agent configured to provide a visual response to a user which is further configured to provide an artificial physiological color change response to a user for at least one visualized virtual agent state and/or for at least one state of the user, preferably a current state of the user, wherein the at least one visualized virtual agent state and/or the at least one state of the user, preferably the current state of the user is determined on the basis of user-specific parameter, wherein the visualized virtual agent is configured to acquire user-specific data for at least one user-specific parameter using at least one sensor, the user-specific parameter comprising activity data of the user and/or physio-psychological data of the user, and wherein the artificial physiological color change response is provided in response to monitored changes of the acquired user-specific data for the at least one user-specific parameter from the activity data of the user and/or the acquired physio-psychological data of the user, the artificial physiological color change response comprising at least in part a color change of the visualized virtual agent for the at least one determined visualized virtual agent state and/or determined current state of the user, the computing device comprising:
- at least one memory for storing computer readable instructions for generating of the visualized virtual agent
- at least one processor for generating the visual response and audio response of the visualized virtual agent, and
- at least one storage device for storing user-specific data, and
- at least one sensor for acquiring user-specific data for one or more user specific-parameter for activity data of the user and/or physio-psychologic data of the user by speech recognition, face recognition, measurement of pulse, measurement of breathing, measurement of blood pressure, and/or measurement of the electric conductivity of the skin, and
- at least one output device for presenting the visual response.

The present invention further relates to a computing device for generating a visualized virtual agent configured to provide a visual response to a user and configured to monitor over time one or more user-specific parameter, wherein user-specific data for at least one user-specific parameter are acquired by at least one sensor, the user-specific parameter comprising activity data of the user and/or physio-psychological data of the user, wherein the visualized virtual agent is configured to provide an artificial physiological color change response to a user for at least one visualized virtual agent state and/or for a current state of the user, wherein the at least one visualized virtual agent state and/or the current state of the user is determined on the basis of the activity data of the user and/or of the physio-psychological data of the user; wherein the visualized virtual agent is configured to adapt the artificial physiological color change response to monitored changes of the activity data of the user and/or the physio-psychological data of the user, wherein the adaption of the artificial physiological color change response comprises at least in part a color change of the visualized virtual agent for the at least one visualized virtual agent state and/or the current state of the user,
- at least one memory for storing computer readable instructions thereon for generating of the visualized virtual agent;
- at least one processor for generating the artificial physiological color change response of the visualized virtual agent, and
- at least one sensor for acquiring user-specific data for one or more user specific-parameter for activity data of the user and/or physio-psychologic date of a user, and
- at least one output device for presenting the generated visual response.

The computing device may comprise an electronic device. Examples of electronic devices may include any portable, mobile, hand-held or miniature consumer electronic device. Further examples of electronic devices are music players, video players, still image players, game players, other media players, music recorders, video recorders, cameras, other media recorders, radios, medical equipment, calculators, cellular phones, other wireless communication devices, personal digital assistances, programmable remote controls, pagers, laptop computers, printers, or combinations thereof. Further examples of miniature electronic devices are watches, rings, necklaces, belts, accessories for belts, headsets, accessories for shoes, virtual reality devices, other wearable electronics, accessories for sporting equipment, accessories for fitness equipment, key chains, or combinations thereof. Other devices may include a personal computer, a mainframe computer, a laptop computer, a tablet computer, a cell phone, a smartphone, a smartwatch, a personal digital assistant (PDA) and/or an e-reader device.

The present invention further relates to a computer-implemented method for generating a visualized virtual agent configured to provide a visual response to a user which is further configured to provide an artificial physiological color change response to a user on the basis of user-specific parameter, wherein the visualized virtual agent is configured to acquire user-specific data for at least one user-specific parameter using at least one sensor, the user-specific parameter comprising activity data of the user and/or physio-psychological data of the user, and wherein the artificial physiological color change response is provided in response to monitored changes of the acquired user-specific data for the at least one user-specific parameter from the activity data of the user and/or the physio-psychological data of the user, the artificial physiological color change response comprising at least in part a color change of the visualized virtual agent.

The present invention further relates to a computer-implemented method for generating a visualized virtual agent configured to provide a visual response to a user and which is further configured to provide an artificial physiological color change response to a user for at least one visualized virtual agent state and/or for at least one state of the user, preferably a current state of the user, wherein the at least one visualized virtual agent state and/or the at least one state of the user, preferably the current state of the user is determined on the basis of user-specific parameter, wherein the visualized virtual agent is configured to acquire user-specific data for at least one user-specific parameter using at least one sensor, the user-specific parameter comprising activity data of the user and/or physio-psychological data of the user, and wherein the artificial physiological color change response is provided in response to monitored changes of the acquired user-specific data for the at least one user-specific parameter from the activity data of the user and/or the acquired physio-psychological data of the user, the artificial physiological color change response comprising at least in part a color change of the visualized virtual agent for the at least one determined visualized virtual agent state and/or determined current state of the use The present invention further relates to a computer-implemented method for generating a visualized virtual agent configured to provide an artificial physiological color change response to a user, the visualized virtual agent may be further configured to provide a visual response comprising at least in part a color change of the visualized virtual agent and may be further configured to provide visual responses combined with audio responses to a user based on user-specific parameter like activity data of a user and/or physio-psychological data of a user, like the present behavior and/or the current physical condition and/or the current mental state of a user, with a system comprising a user interface, one or more hardware processors and a display and a microphone. The method may comprise accessing input data relating to activity data of a user and/or physio-psychological data of a user stored in at least one database and/or in a memory and/or on a storage device. The method may further comprise receiving, with the user interface, input data relating to activity data of a user and/or physio-psychological data of the user, the input data may include input data relating to activity data of a user and/or physio-psychological data of a user, which may be transmitted by at least one input device and/or at least one sensor, the user-specific input data may include one or more of physio-psychologic parameters, information of the current state of the user, information of the current condition of the user and/or information about the current mental state of the user. The method may further comprise determining with the one or more hardware processors a visualized virtual agent state and/or current state of the user. The method may further comprise determining with the one or more hardware processors a visual response comprising at least in part a color change of the visualized virtual agent. The method may further comprise determining visual responses combined with audio responses based on the input data relating to activity data of a user and/or physio-psychological data of a user acquired by using at least one sensor. The method may further comprise generating with the one or more hardware processors visual and audio signals to provide an artificial physiological color change response to a user and a visual response comprising at least in part a color change of the visualized virtual agent and further a visual response combined with an audio response of the visualized virtual agent based on input data relating to activity data of a user and/or physio-psychological data of a user, which have been transmitted by at least one sensor and/or are based on the present behavior and/or the current physical condition and/or the current mental state of the user, wherein the visual response combined with the audio response of the visualized virtual agent may be given in an emotional oral form combined with an emotional body language reflecting the physical condition and the mental state of the user and/or reflecting the emotions and/or mood of the user. The method may further comprise receiving with the display generated visual and/or audio signals and determined visual responses comprising at least in part a color change of the visualized virtual agent combined with audio responses and rendering and causing presentation of the visualized virtual agent on the display and providing the generated artificial physiological color change response to the user and a visual response comprising at least in part a color change of the visualized virtual agent and visual responses combined with audio responses to the user. The method may further comprise determining with the one or more hardware processors a current state (e.g. present behavior, physical condition, mental state) of the user based on an analysis of the acquired sensor data relating to activity data of a user and/or physio-psychological data of a user. The method may further comprise a user interface which may include one or more input devices and/or one or more sensors configured to generate output signals in order to transmit the input data relating to activity data of a user and/or physio-psychological data of a user like related to verbal and non-verbal behavior of the user. The method may further comprise displaying the visualized virtual agent two dimensionally or three dimensionally on a display device.

The present invention further relates to a computer-implemented method for generating a visualized virtual agent configured to provide an artificial physiological color change response to a user for at least one visualized virtual agent state and/or for at least one state of the user, wherein the visualized virtual agent is configured to provide a visual response to a user, wherein the at least one visualized virtual agent state and/or the state of the user is determined on the basis of user-specific parameter including activity data of the user and/or of physio-psychological data of the user, wherein at least one user-specific parameter is acquired by using at least one sensor, and wherein the visual response is depending on changes of the activity data of the user and/or the physio-psychological data of the user, the visual response comprises at least in part a color change of the visualized virtual agent for the at least one determined visualized virtual agent state and/or the at least one determined state of the user, the method comprising the steps of:
  acquiring, activity data of the user and/or physio-psychological data of the user over time using at least one sensor,
  acquiring, by the processor, activity data of the user and/or a physio-psychological of the user from the at least one sensor
  analyzing, by the processor, the activity data of the user and/or physio-psychological of the user, determining, by the processor, a visualized virtual agent state on the basis of the acquired activity data of the user and/or the acquired physio-psychological of the user, and/or determining, by the processor, a current state of the user on the basis of the received acquired activity data of the user and/or the acquired physio-psychological data of the user, selecting, by the processor, based on the determined current state of the user and/or based on the determined visualized virtual agent state at least one sensor for generating of a color change response rendering, by the graphic processing unit, the visualized virtual agent with a first color for the determined visualized virtual agent state and/or the determined current state of the user, displaying. by at least one display, the visualized virtual agent with the first color for the determined visualized virtual agent state and/or the determined current state of the user on a display device acquiring, by the processor, (in real time) activity data of the user and/or physio-psychological data of the user for the determined visualized virtual agent state and/or current state of the user using the selected at least one sensor, analyzing, by the processor, (in real time) the acquired activity data of the user and/or the physio-psychological of the user from the selected at least one sensor, determining, by the processor, changes of the acquired activity data of the user and/or the acquired physio-psychological of the user, rendering, by the graphic processing unit, the visualized virtual agent with a second color in response to the determined changes of the acquired activity data of the user and/or the acquired physio-psychological of the user displaying, by the display, the visualized virtual agent with the second color device for the determined visualized virtual agent state and/or the determined current state of the user on a display device.

Thus the present invention further relates to a computer-implemented method for generating a visualized virtual agent configured to provide an artificial physiological color change response to a user, the method comprising the following steps:

monitoring over time, by a user-specific parameter monitoring component, one or more user-specific parameter of a user, the one or more user-specific parameter comprising activity data of the user and/or physio-psychological data of the user, acquiring, by the user specific parameter monitoring component, user-specific data for at least one user-specific parameter by at least one sensor, analyzing, by a user-specific data analysis component, the monitored one or more user-specific parameter of the user, determining, by the user-specific data analysis component, monitored changes of the activity data of the user and/or the physio-psychological data of the user, providing, by the user-specific data analysis component, the monitored changes of the activity data of the user and/or the physio-psychological data of the user to a visualized virtual agent rendering component, adapting, by the visualized virtual agent rendering component, the artificial physiological color change response to the monitored changes of the activity data of the user and/or the physio-psychological data of the user, wherein the adaption of the artificial physiological color change response comprises at least in part a color change of the visualized virtual agent, rendering, by the visualized virtual agent rendering component, the visualized virtual agent on a display device.

Thus the present invention further relates to a computer-implemented method for generating a visualized virtual agent configured to provide an artificial physiological color change response to a user, the method comprising the following steps:

monitoring over time, by a processor, one or more user-specific parameter of a user, the one or more user-specific parameter comprising activity data of the user and/or physio-psychological data of the user, acquiring, by a processor, user-specific data for at least one user-specific parameter by at least one sensor, analyzing, by a processor, the monitored one or more user-specific parameter of the user, determining, by a processor, monitored changes of the activity data of the user and/or the physio-psychological data of the user, providing, by a processor, the monitored changes of the activity data of the user and/or the physio-psychological data of the user to a visualized virtual agent rendering component, adapting, by a processor, the artificial physiological color change response to the monitored changes of the activity data of the user and/or the physio-psychological data of the user, wherein the adaption of the artificial physiological color change response comprises at least in part a color change of the visualized virtual agent, rendering, by a graphic processing unit, the visualized virtual agent on a display device.

Thus the present invention further relates to a computer-implemented method for generating a visualized virtual agent configured to provide an artificial physiological color change response to a user, the method comprising the following steps:

monitoring over time, by a user-specific parameter monitoring component, one or more user-specific parameter of a user, the one or more user-specific parameter comprising activity data of the user and/or physio-psychological data of the user, acquiring, by the user specific parameter monitoring component, user-specific data for at least one user-specific parameter by at least one sensor, determining, by a current state of the user determination component, a current state of the user on the basis of the activity data of the user and/or the physio-psychological data of the user and/or determining, by a visualized virtual agent state determination component, a visualized virtual agent state on the basis of the activity data of the user and/or the physio-psychological data of the user, determining, by a user-specific parameter selection component, a selection of one or more user-specific parameter based on the determined current state of the user and/or based on the determined visualized virtual agent state;

analyzing, by a user-specific data analysis component, the monitored one or more user-specific parameter of the user of the determined selection of one or more user-specific parameter, determining, by the user-specific data analysis component, monitored changes of the activity data of the user and/or the physio-psychological data of the user, providing, by the user-specific data analysis component, the monitored changes of the activity data of the user and/or the physio-psychological data of the user to a visualized virtual agent rendering component, adapting, by the visualized virtual agent rendering component, the artificial physiological color change response to the monitored changes of the activity data of the user and/or the physio-psychological data of the user, wherein the adaption of the artificial physiological color change response comprises at least in part a color change of the visualized virtual agent, rendering, by the visualized virtual agent rendering component, the visualized virtual agent on a display device.

Thus the present invention further relates to a computer-implemented method for generating a visualized virtual agent configured to provide an artificial physiological color change response to a user, the method comprising the following steps:

monitoring over time, by a user-specific parameter monitoring component, one or more user-specific parameter of a user, the one or more user-specific parameter comprising activity data of the user and/or physio-psychological data of the user, and acquiring, by the user specific parameter monitoring component, user-specific data for at least one user-specific parameter by at least one sensor;

determining, by a current state of the user determination component, a current state of the user on the basis of the activity data of the user and/or the physio-psychological data of the user and/or determining, by a visualized virtual agent state determination component, a visualized virtual agent state on the basis of the activity data of the user and/or the physio-psychological data of the user;

analyzing, by a user-specific data analysis component, the monitored one or more user-specific parameter of the user for the determined current state of the user and/or determined visualized virtual agent state;

determining, by the user-specific data analysis component, monitored changes of the activity data of the user and/or the physio-psychological data of the user;

providing, by the user-specific data analysis component, the monitored changes of the activity data of the user and/or the physio-psychological data of the user to a visualized virtual agent rendering component;

adapting, by the visualized virtual agent rendering component, the artificial physiological color change response to the monitored changes of the activity data of the user and/or the physio-psychological data of the user, wherein the adaption of the artificial physiological color change response comprises at least in part a color change of the visualized virtual agent;

rendering, by the visualized virtual agent rendering component, the visualized virtual agent on a display device.

Computing systems generally consists of three main parts: the central processing unit (CPU) that processes data, a memory that holds the programs and data to be processed, and I/O (input/output) devices as peripherals that communicate with a user. The present invention further relates to a computing system configured to generate a visualized virtual agent configured to provide an artificial physiological color change response to a user, wherein the visualized virtual agent may be further configured to generate a visual response comprising at least in part a color change of the visualized virtual agent and may be further configured to generate a visual response combined with an audio response of the visualized virtual agent to a user based on user-specific parameter, like activity data of a user and/or psychological data of a user, like the present behavior and/or current physical condition and/or current mental state of the user, the system may comprise a user interface, configured to receive input data relating to activity data of a user and/or physio-psychological data of a user, the input data may include input data relating to activity data of a user and/or physio-psychological data of a user which may be stored in at least one database and/or stored on at least one memory and/or stored in at least one storage device and/or input relating to activity data of a user and/or physio-psychological data of a user which are directly transmitted by at least one input device and/or at least one sensor, the input data may include one or more of physio-psychologic parameters, user-specific data of the present state, user-specific data of the current physiological condition and/or user-specific data about the current mental state of the user. The system may further comprise one or more hardware processors configured by machine-readable instructions to determine an artificial physiological color change response to a user and further configured to provide a visual response comprising at least in part a color change of the visualized virtual agent and may be further configured to determine a visual response combined with an audio response of the visualized virtual agent to the user, wherein the artificial physiological color change response and the visual response combined with the audio response are based on input data relating to activity data of a user and/or physio-psychological data of a user which may be transmitted by at least one input device and/or at least one sensor and/or are based on said transmitted input data relating to activity data of a user and/or physio-psychological data of a user which may be stored in at least one database and/or at least one memory and/or at least one storage device. The one or more hardware processors may be further configured to generate visual and/or audio signals to provide a visual response combined with and audio response of the visualized virtual agent based on the input data relating to activity data of a user and/or physio-psychological data of a user which may be transmitted by at least one input device and/or at least one sensor and/or based on the present behavior and/or the current physical condition and/or the current mental state of the user, wherein the visual response combined with the audio response of the visualized virtual agent may be given in an emotional oral form combined with an emotional body language reflecting the physical condition and/or the mental state of the user, e.g. the users' emotions and/or mood. The visualized virtual agent may therefore be configured to provide an artificial physiological color change response to a user, wherein the visual response comprises at least in part a color change of the visualized virtual agent by reflecting the physical condition and/or the mental state of the user, e.g. the user's emotions and/or mood. The system may further comprise a display device configured to receive the generated visual and/or audio signals of the generated visual response comprising at least in part a color change of the visualized virtual agent combined with the generated audio response and to render and cause presentation of the visualized virtual agent on the display to provide the artificial physiological color change response and thus to provide a visual response comprising at least in part a color change of the visualized virtual agent combined with an audio response to the user. The one or more hardware processors may be further configured to determine a current state (e.g. present behavior, physical condition and/or mental state) of the user based on an analysis of the transmitted input data relating to activity data of a user and/or physio-psychological data of a user which may be received by the user interface. The current state may indicate a physiological state of the user, behavior state of the user, psychological state of the user and/or medical state of the user. The user interface may include one or more input devices and/or one or more sensors configured to generate output signals and configured to transmit input data relating to activity data of a user and/or physio-psychological data of a user like for example related to verbal and non-verbal behavior of the user. The one or more hardware processors may be further configured to extract specific information and/or specific input data from the output signals generated by one or more input devices and/or one or more sensors. The one or more sensors may include one or more of physiological sensors, audio sensors, and or visual sensors.

Thus, the present invention further relates to a system for generating a visualized virtual agent providing an artificial physiological color change response to a user, the system comprising:

a memory;

at least one sensor configured to collect sensor data for at least one user-specific parameter of the user, at least one display device configured to display the visualized virtual agent;

at least one processor configured to execute executable components stored on the memory, the executable components comprising:

a user-specific parameter monitoring component configured to monitor one or more user-specific parameter of the user, wherein the user-specific parameter monitoring component is configured to receive user-specific data for one or more user-specific parameter, the user-specific parameter comprising activity data of the user and/or physio-psychological data of the user, wherein user-specific data for at least one user-specific parameter are acquired from the at least one sensor;

a user-specific data analysis component configured to analyze the user-specific data monitored by the user-specific parameter monitoring component and to determine monitored changes of the activity data of the user and/or physio-psychological data of the user;

a visualized virtual agent rendering component configured to adapt the artificial physiological color change response to the determined monitored changes of the activity data of the user and/or the physio-psychological data of the user, wherein the adaption of the artificial physiological color change response comprises at least in part a color change of the visualized virtual agent.

Thus, the present invention further relates to a system for generating a visualized virtual agent providing an artificial physiological color change response to a user, the system comprising:

a memory;

at least one sensor configured to collect sensor data for at least one user-specific parameter of the user, at least one display device configured to display the visualized virtual agent;

at least one processor configured to execute executable components stored on the memory, the executable components comprising:

a user-specific parameter monitoring component configured to monitor one or more user-specific parameter of the user, wherein the user-specific parameter monitoring component is configured to receive user-specific data for one or more user-specific parameter, the user-specific parameter comprising activity data of the user and/or physio-psychological data of the user, wherein user-specific data for at least one user-specific parameter are acquired from the at least one sensor;

a user-specific data analysis component configured to analyze the user-specific data monitored by the user-specific parameter monitoring component and to determine monitored changes of the activity data of the user and/or physio-psychological data of the user;

a visualized virtual agent rendering component configured to adapt the artificial physiological color change response to the determined monitored changes of the activity data of the user and/or the physio-psychological data of the user, wherein the adaption of the artificial physiological color change response comprises at least in part a color change of the visualized virtual agent;

wherein the user-specific data analysis component further comprises:

a user-specific parameter selection component configured to determine a selection of one or more user-specific parameter from the one or more user-specific parameter as a basis for generating of the artificial physiological color change response.

Thus, the present invention further relates to a system for generating a visualized virtual agent providing an artificial physiological color change response to a user, the system comprising:

a memory;

at least one sensor configured to collect sensor data for at least one user-specific parameter of the user, at least one display device configured to display the visualized virtual agent;

at least one processor configured to execute executable components stored on the memory, the executable components comprising:

a user-specific parameter monitoring component configured to monitor one or more user-specific parameter of the user, wherein the user-specific parameter monitoring component is configured to receive user-specific data for one or more user-specific parameter, the user-specific parameter comprising activity data of the user and/or physio-psychological data of the user, wherein user-specific data for at least one user-specific parameter are acquired from the at least one sensor;

a user-specific data analysis component configured to analyze the user-specific data monitored by the user-specific parameter monitoring component and to determine monitored changes of the activity data of the user and/or physio-psychological data of the user;

a visualized virtual agent rendering component configured to adapt the artificial physiological color change response to the determined monitored changes of the activity data of the user and/or the physio-psychological data of the user, wherein the adaption of the artificial physiological color change response comprises at least in part a color change of the visualized virtual agent;

wherein the user-specific data analysis component further comprises:

a user-specific parameter selection component configured to determine a selection of one or more user-specific parameter from the one or more user-specific parameter as a basis for generating of the artificial physiological color change response;

a current state of the user determination component configured to determine a current state of the user based on the user-specific data monitored by the user-specific parameter monitoring component.

Thus, the present invention further relates to a system for generating a visualized virtual agent providing an artificial physiological color change response to a user, the system comprising:

a memory;

at least one sensor configured to collect sensor data for at least one user-specific parameter of the user, at least one display device configured to display the visualized virtual agent;

at least one processor configured to execute executable components stored on the memory, the executable components comprising:

a user-specific parameter monitoring component configured to monitor one or more user-specific parameter of the user, wherein the user-specific parameter monitoring component is configured to receive user-specific data for one or more user-specific parameter, the user-specific parameter comprising activity data of the user and/or physio-psychological data of the user, wherein user-specific data for at least one user-specific parameter are acquired from the at least one sensor;

a user-specific data analysis component configured to analyze the user-specific data monitored by the user-specific parameter monitoring component and to determine monitored changes of the activity data of the user and/or physio-psychological data of the user;

a visualized virtual agent rendering component configured to adapt the artificial physiological color change response to the determined monitored changes of the activity data of the user and/or the physio-psychological data of the user, wherein the adaption of the artificial physiological color change response comprises at least in part a color change of the visualized virtual agent;

wherein the user-specific data analysis component further comprises:

a current state of the user determination component configured to determine a current state of the user based on the user-specific data monitored by the user-specific parameter monitoring component.

Thus, the present invention further relates to a system for generating a visualized virtual agent providing an artificial physiological color change response to a user, the system comprising:

a memory;

at least one sensor configured to collect sensor data for at least one user-specific parameter of the user, at least one display device configured to display the visualized virtual agent;

at least one processor configured to execute executable components stored on the memory, the executable components comprising:

a user-specific parameter monitoring component configured to monitor one or more user-specific parameter of the user, wherein the user-specific parameter monitoring component is configured to receive user-specific data for one or more user-specific parameter, the user-specific parameter comprising activity data of the user and/or physio-psychological data of the user, wherein user-specific data for at least one user-specific parameter are acquired from the at least one sensor;

a user-specific data analysis component configured to analyze the user-specific data monitored by the user-specific parameter monitoring component and to determine monitored changes of the activity data of the user and/or physio-psychological data of the user;

a visualized virtual agent rendering component configured to adapt the artificial physiological color change response to the determined monitored changes of the activity data of the user and/or the physio-psychological data of the user, wherein the adaption of the artificial physiological color change response comprises at least in part a color change of the visualized virtual agent;

wherein the user-specific data analysis component further comprises:

a user-specific parameter selection component configured to determine a selection of one or more user-specific parameter from the one or more user-specific parameter as a basis for generating of the artificial physiological color change response;

a current state of the user determination component configured to determine a current state of the user based on the user-specific data monitored by the user-specific parameter monitoring component, and/or a visualized virtual agent state determination component configured to determine a visualized virtual agent based on the user-specific data monitored by the user-specific parameter monitoring component.

Preferably the visualized virtual agent rendering component comprises a value to color (RGB) converter.

A computer is a machine that manipulates data according to a set of instructions called a computer program. The program has an executable form that the computer can use directly to execute the instruction. Because the instructions can be carried out in different types of computers, a single set of source instructions converts to machine instructions according to the central processing unit type. The execution process carries out the instructions in a computer program. The computing system may include a processing unit, a system memory, and a system bus. One or more of the processes described herein may be implemented at least in part as instructions embodied in a non-transitory computer-readable medium and executable by one or more computing devices. In general, a processor receives instructions from a non-transitory computer-readable medium and executes those instructions thereby performing one or more processes including one or more of the processes described herein for providing a visualized virtual agent providing an artificial physiological color change response to a user.

The computing system may further include a bus that transfers data between computer components inside the computing device or between one or more computing devices. The system bus couples system components including, but not limited to, the system memory to the processing unit. The system bus may include several forms of bus structures including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), PCI Express (PCI-e), Card Bus, Universal Serial Bus (USB), Advanced Graphics Port (AGP), Personal Computer Memory Card International Association bus (PCMCIA), Firewire (IEEE 104) and Small Computer Systems Interface (SCSI). The internal bus, internal data bus, memory bus, system bus or Front-Side-Bus connects all the internal components of a computer, such as CPU and memory, to the motherboard. Internal data buses are also referred to as a local bus, because they are intended to connect to local devices. The external bus, or expansion bus, is made up of the electronic pathways that connect the different external devices. Buses can be parallel buses or serial buses. A serial bus can be operated at higher overall data rate than a parallel bus. USB, FireWire, Serial ATA Cache is a small, fast local memory that transparently buffers access to a larger but slower or more distant/higher latent.

The computing system may further comprise a computer-readable data storage that is configured with computer-executable instructions that cause certain functionality to be performed when executed by a processor or central processing unit (CPU). The computer-executable instructions may include a routine, a function, or the like. A component of the computing system may be localized on a single computing device or distributed across several computing devices. The system may comprise a user interface configured to receive input information related to the user like user-specific input data. The system may comprise a user interface, one or more sensors, a display, hardware processor(s), electronic storage, external resources and/or other components. One or more components of the system may be communicatively coupled via a network and/or other coupling mechanisms. Computer-readable storage media can include, but are not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or other tangible and/or non-transitory media which can be used to store desired information. Computer-readable storage media can be accessed by one or more local or remote computing devices, e.g. via access requests, queries or other data retrieval protocols, for a variety of operations with respect to the information stored by the medium. Disk storage includes, but is not limited to, devices like magnetic disk drive, solid state disk (SSD), floppy disk drive, tape drive, Jaz drive, Zip drive, LS-70 drive, flash memory card, memory stick. Disk storage can include storage medium separately or in combination with other storage medium including, but not limited to, an optical disk drive such as a compact disk ROM device, (CD-ROM), CD recordable drive (CD-R Drive), CD rewritable drive (CD-RW Drive) or a digital versatile disk ROM drive (DVD-ROM). To facilitate connection of the disk storage devices to the system bus, a removable or non-removable interface is typically used.

The system may further comprise a memory, such as random access memory (RAM) for temporary storage of information and/or a read only memory (ROM) for permanent storage of information, and a mass storage device, such as a hard drive, diskette, or optical media storage device. The components of the system may be connected to the computer using standard based system, which may include peripheral component interconnect (PCI), Microchannel, SCSI, Industrial standard Architecture (ISA), and extended ISA (EISA) architectures. Read only memory (ROM), programmable ROM (PROM), electrically programmable ROM (EEPROM), flash memory. Volatile memory includes random access memory (RAM), which acts as external cache memory. The volatile memory may store the write operation retry logic and the like. RAM is available in many forms such as static RAM (SRAM), dynamic RAM (DRAM), synchronous DRAM (SDRAM) double data rate SDRAM (DDR SDRAM) and enhanced SDRAM (ESDRAM). The system memory includes volatile memory and non-volatile memory. The basic input/output system (BIOS) containing the basic routine to transfer information between elements within the computer, such as during start-up, is stored in non-volatile memory.

The computing system may further comprise at least one processor. The computing system may further comprise at least one processing unit. The one or more processors may be configured to provide information processing capabilities in the system. The processor may comprise one or more of a digital processor, an analog processor, and a digital circuit designed to process information, an analog circuit designed to process information, a state machine, and/or other mechanisms for electronically processing information. Further a single integrated circuit chip and multiples integrated circuit chips. The processing unit can be any of various available processors, also dual microprocessors and other multiprocessor architectures. The at least one processor may comprise a plurality of processing units. These processing units may be physically located within the same device (e.g. a server) or the processor may represent processing functionality of a plurality of devices operating in coordination (e.g. a server, computing devices associated with a user, user interface, medical devices, devices that are part of external resources, and/or other devices). The processor may be configured via machine-readable instructions to execute one or more computer program components. The processor may be configured to execute the one or more components by software, hardware, firmware, some combination of software, hardware, and/or firmware; and/or other mechanism for configuring processing capabilities on the processor. The components may be co-located within a single processing unit. In embodiments in which processor comprises multiple processing units, one or more of the components may be located remotely from the other components. The processor may be configured to execute one or more additional components that may perform some or all of the functionality to one of the components. The computing system may further comprise a central processing unit (CPU), which may comprise a conventional microprocessor. The processor generally represents any type or form of processing unit capable of processing data or interpreting, executing, and/or directing execution of one or more of the instructions, processes and/or operations in accordance with one or more application or other computer-executable instructions such as may be stored in a storage device or another computer-readable medium.

The computing system may comprise one or more input/output devices and interfaces, such as a keyboard, a pointing device like a mouse, a touchpad, a touchscreen, a ring, a printer and the like. The computing system may further comprise one or more display devices, such as a monitor or a touchscreen that allows visual presentation of the visualized virtual agent and further may allow visual presentation of data to a user. A display device may provide for the presentation of graphical user interfaces (GUI), application software data, and multimedia presentations. The computing system may further comprise a microphone, motion sensor that allows a user to generate input to the computing system using sounds, voice, motion gestures or the like. The computing system may also comprise input/output devices and interfaces which may provide a communication interface to various external devices vie a link to a network. The computing system may also comprise one or more multimedia devices, such as speakers, video cards, graphics accelerator, and microphones. Input devices include, but are not limited to, a pointing device such as a mouse, trackball, stylus, touch pad, keyboard, microphone, joystick, game pad, satellite dish, scanner, TV tuner card, digital camera, digital video camera, web camera, and the like, a receiver, and RF or infrared receiver These and other input devices connect to the processing unit through the system bus via interface port. Interface port includes a serial port, a parallel port, a game port, and a universal serial bus (USB). Output devices use some of the same type of port as input devices. Thus a USB port may be used to provide input to computer and to output information from computer to an output device. Output devices are devices like monitors, speakers, and printers.

An operating system can be stored on disk storage acts to control and allocate resource of the computer system. Applications take advantage of the management of resources by an operating system through program modules and program data such as the boot/shutdown transaction table and the like, stored either in system memory or on disk storage. It is to be appreciated that virtual user-specific health advisor can be implemented with various operating systems or combinations of operating systems. The computing system may be controlled and coordinated by operating system software such Windows XP, Windows Vista, Windows 7, Windows 8, Windows 10, Linus, Solaris, Android, iOS; Blackberry OS, Palm OS, Windows Mobile, Windows Phone, or other compatible operating systems. The operating system may control and schedule computer processes for execution, perform memory management, provide file system, networking and input/output services and may provide a user interface such as a GUI and the like.

The user interface may be configured to receive user-specific input data from at least one input device and/or at least one sensor and/or configured to provide visual responses combined with audio responses to one or more users of the system. The user interface may be located in a personal computing device, wearable electronic device, a medical device, and/or locations within or outside the system. The user interface may be configured to provide an interface between the computing system and the user. This enables data, cues, results, and/or instructions and any other communicable items to be communicated between the user, processor, sensors, and/or other components of the system. Visual responses, audio responses, reviews, graphs, predictions and/or other information may be communicated from the system to the user via the user interface. Examples of interface devices suitable for inclusion in a user interface may comprise a graphical user interface, a display, a touchscreen, a keypad, buttons, switches, a keyboard, knobs, levers, speakers, a microphone, an indicator light, an audible alarm, a printer, a haptic feedback device, an optical scanner, a bar-code reader, a camera, and/or other interface devices. The user interface may comprise a plurality of separate interfaces for example a plurality of different interfaces associated with a plurality of computing devices associated with the user. An interface that may be part of a computing device associated with the user, processor, electronic storage, external resources, sensors, and/or other components of the system. A user interface may be included in a server that also includes a processor and/or electronic storage, and/or other interfaces. The user interface may be configured such that a user may receive visual responses combined with audio responses from the system via the individual ones of the plurality of user interfaces. The user interface may comprise at least one interface that is provided integrally with the processor and/or other components of the system.

The system may further comprise a storage component which may include user-specific input data related to the user that is provided by the user, a user of the system and/or provided by other components of the system. The component may be configured to adapt from user-specific input data in real time and dynamically update user-specific input data in the storage component. Other components of the system may be configured to dynamically adjust the analysis and output based on interactions with the user and based on recognized and/or measured physio-psychologic parameters of the user received through means of speech recognition, face recognition, measurement of pulse, measurement of breathing, measurement of blood pressure, and/or measurement of the electric conductivity of the skin in real or near real time.

The system may further comprise a component configured to generate visual and/or audio signals related to visual responses combined with audio responses of the visualized virtual agent. The information related to the visualized virtual agent may include verbal behavioral characteristics and non-verbal characteristics of the visualized virtual agent. For example, the generated visual and/or audio signals include information about how the visualized virtual agent looks, how it moves, how it reacts to interaction with the user, how it talks, the tone of the voice, the accent, the emotions expressed, and/or other information related to verbal behavioral characteristics and non-verbal characteristics of the visualized virtual agent. The component may include a verbal behavior generator for generating audio responses, a non-verbal behavior generator for generating visual responses, and/or other components. Verbal behavior generator is configured to generate verbal behavior characteristics of the visualized virtual agent. For example, speech recognition including features of speech (e.g. tone, pitch, accent, emotion, etc.), content of the speech, and/or other verbal behavior characteristics of the visualized virtual agent. Non-verbal behavior generator may be configured to generate non-verbal behavior characteristics of the visualized virtual agent. For example, appearance of the visualized virtual agent, emotional expressions, movements, expressions, body language, posture, and/or other non-verbal behavior characteristics of the visualized virtual agent. Audio and/or visual signals may be provided to the user during the user's performance of activities. Audio and visual signals may include feedback to the user's progress and/or entertainment. The signals may be played at predetermined points during an activity, based on performance metrics, or at the initiation of the user.

The system may include a central server which may include a controller, memory and communication model. A user may download data collected about his activities from the user's electronic device into the central server. The memory of the central server may be configured to store the user's data in a user-specific profile. A local server may include a user's personal computer. User-specific profiles or user-specific input data may be stored in the respective memories of a central server, local server and/or electronic device. The computing system may be coupled to a network such as a LAN, WAN or the Internet, for example, via a wired, wireless or combination of wired and wireless, communication link. The network may communicate with different computing devices and/or other electronic devices via wired or wireless communication links. Access to the electrical system of the computer system by computing systems and/or by data sources may be through web-enabled user access point such as the computing system or data source of personal computer, mobile device, cellular phone, smartphone, smartwatch, laptop, tablet computer, e-reader device, audio player or other device capable of connecting or configured to connect to the network. Such devices may have a browser module or specific application that is implemented as a module that uses text, graphics, audio, video, and other media to present data and to allow interaction with data via the network. The computing device may operate in a networked environment using logical connections to one or more remote computers, such as a remote computer. The remote computer can be a personal computer, a server, a router, a network PC, a workstation, a microprocessor based appliance, a peer service, a smart phone, a table, or other network node. A Network interface encompasses wire and/or wireless communication networks such as local-area networks (LAN) and wide area networks (WAN) and cellular networks. LAN technologies include Fiber Distributed Data Interface (FDDI), Copper Distributed Data Interface (CDDI), Ethernet, Token Ring. WAN technologies include, but are not limited to, point-to-point links, circuit switching networks like Integrated Services Digital Networks (ISDN) and variations thereof, packet switching networks, and Digital Subscriber Lines (DSL). Hardware and/or Software necessary for connection to the network interface includes, for example, internal and external technologies such as, modems including regular telephone grad modems and DSL modems, ISDN adapters, and wired and wireless Ethernet cards, hubs and routers.

The system may also include one or more servers. The servers can also be hardware or hardware in combination with software. One possible communication between a client and server can be in form of a data packet transmitted between two or more computer processes wherein the data packet may include video data. The data packet can include meta data, like associated contextual information. The system may include a communication framework (like a global communication network such as the Internet, or mobile networks that can be employed to facilitate communication between the client computing devices/electronic devices and the servers Communications can be facilitated via a wired (including optical fiber) and/or wireless technology. The clients may include or are operatively connected to one or more client data stores that can be employed to store information local to the clients (like. associated contextual information). Similarly, the servers are operatively included or are operatively connected to one or more server data store than can be employed to store information local to the servers. A client can transfer an encoded filed to a server. The server can store the file, decode the file, or transmit the file to another client. A client can also transfer an uncompressed file to a server and the server may compress the file. A server may encode video information and transmit the information via communication framework to one or more clients.

Access to the electrical system of the computer system by computing systems and/or by data sources may be through web-enabled user access point such as the computing system or data source of personal computer, mobile device, cellular phone, smartphone, smartwatch, laptop, tablet computer, e-reader device, audio player or other device capable of connecting or configured to connect to the network. Such device may have a browser module or specific application that is implemented as a module that uses text, graphics, audio, video, and other media to present data and to allow interaction with data via the network.

The computer can operate in a networked environment using logical connections to one or more remote computers, such as a remote computer. The remote computer can be a personal computer, a server, a router, a network PC, a workstation, a microprocessor based appliance, a peer service, a smart phone, a table, or other network node. Network interface encompasses wire and/or wireless communication networks such as local-area networks (LAN) and wide area networks (WAN) and cellular networks. LAN technologies include Fiber Distributed Data Interface (FDDI), Copper Distributed Data Interface (CDDI), Ethernet, Token Ring. WAN technologies include, but are not limited to, point-to-point links, circuit switching networks like Integrated Services Digital Networks (ISDN) and variations thereon, packet switching networks, and Digital Subscriber Lines (DSL). Hardware/Software necessary for connection to the network interface includes, for exemplary purposes only, internal and external technologies such as, modems including regular telephone grad modems and DSL modems, ISDN adapters, and wired and wireless Ethernet cards, hubs and routers. The system also includes one or more servers. The servers can also be hardware or hardware in combination with software. The servers can house threads to perform transformations by employing aspects of this disclosure. One possible communication between a client and server can be in form of a data packet transmitted between two or more computer processes wherein the data packet may include video data. The data packet can include a meta data, e.g. associated contextual information, for example. The system includes a communication framework (e.g. a global communication network such as the Internet, or mobile networks that can be employed to facilitate communication between the clients and the servers. (Clients=computing devices/electronic devices) Communications can be facilitated via a wired (including optical fiber) and/or wireless technology. The clients include or are operatively connected to one or more client data stores that can be employed to store information local to the clients (e.g. associated contextual information). Similarly, the servers are operatively include or are operatively connected to one or more server data store than can be employed to store information local to the servers. A client can transfer an encoded filed to a server. The server can store the file, decode the file, or transmit the file to another client. A client can also transfer uncompressed file to a server and server can compress the file in accordance with the disclosed subject matter. Server can encode video information and transmit the information via communication framework to one or more clients.

The computing system may comprise a display device like a liquid crystal display, a plasma display or other types and/or combinations of displays. The computing system may comprise a physical or logical connection between a remote microprocessor and a mainframe host computer for the purpose of uploading, downloading, or viewing interactive data and databases online in real time. The remote microprocessor may be operated by an entity operating the computer system including client server systems or main server systems and/or may be operated by one or more of data sources and/or one or more of computing systems. The computing system may communicate with other data sources and/or other computing devices and may comprise one or more internal and/or external data sources. One or more of said data sources may use a relational database as well as other types of databases.

The systems and components as described herein for one or more embodiments according to the present invention are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

DESCRIPTION OF THE FIGURES

FIG. 16 shows a first example of a color change response provided by a visualized virtual agent according to an embodiment of the present invention on display 101, 207, 307, 407, 507.

FIG. 17 shows a second example of a color change response provided by a visualized virtual agent according to an embodiment of the present invention on display 101, 207, 307, 407, 507.

Figure 1:
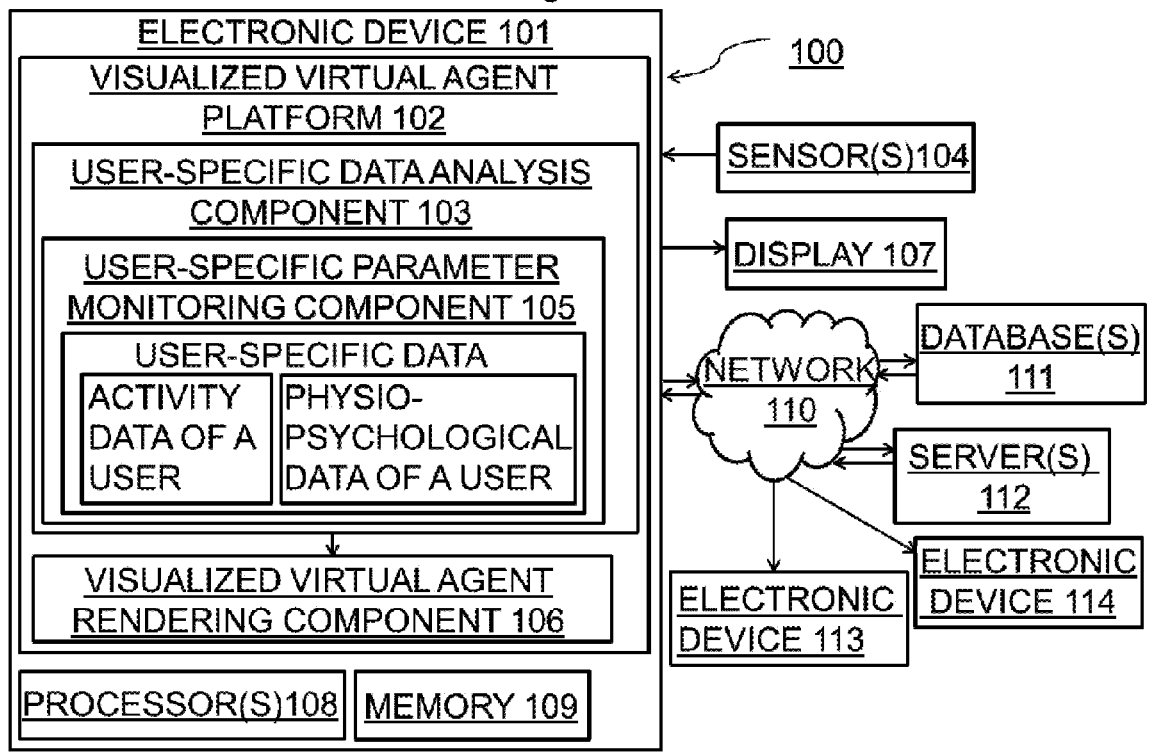
FIG. 1 shows a first example system 100 for providing a visualized virtual agent according to an embodiment of the present invention.
Figure 2:
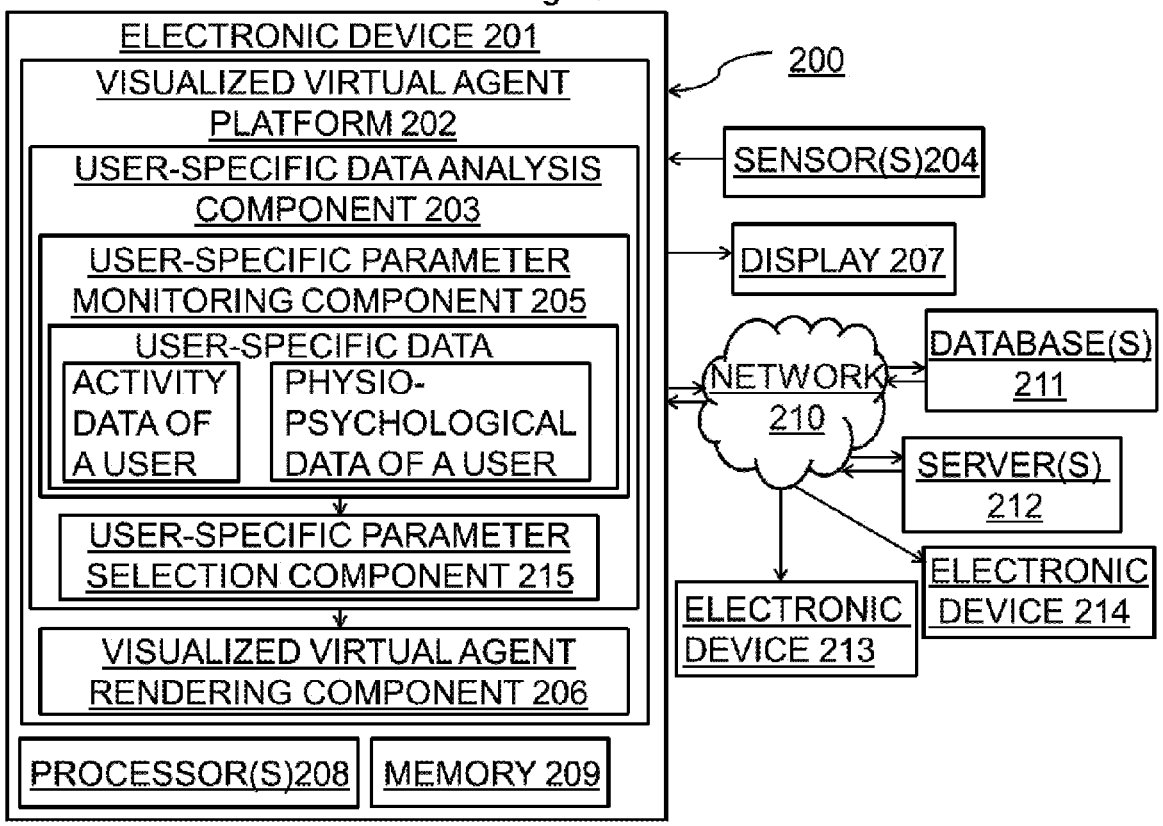
FIG. 2 shows a second example system 200 for providing a visualized virtual agent according to an embodiment of the present invention.
Figure 3:
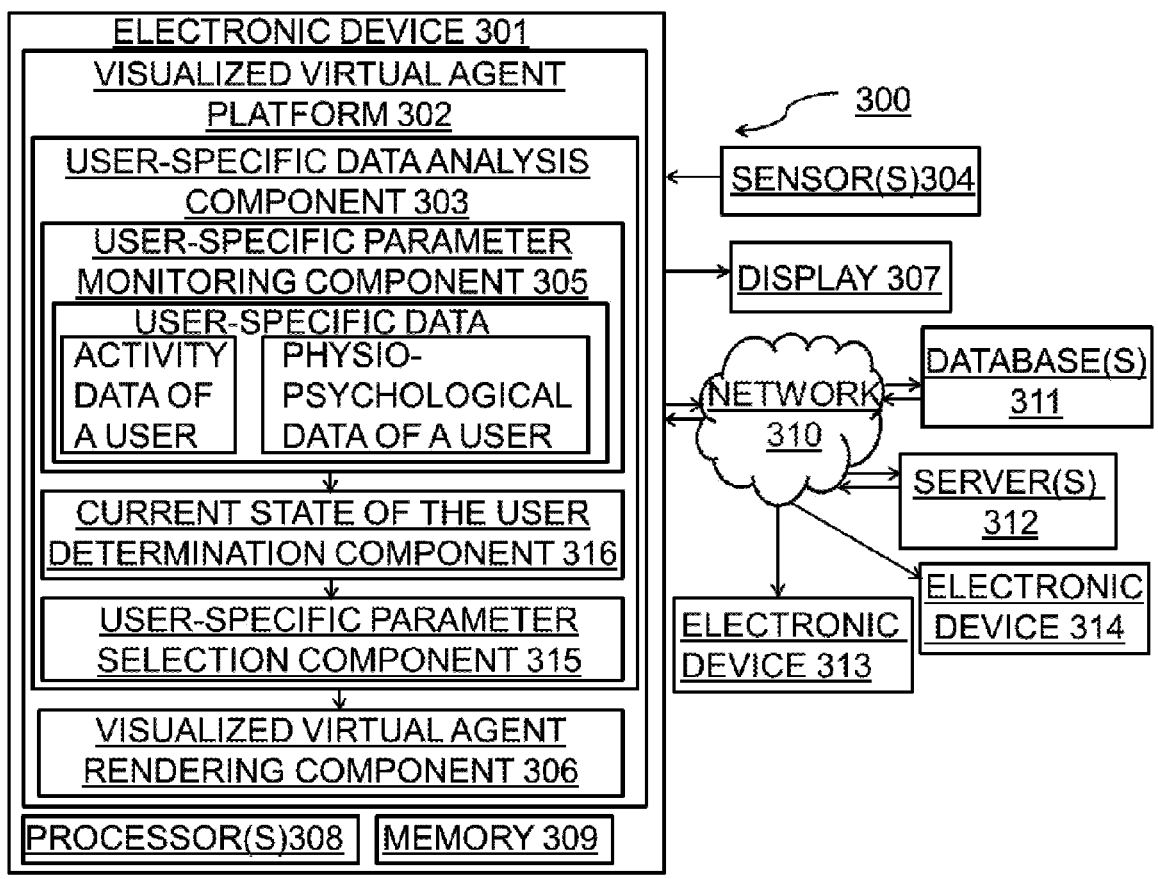
FIG. 3 shows a third example system 300 for providing a visualized virtual agent according to an embodiment of the present invention.
Figure 4:
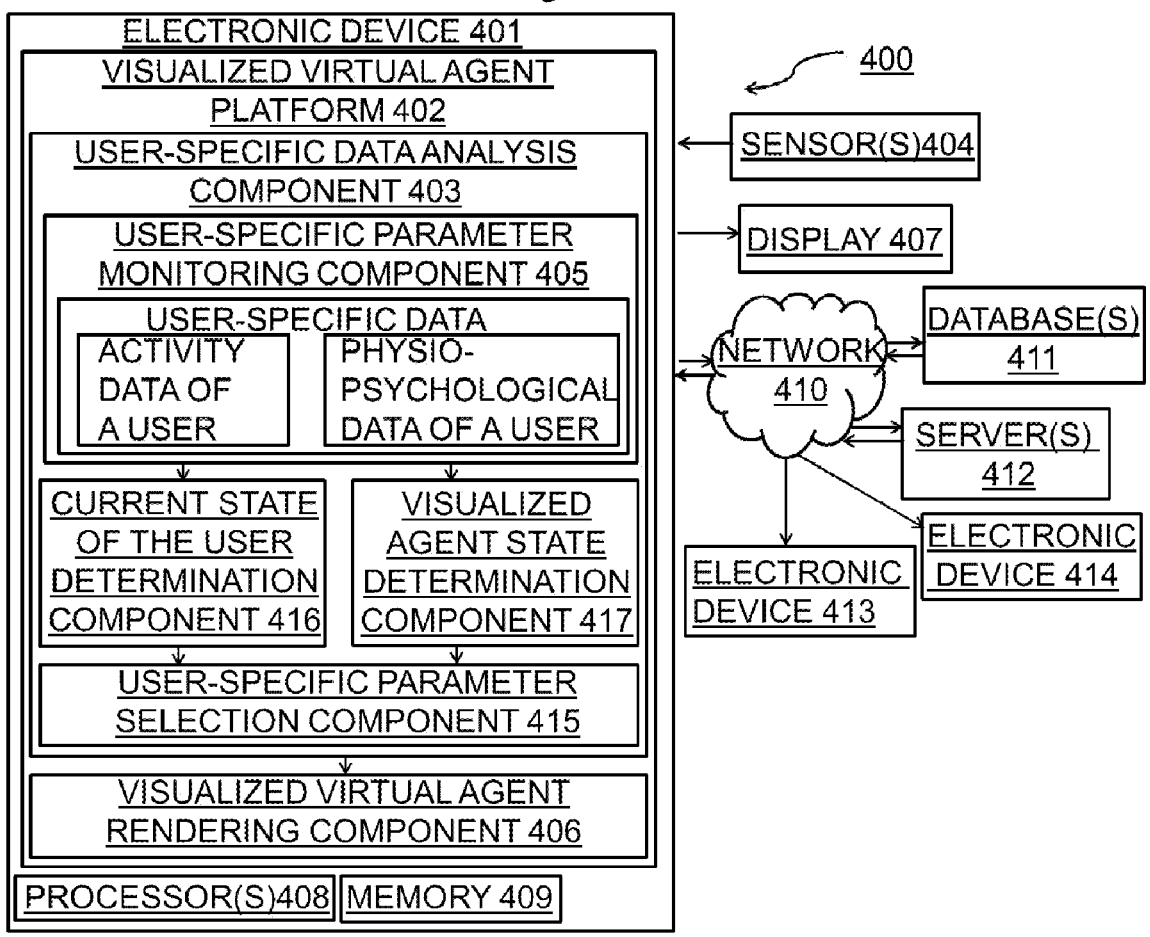
FIG. 4 shows a fourth example system 400 for providing a visualized virtual agent according to an embodiment of the present invention.
Figure 5:
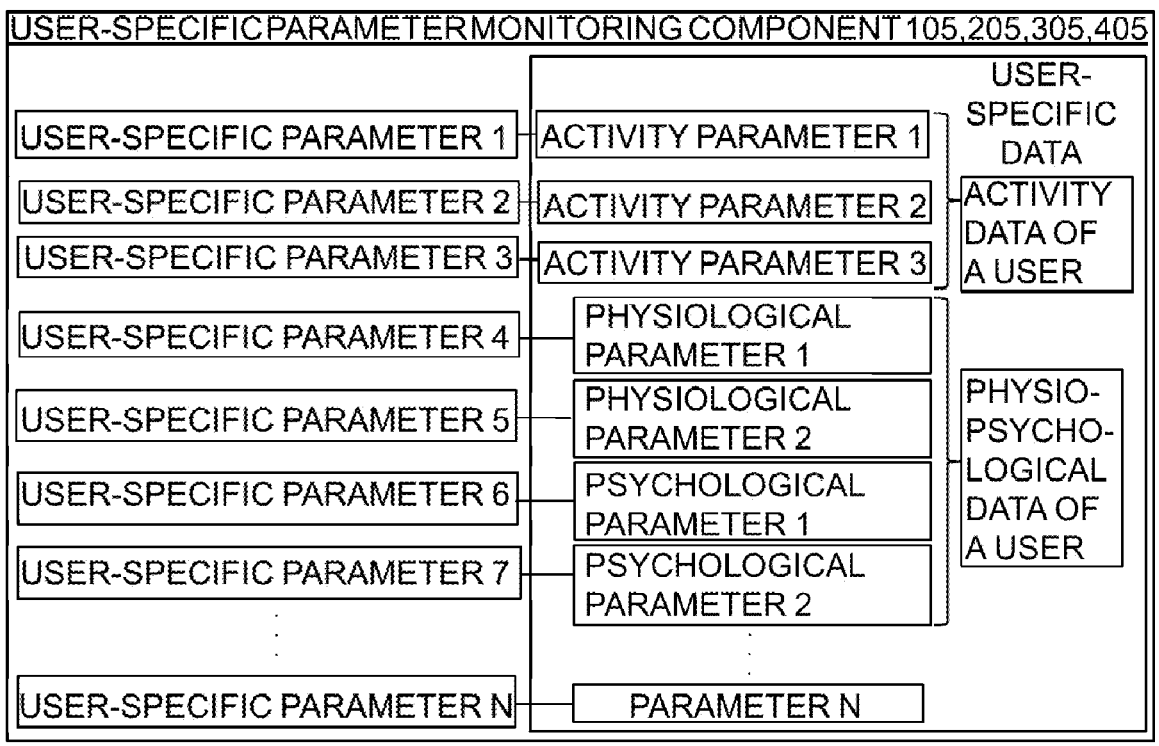
FIG. 5 shows an exemplary user-specific parameter monitoring component 105, 205, 305, 405 according to an embodiment of the present invention.
Figure 6:
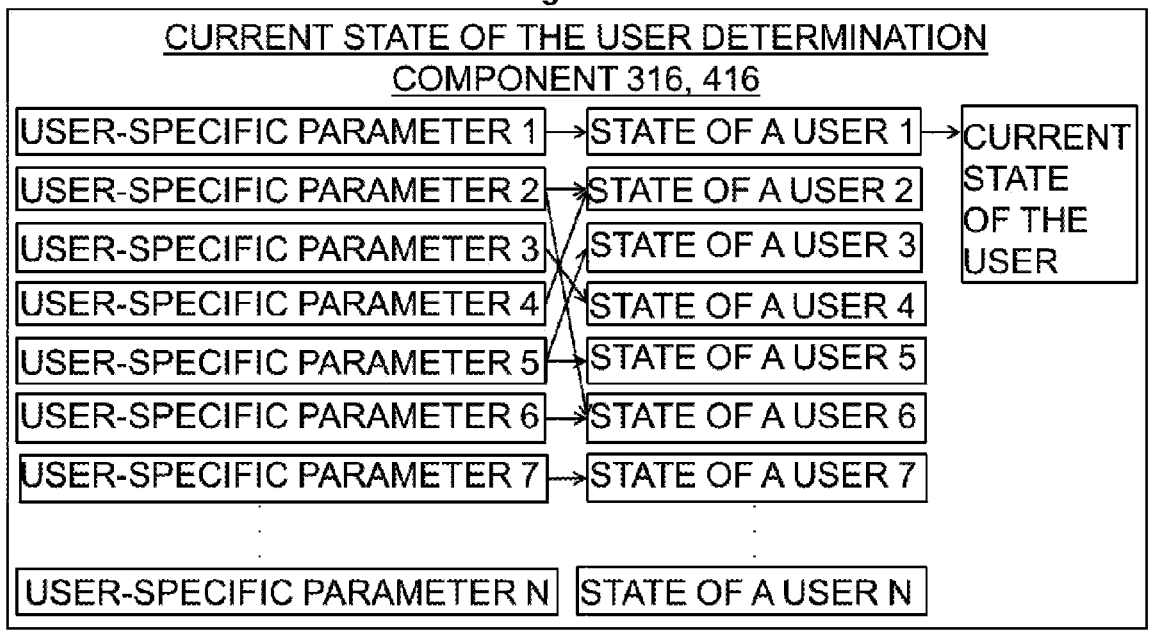
FIG. 6 shows an exemplary current state of the user determination component 316, 416 according to an embodiment of the present invention.
Figure 7:
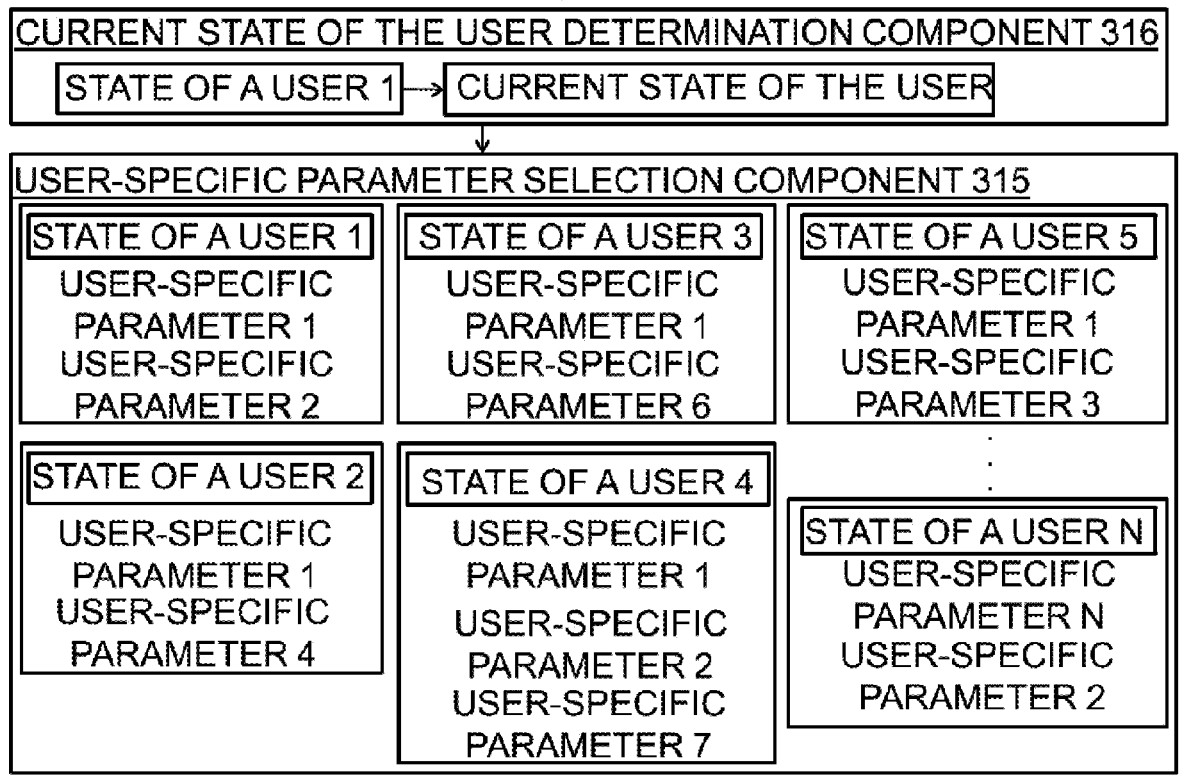
FIG. 7 shows an exemplary user-specific parameter selection component 315 according to an embodiment of the present invention.
Figure 8:
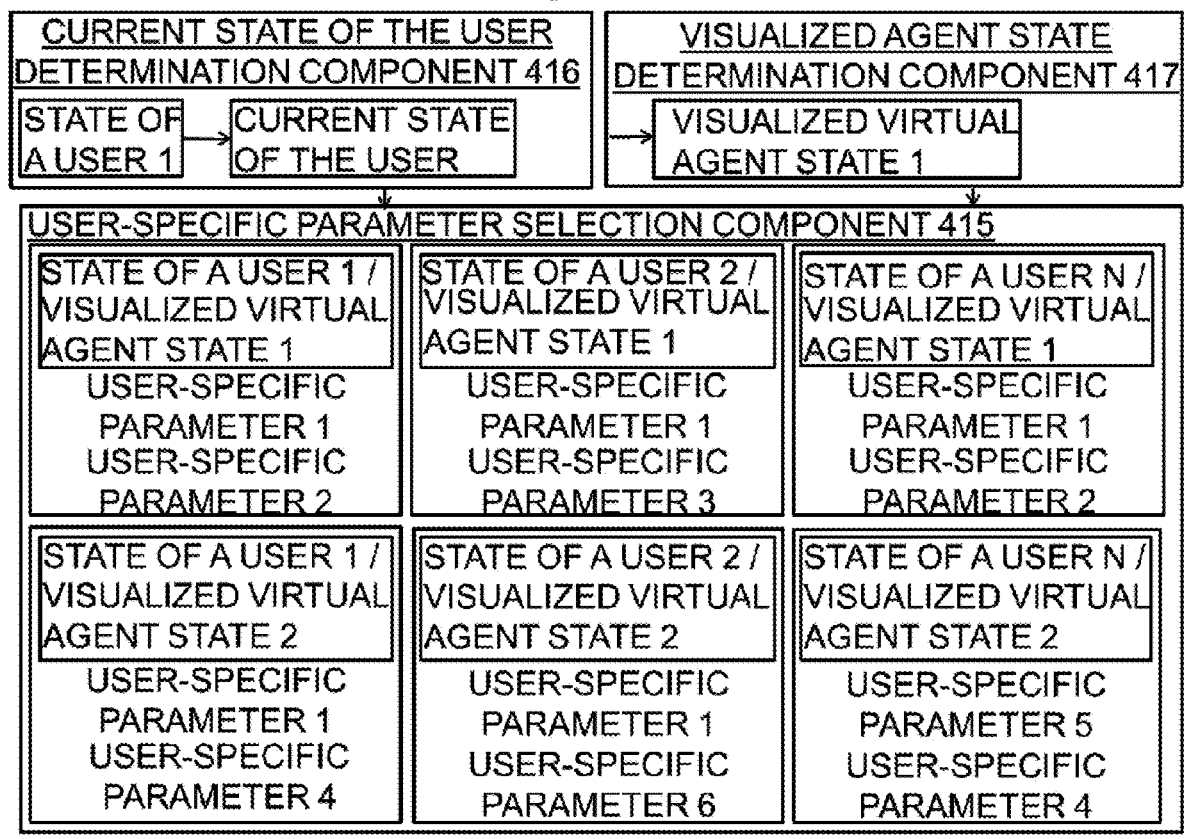
FIG. 8 shows an exemplary user-specific parameter selection component 415 according to an embodiment of the present invention.
Figure 9:
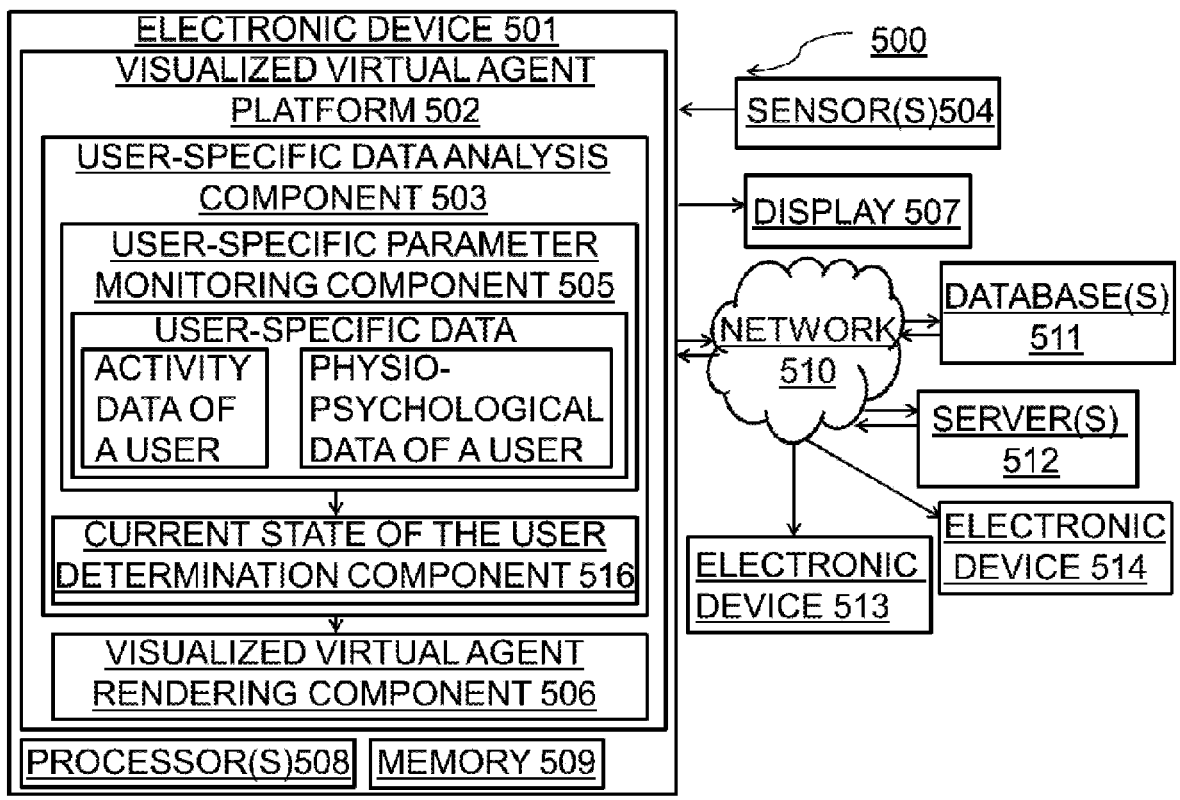
FIG. 9 shows a fifth example system 500 for providing a visualized virtual agent according to an embodiment of the present invention.
Figure 10:
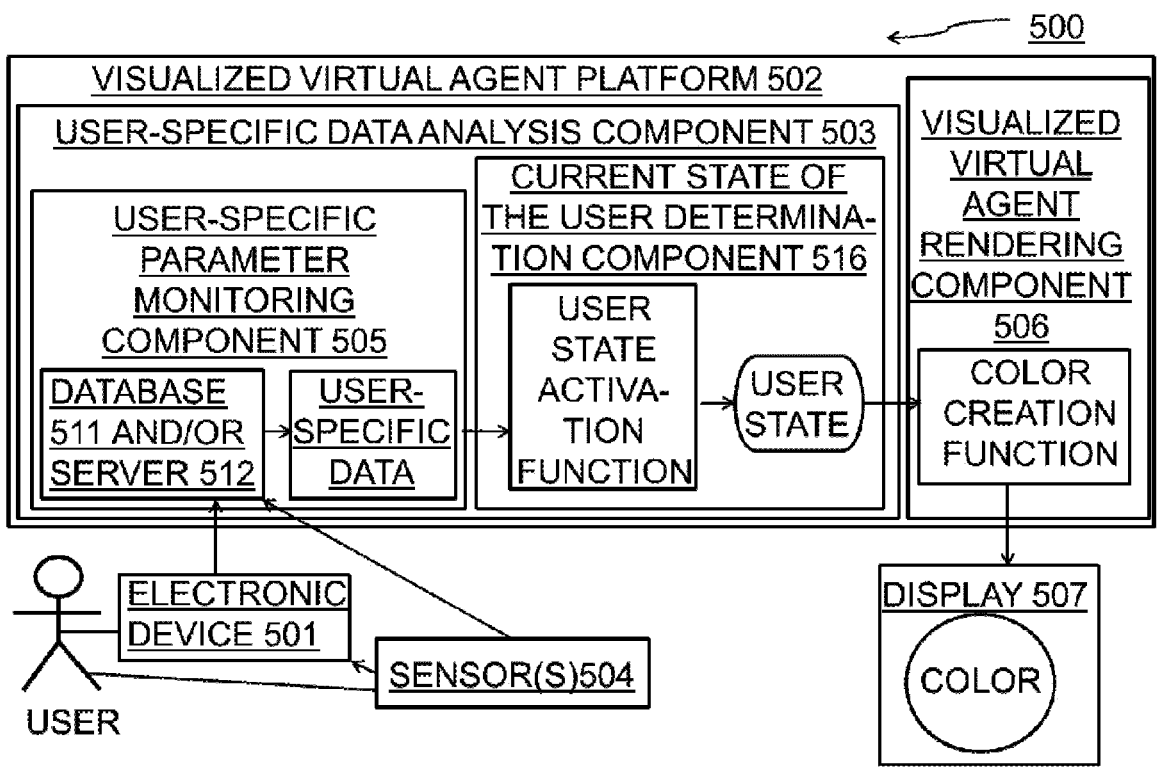
FIG. 10 shows a further example for the example system 500 for providing a visualized virtual agent according to an embodiment of the present invention.
Figure 11:
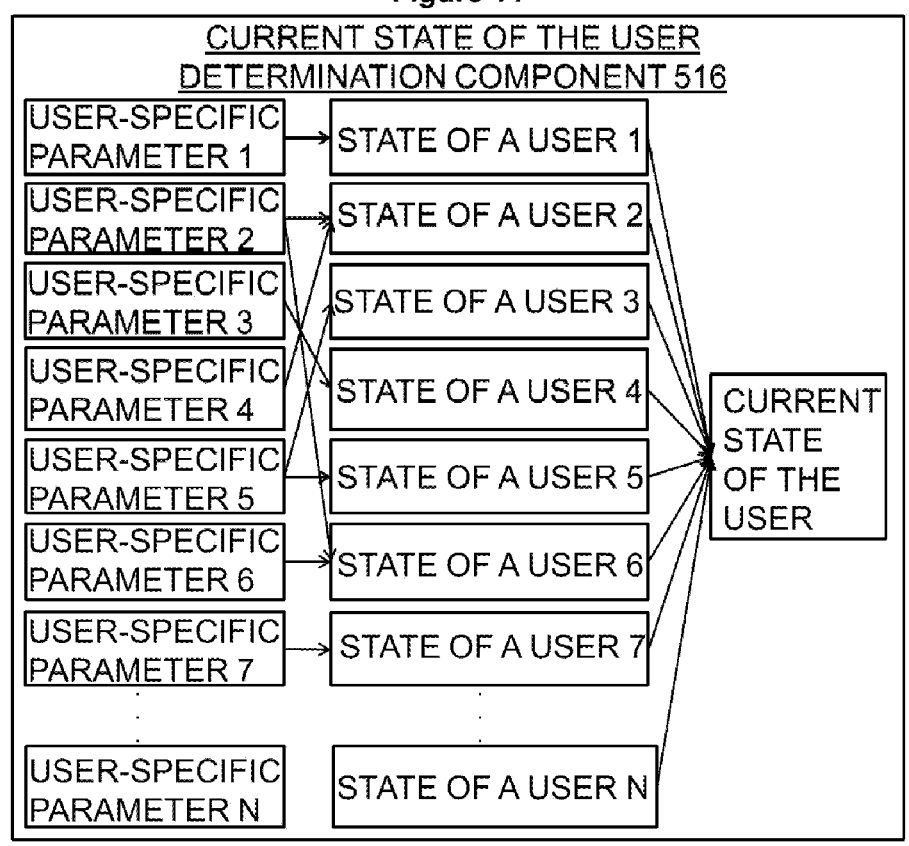
FIG. 11 shows a first exemplary current state of the user determination component 516 according to an embodiment of the present invention.
Figure 12:
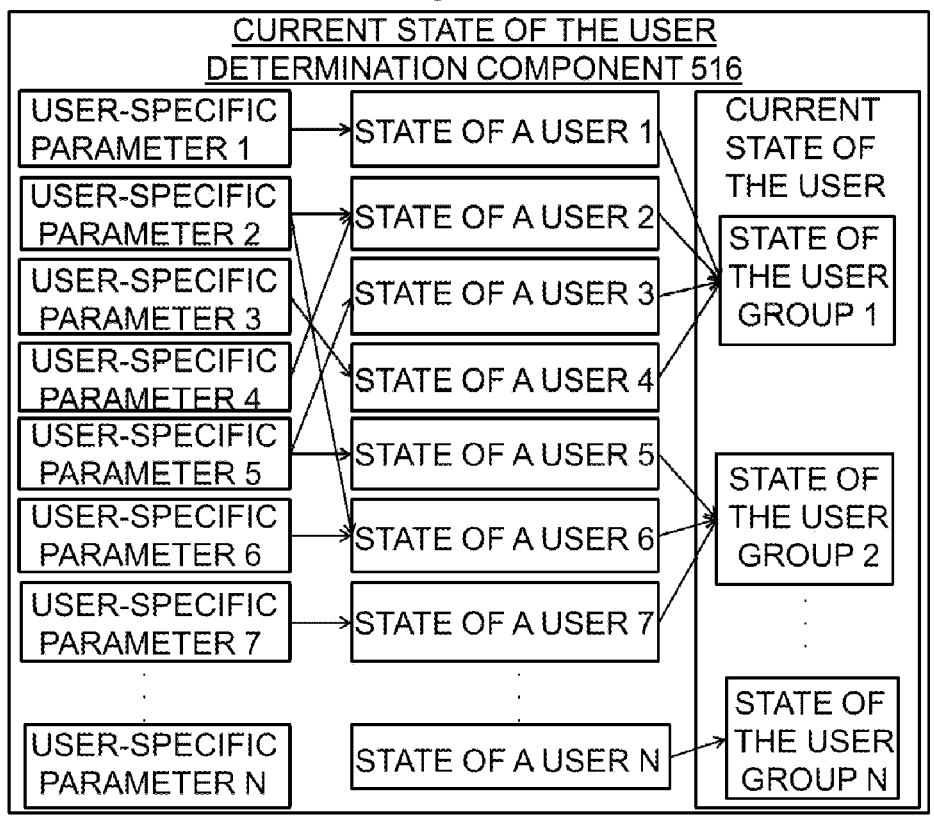
FIG. 12 shows a second exemplary current state of the user determination component 516 according to an embodiment of the present invention.
Figure 13:
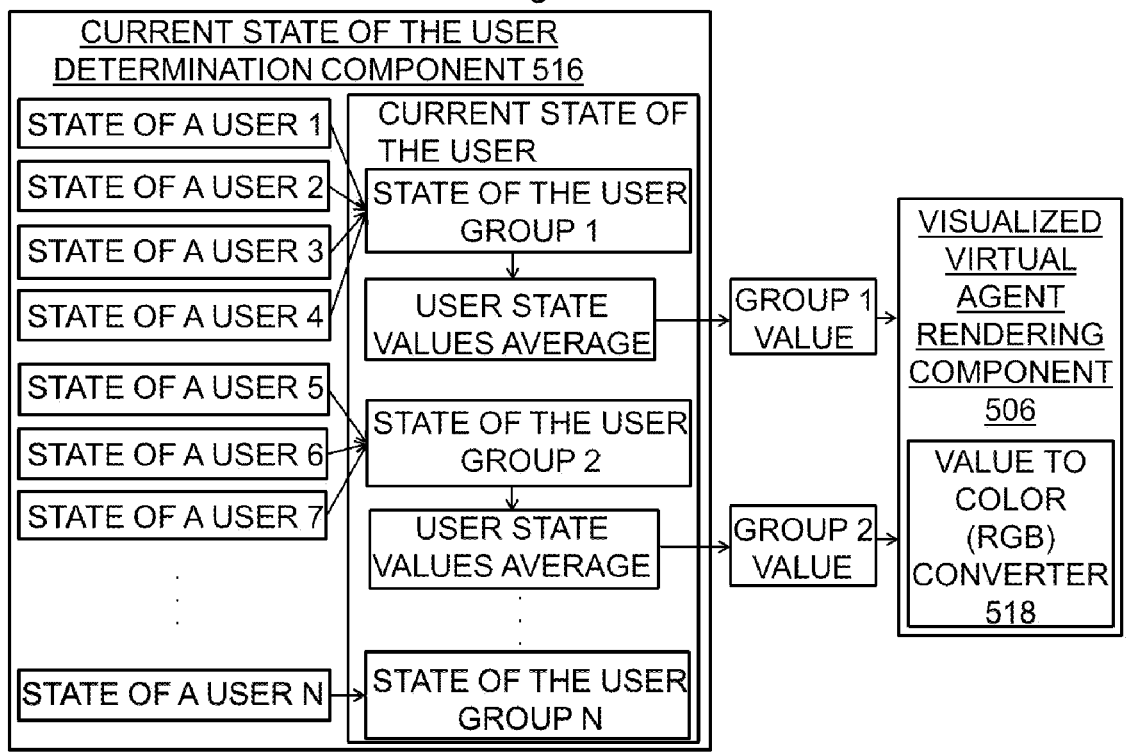
FIG. 13 shows the exemplary current state of the user determination component 516 from FIG. 12 interaction with the visualized virtual agent rendering component 506 according to an embodiment of the present invention.
Figure 14:
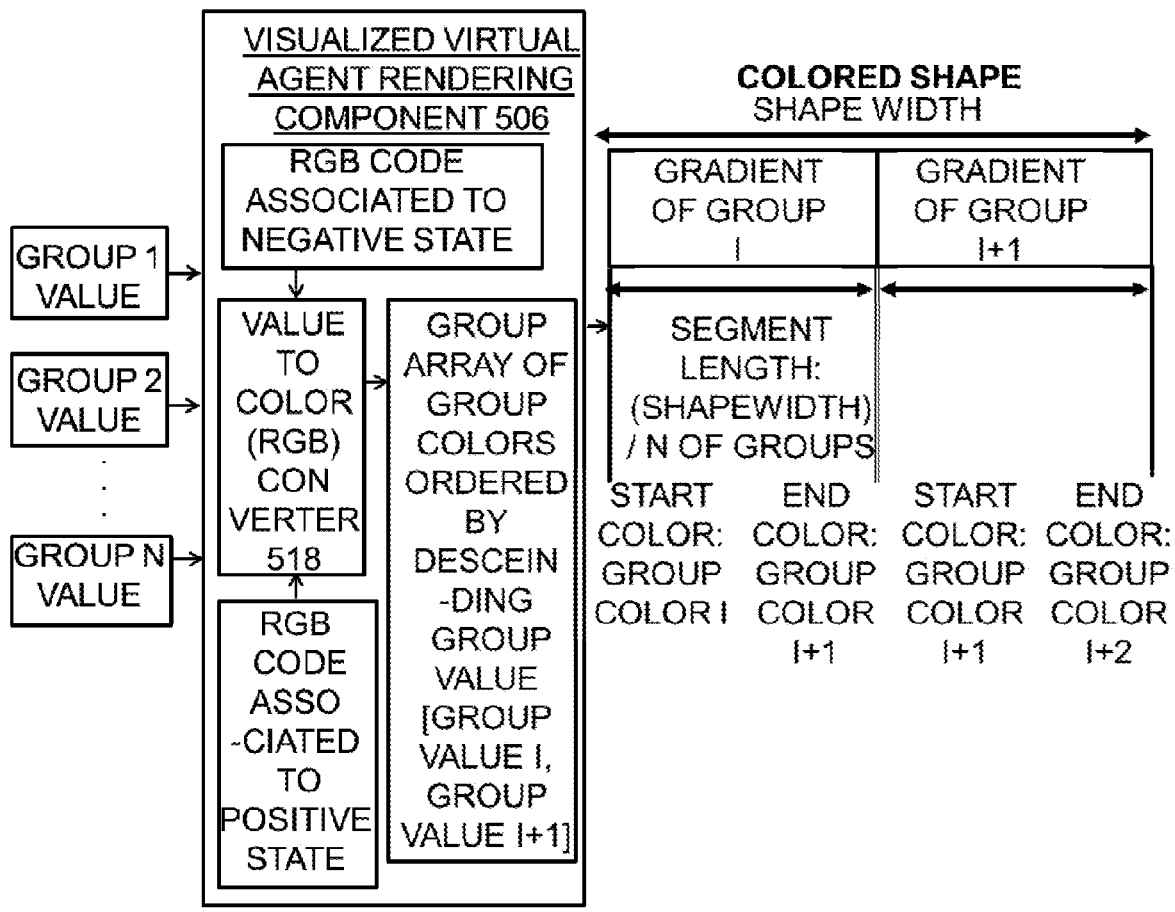
FIG. 14 shows the exemplary visualized virtual agent rendering component 506 according to an embodiment of the present invention.
Figure 15:
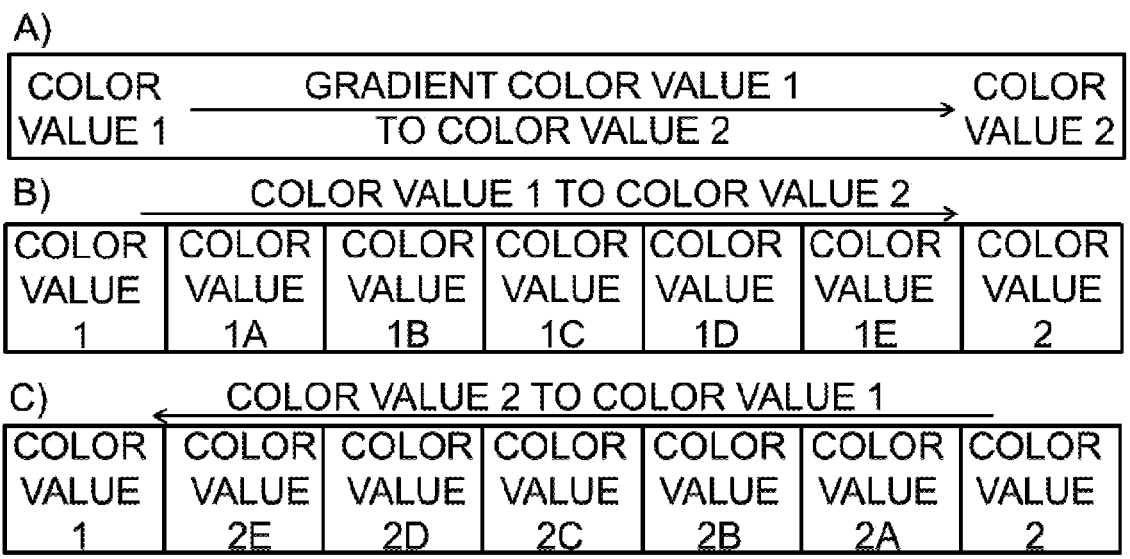
FIG. 15 shows exemplary implementation for providing a color gradient from a color value 1 to a color value 2 for generating a color change of the visualized virtual agent according to an embodiment of the present invention.
Figure 18:
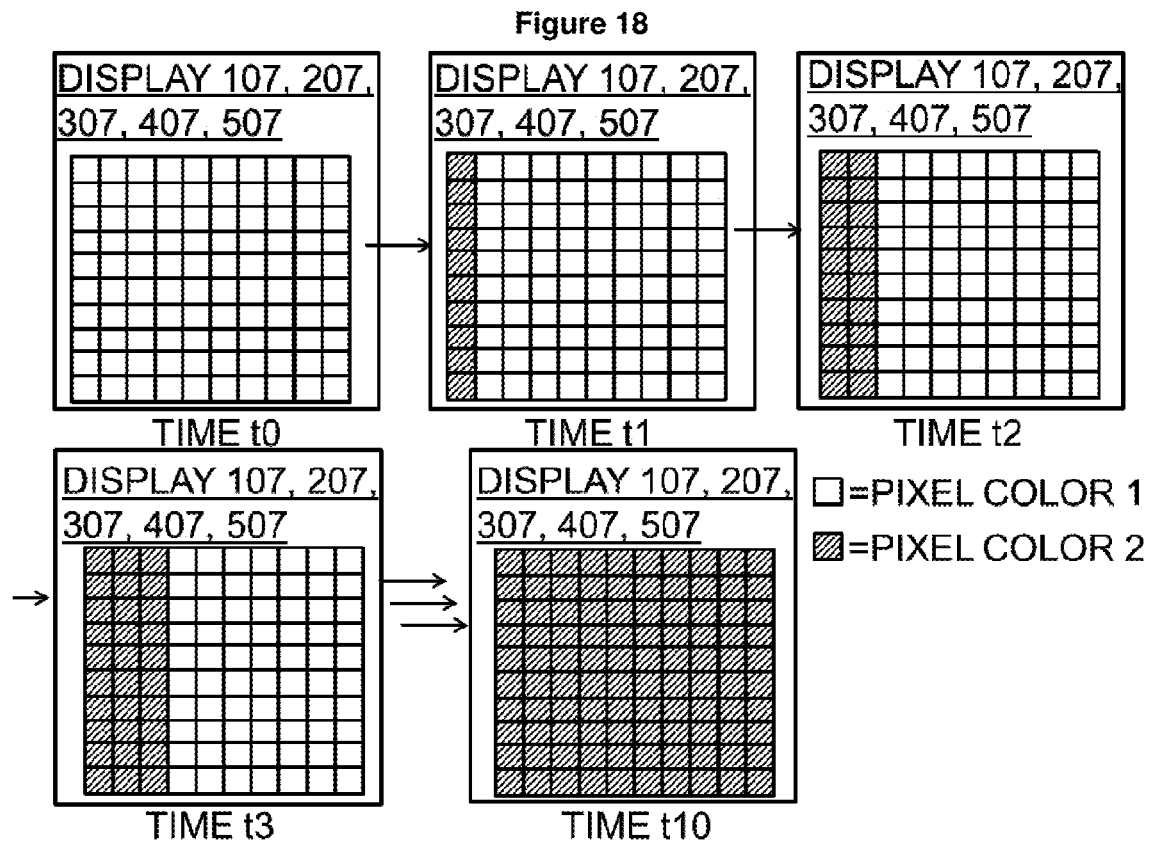
FIG. 18 shows a third example of a color change response provided by a visualized virtual agent according to an embodiment of the present invention on display 101, 207, 307, 407, 507.
Figure 19:
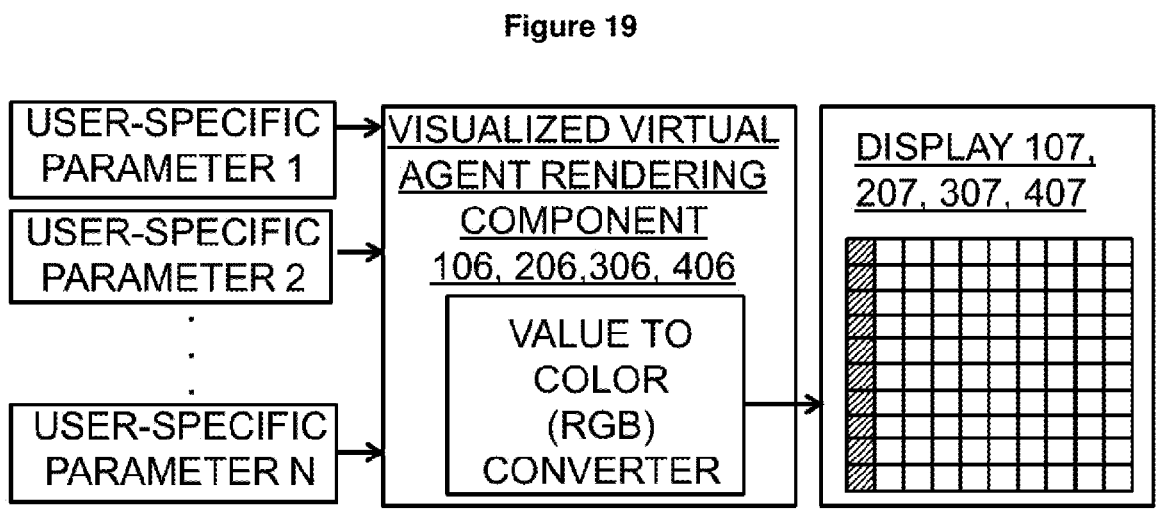
FIG. 19 shows an exemplary visualized virtual agent rendering component 106, 206, 306, 406 according to an embodiment of the present invention.
Figure 20:
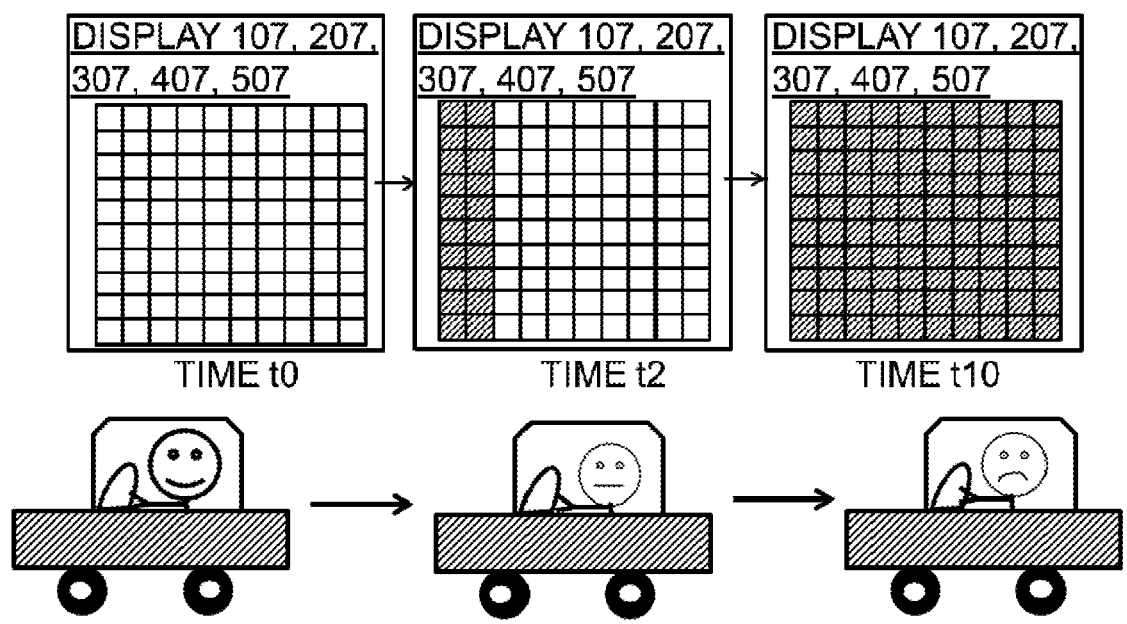
FIG. 20 shows a fourth example of a color change response provided by a visualized virtual agent according to an embodiment of the present invention on display 101, 207, 307, 407, 507 for a driving state of a user.

What is claimed is:

1. A computer-implemented method for providing a visualized virtual agent configured to provide a visual response to a user and configured to monitor over time one or more user-specific parameter,
    wherein user-specific data for at least one user-specific parameter are acquired by at least one sensor, the user-specific parameter comprising activity data of the user and/or physio-psychological data of the user,
    wherein the visualized virtual agent is configured to provide an artificial physiological color change response to a user for a current state of the user and/or for at least one visualized virtual agent state,
    wherein the at least one visualized virtual agent state and/or the current state of the user is determined on the basis of the activity data of the user and/or of the physio-psychological data of the user;
    wherein the visualized virtual agent is configured to adapt the artificial physiological color change response to monitored changes of the activity data of the user and/or the physio-psychological data of the user,
    wherein the adaption of the artificial physiological color change response comprises at least in part a color change of the visualized virtual agent for the at least one visualized virtual agent state and/or the current state of the user,
    the method comprising the following steps:
        monitoring over time, by a user-specific parameter monitoring component, one or more user-specific parameter of a user, the one or more user-specific parameter comprising activity data of the user and/or physio-psychological data of the user, and
        acquiring, by the user specific parameter monitoring component, user-specific data for at least one user-specific parameter by at least one sensor;
        determining, by a current state of the user determination component, a current state of the user on the basis of the activity data of the user and/or the physio-psychological data of the user and/or
        determining, by a visualized virtual agent state determination component, a visualized virtual agent state on the basis of the activity data of the user and/or the physio-psychological data of the user;
        analyzing, by a user-specific data analysis component, the monitored one or more user-specific parameter of the user for the determined current state of the user and/or determined visualized virtual agent state;

determining, by the user-specific data analysis component, monitored changes of the activity data of the user and/or the physio-psychological data of the user;

providing, by the user-specific data analysis component, the monitored changes of the activity data of the user and/or the physio-psychological data of the user to a visualized virtual agent rendering component;

adapting, by the visualized virtual agent rendering component, the artificial physiological color change response to the monitored changes of the activity data of the user and/or the physio-psychological data of the user, wherein the adaption of the artificial physiological color change response comprises at least in part a color change of the visualized virtual agent in the range between a first color value and a second color value, wherein the at least in part color change of the visualized virtual agent comprises adapting a specific amount of pixels of the visualized virtual agent rendered with the first color value to the second color value, or adapting a specific amount of pixels of the visualized virtual agent rendered with the second color value to the first color value; wherein the color of the visualized virtual agent does not change completely at once within a short time frame from the first color value to the second color value or from the second color value to the first color value; and rendering, by the visualized virtual agent rendering component, the visualized virtual agent on a display device;

wherein the artificial physiological color change is defined as a flowing change in color distributed over the whole shape of the visualized virtual agent.

2. The computer-implemented method according to claim 1, wherein the method further comprises the step:

determining, by a user-specific parameter selection component, a selection of one or more user-specific parameter based on the determined current state of the user and/or based on the determined visualized virtual agent state.

3. The computer-implemented method according to claim 1, wherein determining the current state of a user comprises determining a selection of one or more user-specific parameter as a basis for generating of the artificial physiological color change response to the user.

4. The computer-implemented method according to claim 1, wherein the visualized virtual agent is configured to monitor, to collect and to analyze a plurality of data for a plurality of user-specific parameter for activity data of a user and/or physio-psychological data of a user and is configured to determine the current state of the user based on the monitored, collected and analyzed plurality of data and is configured to determine a selection of one or more user-specific parameter selected from the entire user-specific parameter in order to provide a specific selection of one or more user-specific parameter as a basis for generating the artificial physiological color change response to the user.

5. The computer-implemented method according to claim 1, wherein the visualized virtual agent is configured to provide an artificial physiological color change response to a user based on a first selection of one or more user-specific parameter from the activity data of a user and/or the physio-psychological data of a user for a first state of a user and be further configured to provide an artificial physiological color change response to a user based on a second selection of one or more user-specific parameter from the activity data of a user and/or physio-psychological data of a user for a second state of a user, wherein the visualized virtual agent is configured to change between the first state of the user and the second state of the user.

6. The computer-implemented method according to claim 1, wherein determining the visualized virtual agent state comprises determining a selection of one or more user-specific parameter as a basis for generating of the artificial physiological color change response to the user and wherein the visualized virtual agent is configured to provide an artificial physiological color change response to a user based on a first selection of one or more user-specific parameter from the activity data of a user and/or the physio-psychological data of a user for a first visualized virtual agent state and be further configured to provide an artificial physiological color change response to a user based on a second selection of one or more user-specific parameter from the activity data of a user and/or physio-psychological data of a user for a second visualized virtual agent state, wherein the visualized virtual agent is configured to change between the first visualized virtual agent state and the second visualized virtual agent state.

7. The computer-implemented method according to claim 6, wherein the first visualized virtual agent state comprises an active communication visualized virtual agent state and the second visualized virtual agent state comprises a passive or monitoring visualized virtual agent state.

8. The computer-implemented method according to claim 1, wherein the visualized virtual agent is configured to provide different artificial physiological color change responses to a user on the basis of different specific selections of one or more user-specific parameter of activity data of a user and/or physio-psychological data of a user for different visualized virtual agent states and different states of a user, wherein the visualized virtual agent is configured to change between each visualized virtual agent state and/or each state of the user in order to provide artificial physiological color change responses for the current situation of a user.

9. The computer-implemented method according to claim 1, wherein the visualized virtual agent is configured to provide long-term recognizing and/or measuring and/or monitoring of activity parameter and/or physio-psychological parameter of the user over time and/or wherein the visualized virtual agent is displayed two dimensionally or three dimensionally on the display device.

10. The computer-implemented method according to claim 1, wherein the physio-psychological data of the user are based on a present behavior and/or a current physiological condition and/or a current mental state and/or medical condition of the user.

11. The computer-implemented method according to claim 1, wherein the visual response comprises a posture, and/or a motion of the visualized virtual agent and wherein an audio response comprises a sound, a sound volume, an emphasis, and/or an accent of the visualized virtual agent on the basis of the activity data of the user and/or physio-psychological of the user.

12. The computer-implemented method according to claim 1, wherein the at least one sensor comprises audio-visual sensors, activity sensors, physiological sensors, biometric sensors, a heart rate sensor, a blood pressure sensor/monitor, a weight scale, motion sensors, an optical sensor, a video sensor, an audio sensor, a blood glucose monitor, a blood oxygen saturation monitor, a hydration monitor, a skin/body temperature thermometer, a respiration monitor, electroencephalogram (EEG) electrodes, bed sensors, accelerometer, activity sensors/trackers, a video camera, a depth sensor, an electro dermal activity (EDA) sensor, a portable global positioning system (GPS) sensor, and/or a microphone and/or wherein the at least one sensor is configured to acquire physio-psychologic parameters of the user by speech recognition, face recognition, measurement of pulse, measurement of breathing, measurement of blood pressure, and/or measurement of the electric conductivity of the skin.

13. The computer-implemented method according to claim 1, wherein the visualized virtual agent is configured to provide a color change response comprising at least in part a color change of the visualized virtual agent in the range between a first color value and a second color value, wherein the range between the first color value and the second color value is subdivided into intervals, wherein for each interval and subsequent interval a specific amount of the pixels is adapted to the second color value, wherein the visualized virtual agent is rendered with the first color by 100% of the pixel of the visualized virtual agent and for each of the intervals in the range between the first and the second color value, at least in part of the pixels add up and are rendered with the second color until reaching the second color value, where 100% of the pixels of the visualized virtual agent is rendered with the second color.

14. A system for providing a visualized virtual agent providing an artificial physiological color change response to a user, the system comprising:
   a memory;
   at least one sensor configured to collect sensor data for at least one user-specific parameter of the user,
   at least one display device configured to display the visualized virtual agent;
   at least one processor configured to execute executable components stored on the memory, the executable components comprising:
      a user-specific parameter monitoring component configured to monitor one or more user-specific parameter of the user, wherein the user-specific parameter monitoring component is configured to receive user-specific data for one or more user-specific parameter of the user, the user-specific parameter comprising activity data of the user and/or physio-psychological data of the user, wherein user-specific data for at least one user-specific parameter are acquired from the at least one sensor;
      a user-specific data analysis component configured to analyze the user-specific data monitored by the user-specific parameter monitoring component and to determine monitored changes of the activity data of the user and/or physio-psychological data of the user;
      a visualized virtual agent rendering component configured to adapt the artificial physiological color change response to the determined monitored changes of the activity data of the user and/or the physio-psychological data of the user, wherein the adaption of the artificial physiological color change response comprises at least in part a color change of the visualized virtual agent in the range between a first color value and a second color value, wherein the at least in part color change of the visualized virtual agent comprises adapting a specific amount of pixels of the visualized virtual agent rendered with the first color value to the second color value, or adapting a specific amount of pixels of the visualized virtual agent rendered with the second color value to the first color value; wherein the color of the visualized virtual agent does not change completely at once within a short time frame from the first color value to the second color value or from the second color value to the first color value;
   wherein the user-specific data analysis component further comprises:
      a current state of the user determination component configured to determine a current state of the user based on the user-specific data monitored by the user-specific parameter monitoring component, and/or
      a visualized virtual agent state determination component configured to determine a visualized virtual agent based on the user-specific data monitored by the user-specific parameter monitoring component,
   wherein the artificial physiological color change is defined as a flowing change in color distributed over the whole shape of the visualized virtual agent.

15. The system according to claim 14, wherein the user-specific data analysis component further comprises:
   a user-specific parameter selection component configured to determine a selection of one or more user-specific parameter from the one or more user-specific parameter as a basis for generating of the artificial physiological color change response.

* * * * *